United States Patent
Peterson et al.

(10) Patent No.: US 12,064,343 B2
(45) Date of Patent: Aug. 20, 2024

(54) DEVICES AND METHODS FOR MULTI-ALIGNMENT OF IMPLANTABLE MEDICAL DEVICES

(71) Applicant: Medtronic, Inc., Minneapolis, MN (US)

(72) Inventors: Justin R. Peterson, Santa Rosa, CA (US); Victoria Ung, Santa Rosa, CA (US); James E. Mitchell, Windsor, CA (US); Syed J. Askari, San Jose, CA (US); Shahnaz Javani, Santa Rosa, CA (US); Genevieve E. Farrar, Novato, CA (US); Stuart E. Kari, Windsor, CA (US); Mark Casley, Santa Rosa, CA (US); Ethan Korngold, Portland, OR (US)

(73) Assignee: Medtronic, Inc., Minneapolis, MN (US)

( * ) Notice: Subject to any disclaimer, the term of this patent is extended or adjusted under 35 U.S.C. 154(b) by 185 days.

(21) Appl. No.: 17/187,261

(22) Filed: Feb. 26, 2021

(65) Prior Publication Data
US 2021/0275299 A1  Sep. 9, 2021

Related U.S. Application Data

(60) Provisional application No. 62/985,124, filed on Mar. 4, 2020.

(51) Int. Cl.
A61F 2/24 (2006.01)
(52) U.S. Cl.
CPC .......... *A61F 2/2418* (2013.01); *A61F 2/2433* (2013.01); *A61F 2250/0098* (2013.01)
(58) Field of Classification Search
CPC .................. A61F 2/2418; A61F 2/2433; A61F 2250/0098; A61F 2002/3008;
(Continued)

(56) References Cited

U.S. PATENT DOCUMENTS 6,361,557 B1   3/2002  Gittings et al.
6,574,497 B1   6/2003  Pacetti
(Continued)

FOREIGN PATENT DOCUMENTS

EP     2055266 B1     2/2012
WO     2010031060 A1  3/2010
(Continued)

OTHER PUBLICATIONS

International Search Report and Written Opinion, Application No. PCT/US2021/020676, mailed Jun. 2, 2021.
(Continued)

*Primary Examiner* — Melanie R Tyson
*Assistant Examiner* — Cassidy N Stuhlsatz
(74) *Attorney, Agent, or Firm* — Medler Ferro Woodhouse & Mills PLLC

(57) ABSTRACT

A transcatheter valve prosthesis includes a stent having a crimped configuration for delivery within a vasculature and an expanded configuration for deployment within a native heart valve. The stent includes at least one axial frame member. The transcatheter valve prosthesis includes at least one outflow marker positioned on the at least one axial frame member. The transcatheter heart valve prosthesis may include inflow markers positioned within the inflow portion of the stent. The transcatheter heart valve prosthesis may include two outflow markers disposed on axial frame members and being circumferentially and longitudinally offset from each other. The markers are configured to aid in axial and circumferential aligned of the transcatheter heart valve prosthesis within a native heart valve.

4 Claims, 38 Drawing Sheets

(58) Field of Classification Search
CPC ............ A61F 2250/0096; A61F 2/2427; A61F 2/243; A61F 2/2436; A61F 2/2439; A61B 2090/376; A61B 2090/3966
See application file for complete search history.

(56) References Cited

U.S. PATENT DOCUMENTS

| | | | |
|---|---|---|---|
| 6,935,404 | B2 | 8/2005 | Duerig et al. |
| 7,972,378 | B2 | 7/2011 | Tabor et al. |
| 8,673,000 | B2 | 3/2014 | Tabor et al. |
| 8,998,981 | B2 | 4/2015 | Tuval et al. |
| 9,744,034 | B2 | 8/2017 | Braido et al. |
| 9,839,513 | B2 | 12/2017 | Essinger et al. |
| 10,524,904 | B2 | 1/2020 | O'connell et al. |
| 2003/0114913 | A1* | 6/2003 | Spenser ............... A61F 2/2427 623/2.14 |
| 2006/0235505 | A1* | 10/2006 | Oepen .................. A61F 2/915 623/1.15 |
| 2008/0147118 | A1 | 6/2008 | Ghione et al. |
| 2008/0275540 | A1 | 11/2008 | Wen |
| 2009/0076594 | A1 | 3/2009 | Sabaria |
| 2009/0192591 | A1 | 7/2009 | Ryan et al. |
| 2010/0198346 | A1 | 8/2010 | Keogh et al. |
| 2010/0249908 | A1* | 9/2010 | Chau .................... A61F 2/243 623/1.26 |
| 2011/0022157 | A1* | 1/2011 | Essinger .............. A61F 2/2436 623/1.11 |
| 2013/0058556 | A1* | 3/2013 | Ohishi ................... A61F 2/06 623/1.15 |
| 2013/0325107 | A1* | 12/2013 | Wu ...................... A61F 2/844 623/1.34 |
| 2014/0188219 | A1 | 7/2014 | Conklin et al. |
| 2014/0277389 | A1* | 9/2014 | Braido ................ A61F 2/2418 623/1.26 |
| 2015/0230923 | A1* | 8/2015 | Levi .................... A61F 2/2418 623/2.36 |
| 2016/0296324 | A1* | 10/2016 | Bapat ................... A61F 2/2418 |
| 2018/0221181 | A1 | 8/2018 | Fischer et al. |
| 2018/0344458 | A1 | 12/2018 | Spenser et al. |
| 2019/0117424 | A1* | 4/2019 | Berra ...................... A61F 2/07 |
| 2019/0192275 | A1* | 6/2019 | Kim .................... A61B 90/39 |
| 2019/0247177 | A1* | 8/2019 | Kim ........................ A61F 2/07 |
| 2019/0262507 | A1* | 8/2019 | Adamek-Bowers ......... A61F 2/2418 |
| 2019/0365957 | A1 | 12/2019 | Paquin |
| 2020/0268535 | A1 | 8/2020 | Carpenter et al. |
| 2020/0390575 | A1 | 12/2020 | Guo et al. |

FOREIGN PATENT DOCUMENTS

| | | | | |
|---|---|---|---|---|
| WO | WO-2011137531 | A1 * | 11/2011 | ........... A61F 2/2409 |
| WO | 2014171183 | A1 | 10/2014 | |
| WO | 2016100806 | A1 | 6/2016 | |
| WO | WO-2017103830 | A1 * | 6/2017 | ........... A61F 2/2412 |
| WO | 2021/040547 | A1 | 2/2021 | |
| WO | WO-2021040547 | A1 * | 3/2021 | ........... A61F 2/2418 |

OTHER PUBLICATIONS

International Search Report and Written Opinion, Application No. PCT/2021/047427, mailed Nov. 30, 2021.
Final Office Action, U.S. Appl. No. 17/408,356, dated Mar. 9, 2023.

* cited by examiner

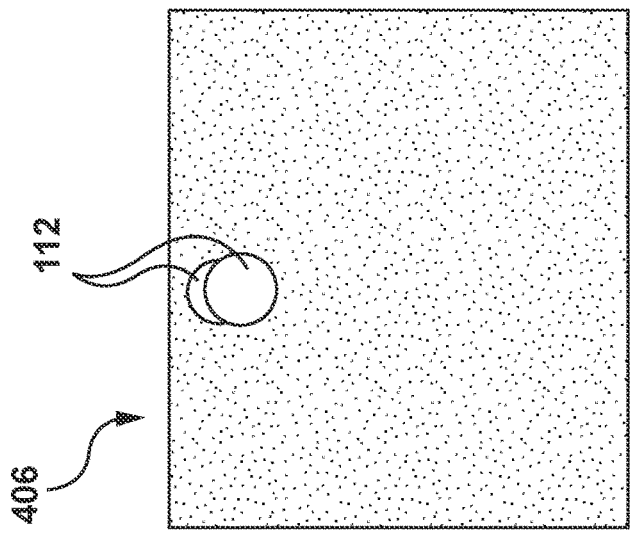
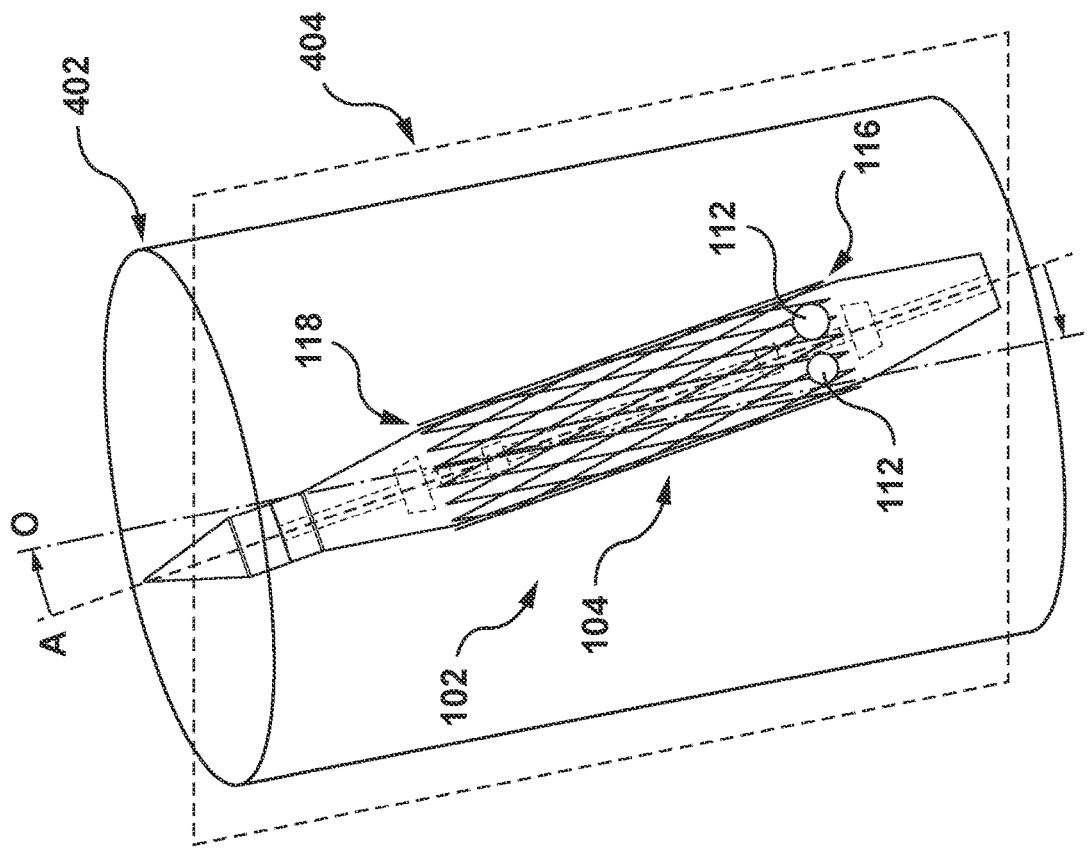
FIG. 4E
FIG. 4D

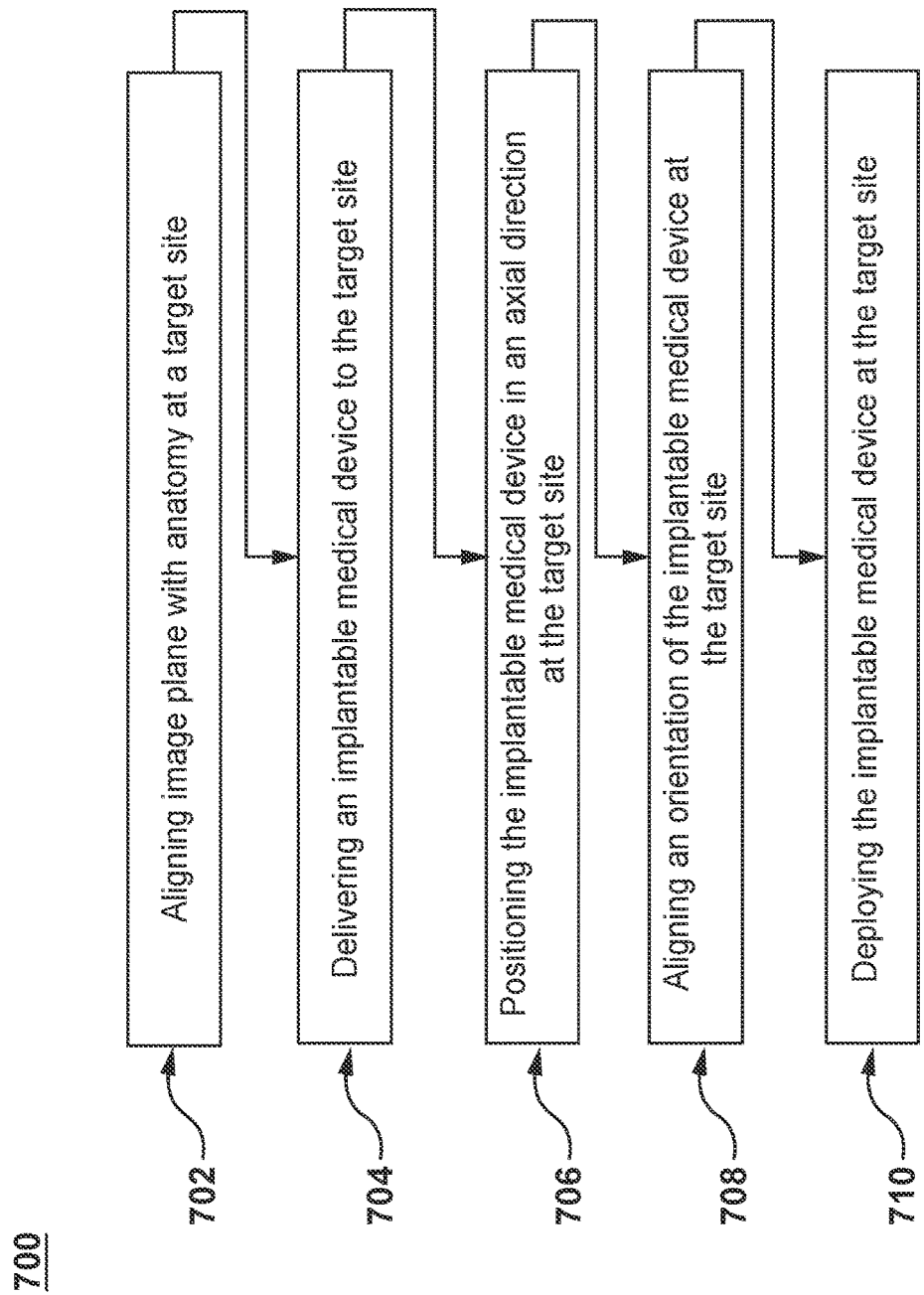

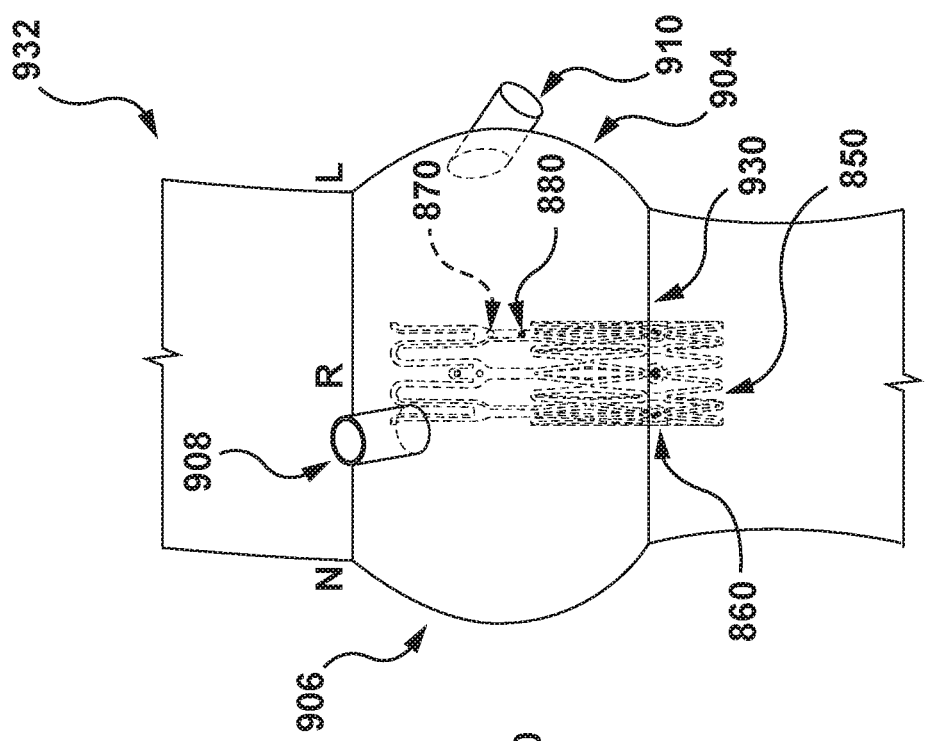
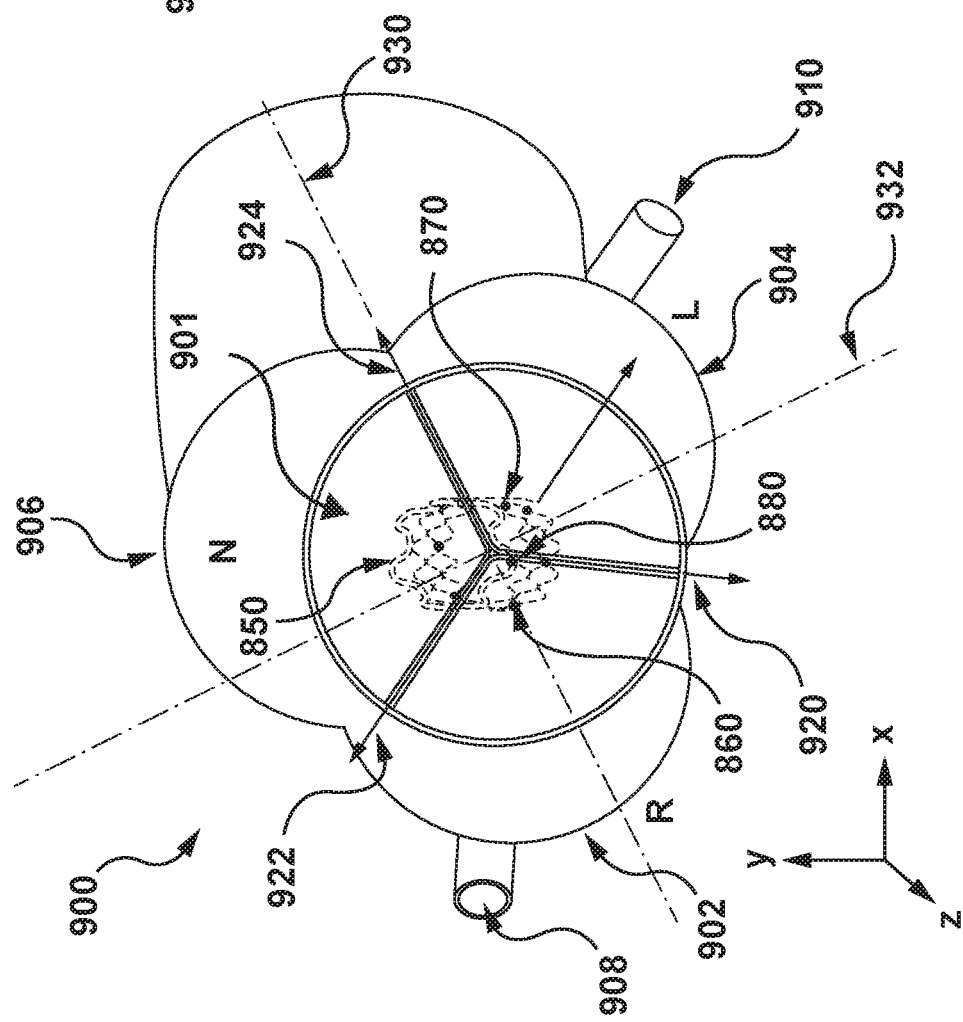
FIG. 11B
FIG. 11A

DEVICES AND METHODS FOR MULTI-ALIGNMENT OF IMPLANTABLE MEDICAL DEVICES

CROSS-REFERENCE TO RELATED APPLICATIONS

This application claims the benefit under 35 U.S.C. § 119(e) of the filing dated of U.S. Provisional Application No. 62/985,124, filed Mar. 4, 2020, the contents of which are incorporated by reference herein in their entirety.

FIELD

The present technology is generally related to medical devices.

BACKGROUND

Currently, implantable medical devices, such as large stents, scaffolds, and other cardiac intervention devices are utilized to repair or replace problem native biological systems. For example, heart valve replacement in patients with severe valve disease is a common surgical procedure. The replacement can conventionally be performed by open heart surgery, in which the heart is usually arrested and the patient is placed on a heart bypass machine. In recent years, prosthetic heart valves have been developed which are implanted using minimally invasive procedures such as transapical or percutaneous approaches. These procedures involve compressing the prosthetic heart valve radially to reduce its diameter, inserting the prosthetic heart valve into a delivery device, such as a catheter, and advancing the delivery device to the correct anatomical position in the heart. Once properly positioned, the prosthetic heart valve is deployed by radial expansion within the native valve annulus.

While these procedures are substantially less invasive than open heart surgery, the lack of line-of-sight visualization of the prosthetic heart valve and the native valve presents challenges, because the physician cannot see the actual orientation of the prosthetic heart valve during the implantation procedure. Correct positioning of the prosthetic heart valve is achieved using radiographic imaging, which yields a two-dimensional image of the viewed area. The physician must interpret the image correctly in order to properly place the prosthetic heart valve in the desired position. Failure to properly position the prosthetic heart valve sometimes leads to migration of the prosthetic heart valve or to improper functioning. Proper placement of the prosthetic heart valve using radiographic imaging is thus critical to the success of the implantation.

SUMMARY

The techniques of this disclosure generally relate to a delivery system for delivering and installing an implantable medical device at an implant location (e.g., target site). The delivery system utilizes a combination of alignment markers and implant markers that provide a visual indication of both an axial position of the implantable medical device and an orientation of the implantable medical device (e.g., tilt, rotation, etc.). The combination of alignment markers and implant markers allow an operator of the delivery system to pinpoint the deployed location of the implantable medical device at the target site.

The techniques of this disclosure are further generally related to an implantable medical device includes implant markers to aid in axial and circumferential alignment of the implantable medical device within a native heart valve.

In one aspect of the present disclosure, a transcatheter valve prosthesis includes: a stent having a crimped configuration for delivery within a vasculature and an expanded configuration for deployment within a native heart valve, wherein the stent comprises an inflow portion and at least one axial frame member: at least one inflow marker positioned within the inflow portion of the stent: and at least one outflow marker positioned on the at least one axial frame member, wherein the inflow marker and the outflow marker are visible relative to the stent in one or more images captured during delivery and deployment of the stent.

In another aspect of the disclosure, in combination with any of the other aspects, the inflow portion comprises at least two rows of struts.

In another aspect of the disclosure, in combination with any of the other aspects, the at least one inflow marker is positioned at an intersection between two pairs of struts from the at least two rows of struts.

In another aspect of the disclosure, in combination with any of the other aspects, the at least one inflow marker comprises six inflow markers positioned at distinct locations around a circumference of the stent at an intersection between two pairs of struts from the at least two rows of struts.

In another aspect of the disclosure, in combination with any of the other aspects, the at least one inflow marker is configured to align the stent with a native valve annulus.

In another aspect of the disclosure, in combination with any of the other aspects, the at least one axial frame member comprises at least one commissure post, and wherein the at least one outflow marker is positioned on the at least one commissure post.

In another aspect of the disclosure, in combination with any of the other aspects, the at least one outflow marker is configured to be aligned with a native commissure of the native heart valve.

In another aspect of the disclosure, in combination with any of the other aspects, the at least one axial frame member comprises at least one commissure post and at least one axial strut disposed adjacent the at least one commissure post, the at least one outflow marker comprises a first outflow marker and a second outflow marker, the first outflow marker positioned on the commissure post and the second outflow marker positioned on the axial strut, and one of the first outflow marker and the second outflow marker is positioned closer to an outflow end of the stent relative to the other of the first outflow marker and the second outflow marker.

In another aspect of the disclosure, in combination with any of the other aspects, the first outflow marker and the second outflow marker are positioned such that, in an image plane parallel to an annulus of the native heart valve and bisecting a right coronary cusp of the native heart valve, if the first outflow marker and the second outflow marker appear with no radial offset, the transcatheter valve prosthesis is properly rotationally aligned.

In another aspect of the disclosure, in combination with any of the other aspects, the first outflow maker and the second outflow marker are offset by sixty degrees circumferentially.

In another aspect of the disclosure, in combination with any of the other aspects, the at least one inflow marker and the at least one outflow marker are circumferentially aligned on the stent.

In another aspect of the disclosure, in combination with any of the other aspects, the stent is balloon expandable.

In another aspect of the present disclosure, a transcatheter valve prosthesis comprises: a stent having a crimped configuration for delivery within a vasculature and an expanded configuration for deployment within a native heart valve, wherein the stent comprises an inflow portion and at least one axial frame member: and at least one outflow marker positioned on the at least one axial frame member, wherein the outflow marker is visible relative to the stent in one or more images captured during delivery and deployment of the stent.

In another aspect of the disclosure, in combination with any of the other aspects, the at least one axial frame member comprises at least one commissure post, and the at least one outflow marker is positioned on the at least one commissure post.

In another aspect of the disclosure, in combination with any of the other aspects, the at least one outflow marker is configured to be aligned with a native commissure of the native heart valve.

In another aspect of the disclosure, in combination with any of the other aspects, the at least one axial frame member comprises at least one commissure post and at least one axial strut disposed adjacent the at least one commissure post, the at least one outflow marker comprises a first outflow marker and a second outflow marker, the first outflow marker positioned on the commissure post and the second outflow marker positioned on the axial strut, and one of the first outflow marker and the second outflow marker is positioned closer to an outflow end of the stent relative to the other of the first outflow marker and the second outflow marker.

In another aspect of the disclosure, in combination with any of the other aspects, the first outflow marker and the second outflow marker are positioned such that, in an image plane parallel to an annulus of the native heart valve and bisecting a right coronary cusp of the native heart valve, if the first outflow marker and the second outflow marker appear with no radial offset, the transcatheter valve prosthesis is properly rotationally aligned.

In another aspect of the disclosure, in combination with any of the other aspects, the first outflow maker and the second outflow marker are offset by sixty degrees circumferentially.

In another aspect of the disclosure, a method for rotationally orienting a transcatheter valve prosthesis includes: delivering the transcatheter valve prosthesis in a crimped configuration to a target site at a native heart valve, the transcatheter valve prosthesis including a stent comprising an inflow portion, an outflow portion, at least one axial frame member coupling the inflow portion to the outflow portion, and at least one outflow marker positioned on the at least one axial frame member: receiving fluoroscopic image in a selected image plane: determining, based on the image in the selected image plane and the at least one outflow marker, whether the transcatheter heart valve prosthesis is in a desired rotational orientation.

In another aspect of the present disclosure, a delivery system for a medical procedure includes a shaft configured to deliver an implantable medical device for installation at an implant location. The system includes a proximal alignment marker coupled to the shaft. The proximal alignment marker is positioned on the shaft at a first location that corresponds to a proximal end of the implantable medical device when in the radially expanded state. The system also includes a distal alignment marker coupled to the shaft. The distal alignment marker is positioned on the shaft at a second location that corresponds to a distal end of the implantable medical device when in the radially expanded state. Additionally, the system includes one or more implant markers configured to be positioned on the implantable medical device. One or more of the proximal alignment marker, the distal alignment marker, and the one or more implant markers are visible in one or more images captured during the installation at the implant location. At least one of a shape of the one or more implant markers or a position of the one or more implant markers produces a visual reference in the one or more images for orienting the implantable medical device relative to a desired orientation at a target site.

In another aspect of the disclosure, in combination with any of the other aspects, the visual reference in the one or more images indicates one or more of a tilt of a central axis of the implantable medical device or a rotation of the implantable medical device about the central axis.

In another aspect of the disclosure, in combination with any of the other aspects, the one or more implant markers comprises a plurality of implant markers positioned on the implantable medical device in a plane that is perpendicular to a central axis of the implantable medical device, wherein a predetermined pattern of the plurality of implant markers is visible in the one or more images when the central axis the implantable medical device is aligned with a desired orientation axis at the target site.

In another aspect of the disclosure, in combination with any of the other aspects, the one or more implant markers comprises a first implant marker positioned on the implantable medical device, and a second implant marker positioned on the implantable medical device, wherein the implantable medical device is aligned with a desired orientation axis when an image of the first implant marker is visible and obscures an image of the second implant marker.

In another aspect of the disclosure, in combination with any of the other aspects, the one or more implant markers comprises a three-dimensional (3D) implant marker, a side of the 3D implant marker being positioned on the implantable medical in a plane that is perpendicular to a central axis of the implantable medical device, wherein a first two-dimensional (2D) image of the single implant marker is visible in the one or more images when the central axis of the implantable medical device is aligned with a desired orientation axis at the target site, and a second 2D image of the single implant marker, different from the first 2D image, is visible in the one or more images when the central axis of the implantable medical device is not aligned with the desired orientation axis.

In another aspect of the disclosure, in combination with any of the other aspects, the one or more proximal alignment markers, the one or more distal alignment markers, and the one or more implant markers comprise radiopaque materials.

In another aspect of the disclosure, in combination with any of the other aspects, a shape of one or more of the one or more proximal alignment markers, the one or more distal alignment markers, and the one or more implant markers comprises a pin, a dot, a circle, an oval, a sphere, a triangle, a cone, a square, a cube, a bar, a band, a ring, and a cross.

In another aspect of the disclosure, in combination with any of the other aspects, the implantable medical device further includes a medical implant and a frame configured to support the medical implant and configured to secure the medical implant at the target site.

In another aspect of the disclosure, in combination with any of the other aspects, the shaft comprises an expansion device that causes the implantable medical device to transition from a compressed state to a radially expanded state.

In another aspect of the disclosure, a delivery system for a medical procedure includes: a shaft configured to deliver an implantable medical device for installation at a target site: and at least one implant marker configured to be positioned on the implantable medical device, wherein: one or more the at least one implant marker is visible in one or more images captured during the installation at the target site, at least one of a shape of the at least one implant marker and a position of the at least one implant marker produces a visual reference in the one or more images for orienting the implantable medical device, and the visual reference provides a verification that a central axis of the implantable medical device is aligned with a desired orientation axis at the target site.

In another aspect of the disclosure, and in combination with any of the other aspects, the visual reference in the one or more images indicates one or more of a tilt of the central axis of the implantable medical device or a rotation of the implantable medical device about the central axis.

In another aspect of the disclosure, and in combination with any of the other aspects, the at least one implant marker comprises a plurality of implant markers positioned on the implantable medical device in a plane that is perpendicular to the central axis of the implantable medical device, wherein a predetermined pattern of the plurality of implant markers is visible in the one or more images when the central axis the implantable medical device is aligned with the desired orientation axis at the target site.

In another aspect of the disclosure, and in combination with any of the other aspects, the at least one implant markers comprises: a first implant marker positioned on the implantable medical device: and a second implant marker positioned on the implantable medical device, wherein the implantable medical device is aligned with the desired orientation axis when an image of the first implant marker is visible and obscures an image of the second implant marker.

In another aspect of the disclosure, and in combination with any of the other aspects, the at least one implant marker comprises: a three-dimensional (3D) implant marker, a side of the 3D implant marker being positioned on the implantable medical in a plane that is perpendicular to the central axis of the implantable medical device, wherein: a first two-dimensional (2D) image of the single implant marker is visible in the one or more images when the central axis of the implantable medical device is aligned with a desired orientation axis at the target site, and a second 2D image of the single implant marker, different from the first 2D image, is visible in the one or more images when the central axis of the implantable medical device is not aligned with the desired orientation axis.

In another aspect of the disclosure, and in combination with any of the other aspects, the delivery system further comprises: one or more proximal alignment markers coupled to the shaft, wherein the one or more proximal alignment markers are positioned on the shaft at a first location that corresponds to a proximal end of the implantable medical device when in the radially expanded state: and one or more distal alignment markers coupled to the shaft, wherein the one or more distal alignment markers are positioned on the shaft at a second location that corresponds to a distal end of the implantable medical device when in the radially expanded state.

In another aspect of the disclosure, and in combination with any of the other aspects, the one or more proximal alignment markers, the one or more distal alignment markers, and the one or more implant markers comprise radiopaque materials.

In another aspect of the disclosure, and in combination with any of the other aspects, a shape of one or more of the proximal alignment marker, the distal alignment marker, and the one or more implant markers comprises a pin, a dot, a circle, an oval, a sphere, a triangle, a cone, a square, a cube, a bar, a band, a ring, and a cross.

In another aspect of the disclosure, and in combination with any of the other aspects, the implantable medical device comprises a medical implant and a frame configured to support the medical implant and configured to secure the medical implant at the implant location.

In another aspect of the disclosure, a delivery system for a medical procedure includes: a shaft configured to deliver an implantable medical device for installation at a target site: one or more proximal alignment markers coupled to the shaft, wherein the one or more proximal alignment markers is positioned on the shaft at a first location that corresponds to a proximal end of the implantable medical device when in the radially expanded state: and one or more distal alignment markers coupled to the shaft, wherein the one or more distal alignment markers are positioned on the shaft at a second location that corresponds to a distal end of the implantable medical device when in the radially expanded state, wherein: one or more of the proximal alignment markers and the one or more distal alignment markers are visible in one or more images captured during the installation at the target site, and the one or more proximal alignment markers and the one or more distal alignment markers provide a visual reference in the one or more images for positioning the implantable medical device along an annular direction.

In another aspect of the disclosure, and in combination with any of the other aspects, the one or more proximal alignment markers, the one or more distal alignment markers, and the one or more implant markers comprise radiopaque materials.

In another aspect of the disclosure, and in combination with any of the other aspects, a shape of one or more of the one or more proximal alignment markers, the one or more distal alignment markers, and the one or more implant markers comprises a pin, a dot, a circle, an oval, a sphere, a cone, a triangle, a cube, a square, a bar, a band, a ring, and a cross.

In another aspect of the disclosure, and in combination with any of the other aspects, the shaft comprises an expansion device that causes the implantable medical device to transition from a compressed state to a radially expanded state.

In another aspect of the disclosure, and in combination with any of the other aspects, the shaft comprises an expansion device that causes the implantable medical device to transition from a compressed state to a radially expanded state.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings are not to scale.

FIGS. 4A-4G depict several views of another arrangement of implant markers of the delivery system of FIGS. 1A and 1B in accordance with an embodiment hereof.

FIG. 7 depicts a flow of a method for operating of the delivery system of the delivery system of FIGS. 1A and 1B in accordance with an embodiment hereof.

FIGS. 11A-11D illustrate various views of a target site for the transcatheter valve prosthesis of FIGS. 10A-10C in accordance with an embodiment hereof.

DETAILED DESCRIPTION

Specific embodiments of the present disclosure are now described with reference to the figures, wherein like reference numbers indicate identical or functionally similar elements.

The following detailed description describes examples of embodiments and is not intended to limit the present technology or the application and uses of the present technology. Although the description of embodiments hereof is in the context of implantable medical devices, the present technology may also be used in other devices. Furthermore, there is no intention to be bound by any expressed or implied theory presented in the preceding technical field, background, brief summary or the following detailed description.

The terms "distal" and "proximal", when used in the following description to refer to a delivery system or catheter are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a device to be implanted into a vessel, such as a heart valve prosthesis, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

Embodiments of disclosed herein are directed to a delivery system for delivering and implanting an implantable medical device at an implantation location. In embodiments, the delivery system utilizes multiple markers for positioning and orienting the implantable medical device. The delivery system utilizes alignment markers that correspond to an axial position of end of the implantable medical device when in a radially expanded. The delivery system also utilizes implant markers that assist in the orientation of the implantable medical device. The implant markers are positioned on the implantable medical device such that the implant markers provide a visual indication that the implantable medical device is properly oriented. The alignment markers and the implant markers can include radiopaque materials that are visible on radiographic imaging systems.

Figure 1A:
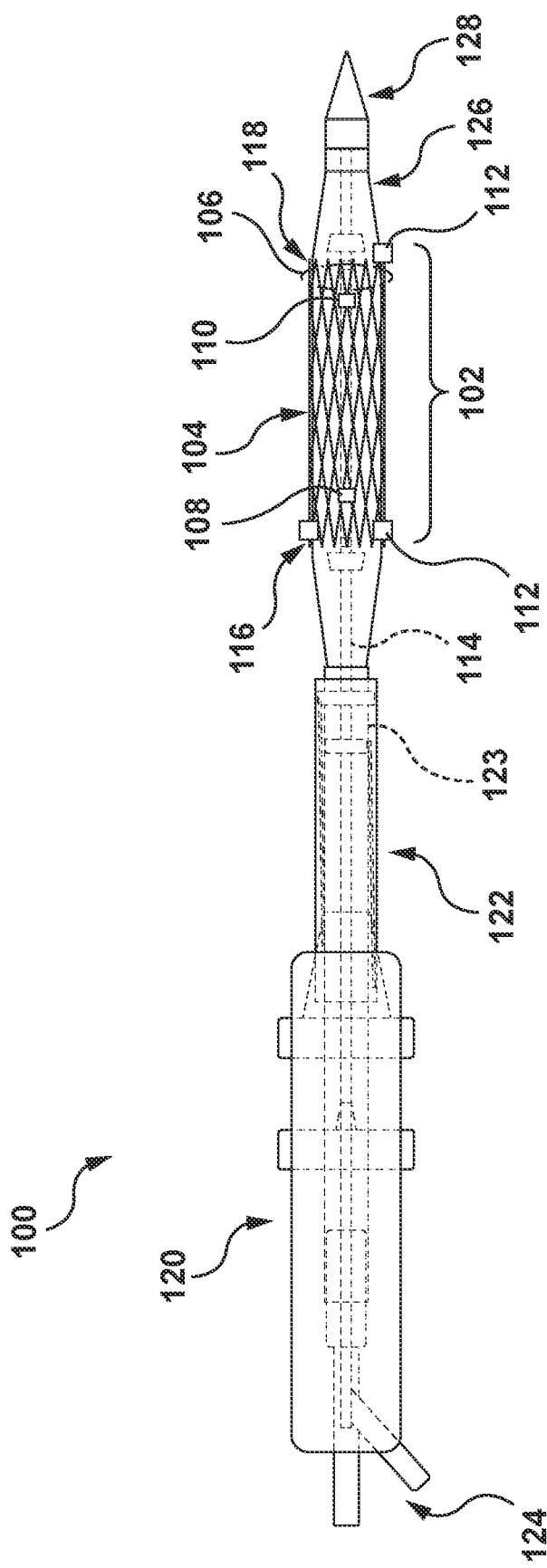
FIG. 1A depicts a perspective illustration of a delivery system for use with a medical device in a compressed state in accordance with an embodiment hereof.
Figure 1B:
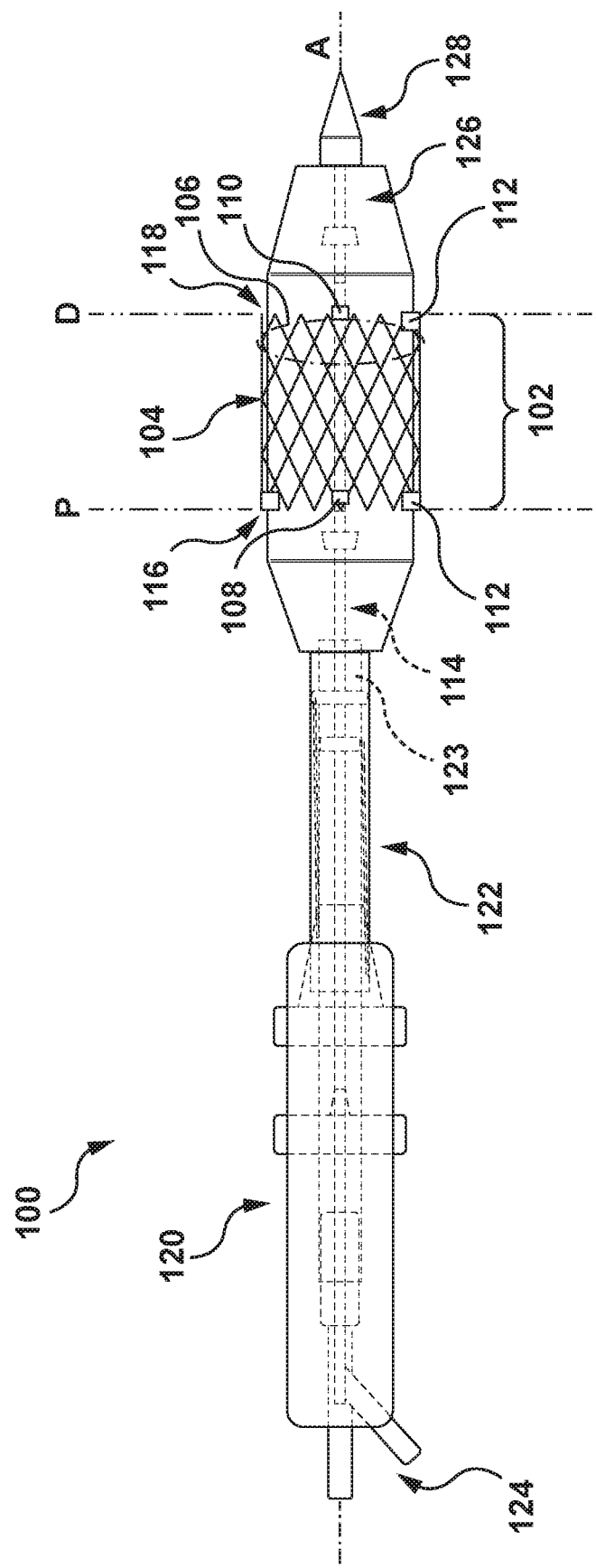
FIG. 1B depicts a perspective illustration of the delivery system of FIG. 1A with the medical device in a radially expanded state in accordance with an embodiment hereof.

FIGS. 1A and 1B illustrate an example of a delivery system 100 in accordance with an embodiment hereof. One skilled in the art will realize that FIGS. 1A and 1B illustrate one example of a delivery system and that existing components illustrated in FIGS. 1A and 1B may be removed and/or additional components may be added to the delivery system 100.

As illustrated in FIG. 1A, the delivery system 100 is configured to deliver and install an implantable medical device 102 at an implantation location (e.g., target site) in a patient. In embodiments, the implantable medical device 102 includes a frame 104 and a medical implant 106. For example, the implantable medical device 102 can include a frame and/or stent as the frame 104 and a replacement heart valve as the medical implant 106.

In embodiments, the frame 104 of the implantable medical device 102 can be generally tubular, and is self-expandable, balloon expandable, or mechanically expandable, having an unexpanded or crimped configuration for delivery through internal anatomy of a patient (e.g., within a vasculature) and a radially expanded configuration for deployment within a target site or anatomical structure, (e.g., a native heart valve). The frame 104 can be configured as a unitary frame or scaffold that supports the medical implant 106. For example, when the implantable medical device 102 is deployed within a valve annulus of a native heart valve, the frame 104 of the implantable medical device 102 is configured to be radially expanded within native valve leaflets of the patient's defective valve, to thereby retain the native valve leaflets in a permanently open state. In this example, the frame 104 of the implantable medical device 102 supports the medical implant 106, e.g., replacement heart valve, including one or more valve leaflets of the replacement heart valve within an interior of the frame 104.

In embodiments, the implantable medical device 102 needs to be properly aligned and positioned at the target site of the patient. As illustrated in FIGS. 1A-IE, to assist with proper alignment and positioning, the delivery system 100 includes one or more alignment markers, e.g., one or more proximal alignment markers 108 and one or more distal alignment markers 110. The delivery system 100 also includes one or more implant markers 112. Proximal alignment markers 108, the distal alignment markers 110, and the implant markers 112 include radiopaque or other material that allow the proximal alignment markers 108, the distal alignment markers 110, and the implant markers 112 to be detected and/or viewed during the installation of the implantable medical device 102.

As described herein, radiopacity refers to the relative inability of electromagnetic radiation, particularly X-rays, to pass through a particular material. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc. Due to the radiopacity, the proximal alignment markers 108, the distal alignment markers 110, and the implant markers 112 create visibility reference points in images during the installation of the implantable medical device 102 that assist with the positioning and alignment of the implantable medical device. In embodiments, the images may be taken using fluoroscopy and/or other imaging techniques, e.g., computed tomography (CT), magnetic resonance (MRI), etc.

In embodiments, as illustrated in FIG. 1B, the proximal alignment marker 108 and the distal alignment marker 110 are positioned on an inner shaft 114 of the delivery system 100. The proximal alignment marker 108 and the distal alignment marker 110 are configured to provide a visual alignment reference for aligning the implantable medical device 102 in an axial direction along a central axis, A. The proximal alignment marker 108 and the distal alignment marker 110 can be positioned at a location that indicates an expanded location of a proximal end 116 and a distal end 118 of the frame 104. That is, the proximal alignment marker 108 and the distal alignment marker 110 can provide a visual reference in one or more images taken during installation (e.g., fluoroscopy and/or other imaging techniques) of the relative positioning, in the axial direction along the central axis, A, of the implantable medical device 102 when expanded.

As illustrated in FIG. 1B, when the frame 104 is fully expanded, the proximal alignment marker 108 indicates a relative position, P, of the proximal end 116 in the axial direction along the central axis, A. Likewise, the distal alignment marker 110 indicates a relative position, D, of the distal end 118 in the axial direction along the central axis, A. The proximal alignment marker 108 and the distal alignment marker 110 can be utilized as visual reference points to align the implantable medical device 102 in the axial direction along the central axis, A, to ensure the implantable medical device 102 is properly positioned axially prior to expansion (i.e., to ensure proper depth of the implantable medical device 102). Using the visual reference points, an operator of the delivery device 100 can position the implantable medical device 102 to ensure the implantable medical device 102 properly engages with native structure of at the target site once the frame 104 is expanded.

For example, if the implantable medical device 102 includes a replacement valve, the proximal alignment marker 108 and the distal alignment marker 110 can be utilized to ensure the proximal end 116 of the frame 104 engages native tissue at the target site, such as the native annulus, and the distal end 118 engages the leaflets of the native heart valve. As such, the operator of the implantable medical device is not required to estimate the final location of the implantable medical device 102 once expanded. Likewise, for example, by indicating the radially expanded location of the proximal end 116 and the distal end 118, the implantable medical device 102 can be positioned in customized locations depending on the anatomy of the patient.

In embodiments, the proximal alignment marker 108 and the distal alignment marker 110 can be configured in any shape and size to accommodate the installation of the implantable medical device 102. For example, the proximal alignment markers 108 and distal alignment markers 110 can be formed in any 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the proximal alignment markers 108 and distal alignment markers 110 may be provided to provide a benefit for a given application.

In embodiments, the implant markers 112 are positioned at various locations of the implantable medical device 102 to provide a guide for orienting the implantable medical device 102. The implant markers 112 operate solely or in combination to provide visual references to an orientation of the implantable medical device 102 relative to the native structure of the target site of the implantable medical device 102 is being installed. As described herein, the orientation refers to the three-dimensional positioning (e.g., rotation, tilt, radial positioning, etc.) within the anatomy of the target site, (e.g., annulus of a vasculature structure and heart valve). In embodiments, the orientation can include a tilt of the implantable medical device 102, e.g., an angle of the central axis, A, relative to the anatomy of the target site, (e.g., annulus of a vasculature structure and heart valve). In embodiment, the orientation can include a rotation of the implantable medical device 102. e.g., rotational position of various components of the implantable medical device 102 about the central axis, A, relative to the anatomy of the target site, (e.g., annulus of a vasculature structure and heart valve). In embodiment, the orientation can include a radial positioning of the implantable medical device, e.g., a distance between the implantable medical device 102 and portions of the anatomy of the target site, (e.g., annulus of a vasculature structure and heart valve).

As further described below in FIGS. 3A-3G, 4A-4G, 5A-5B, and 6A-6B, the implant markers 112 can be configured in any shape and size to accommodate the installation of the implantable medical device 102. For example, the implant markers 112 can be pins, dots, circles, ovals, spheres, triangles, cones, squares, cubes, bars, crosses, bands, rings, and combination thereof. One skilled in the art will realize that other configurations and shapes of the implant markers 112 may be provided to provide a benefit for a given application.

Returning to in FIG. 1A, the delivery system 100 includes components and hardware that enable an operator to deliver the implantable medical device 102 through the internal anatomy of a patient to a target site and deploy the implantable medical device 102. The delivery system 100 includes a handle assembly 120 and a support shaft assembly 122. The support shaft assembly 122 can include a lumen 123 for receiving the inner shaft 114 and the implantable medical device 102 and from which the inner shaft 114 can extend. The inner shaft 114 can include a guidewire lumen (not shown) from which a guidewire can extend for guiding the medical device 102 to the target site. The inner shaft can include a tip 128 coupled to the distal end of the inner shaft 114.

The handle assembly 120 can include one or more implant expansion controls 124 (e.g., including one or more levers, knobs, switches, and/or valves) for controllably expanding implantable medical device 102 from a crimped configuration for delivery through internal anatomy of a patient (e.g., within a vasculature) to a radially expanded configuration for deployment within a target site or anatomical structure, (e.g., a native heart valve). The delivery system can include an expansion device 126 coupled to the inner shaft 114 and operatively coupled to the expansion controls 124. The expansion device 126 can be configured to control expansion of the implantable medical device 102 from a compressed state to a radially expanded state when positioned at the target site. For example, in some embodiments, the expansion device 126 can be a dilatation balloon that can be controllably inflated via an inflation lumen (not shown) fluidly coupled to the expansion controls 124 to controllably expand a balloon expandable implantable medical device 102.

Figure 1C:
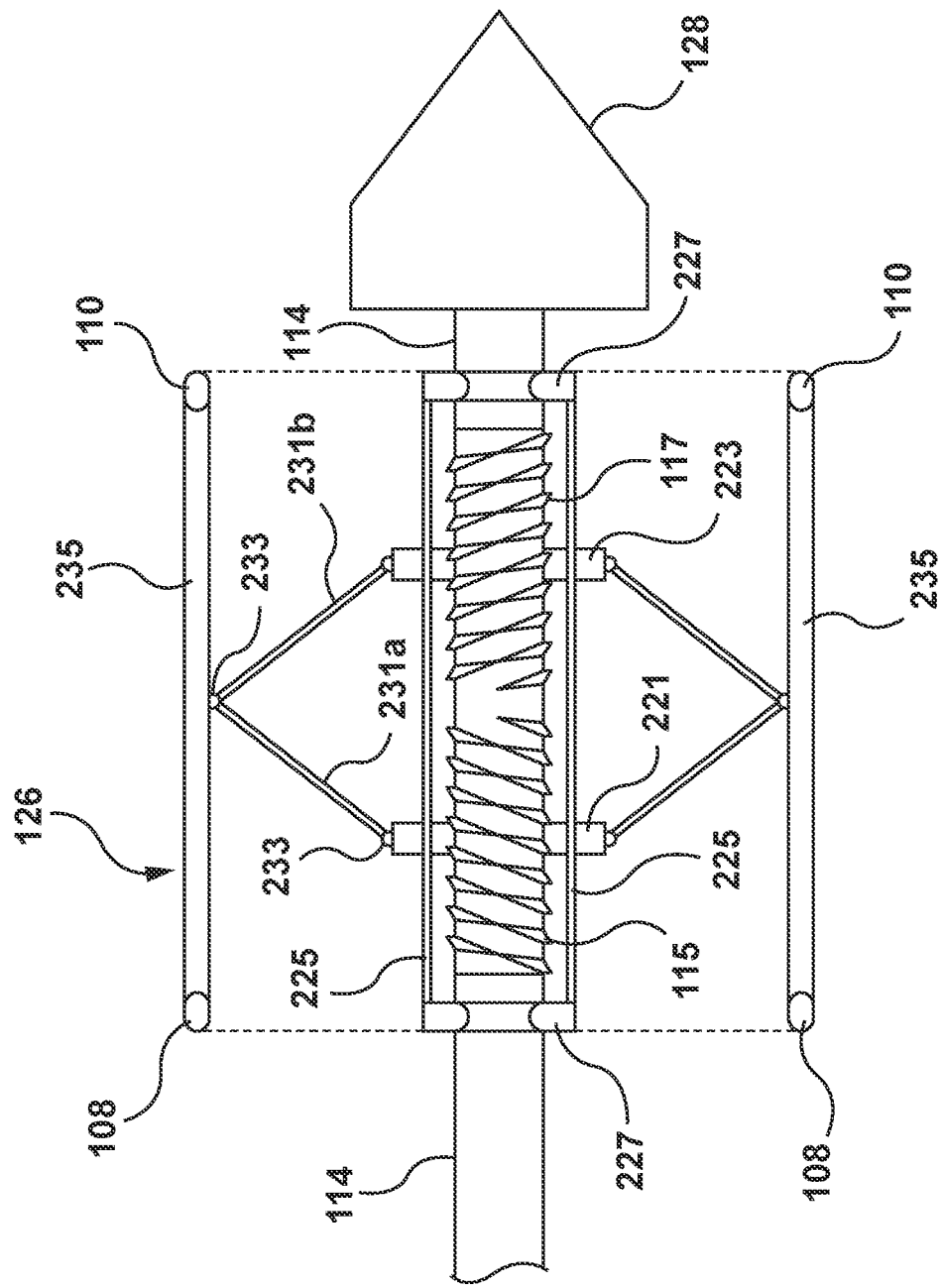
FIG. 1C depicts a perspective illustration of another delivery system for use with a medical device in a radially expanded state in accordance with an embodiment hereof.

In some embodiments, the expansion device 126 can be a mechanical expansion device (as shown in FIG. 1C) that can be mechanically coupled via one or more elongate members (e.g., push rods, pull wires, and/or an inner shaft) to the expansion controls 124 to controllably expand a mechanically expandable implantable medical device 102. In some embodiments, distal end portion of inner shaft 114 can include discontinuous opposite threads 115 and 117 on outer surface of inner shaft 114. A pair of nuts 221, 223 are mounted on inner shaft 114, wherein the first nut 221 is mounted on threads 115 and the second nut 117 is mounted on threads 223. Axial rotation of inner shaft 114 causes first and second nuts, which are prevented from rotating therewith, to travel towards one another or apart from one another depending on the direction of rotation of inner shaft 114. One or more elongate pins or rods 225 extending through one or more holes of nuts 221, 223 prevent nuts 221, 223 from rotating about inner shaft 114 while inner shaft 114 is rotated. Both ends of the elongate pins or rods 225 are fixed to a pair of washers 227. The washers are mounted to inner shaft 114 such that inner shaft 114 may rotate while the washers remain relatively motionless. Expansion device 126 shown in FIG. 1C is in a semi-expanded position. Expansion device 126 can include a plurality of spokes 231 and joints or pivots 233. Pivots 233 can flexibly or rotatably couple a pair of spokes 231a, 231b together and/or pivots 233 can flexibly or rotatably couple a spoke to a nut. In some embodiments, a first end of spoke 231a is coupled to nut 221 via a first pivot 233 and a second end of spoke 231a is coupled to a first end of spoke 231b via a second pivot 233 and the second end of spoke 231b is coupled to nut 223 via a third pivot 233. Pivots 233 coupling a pair of spokes together can be coupled to elongate member 235. In some embodiments, expansion device 126 may comprise any number of pairs of spokes, e.g., 2 pairs, 3 pairs, 4 pairs, 5 pairs, etc. In some embodiments, elongate member 235 may be a flexible tubular member, which forms a continuous radially expanding surface when nuts 221,223 are brought together. In some embodiments, elongate member 235 may comprise one or more flexible or expandable axial members. In some embodiments, elongate member 235 may comprise one or more longitudinal members. In some embodiments, elongate member 235 is sufficiently rigid to radially expand a mechanically expandable implantable medical device 102 when inner shaft 114 is rotated. In some embodiments, as illustrated in FIG. 1C, one or more proximal alignment markers 108 and one or more distal alignment markers 110 can be positioned on the expansion device 126 of the delivery system 100.

Figure 1D:
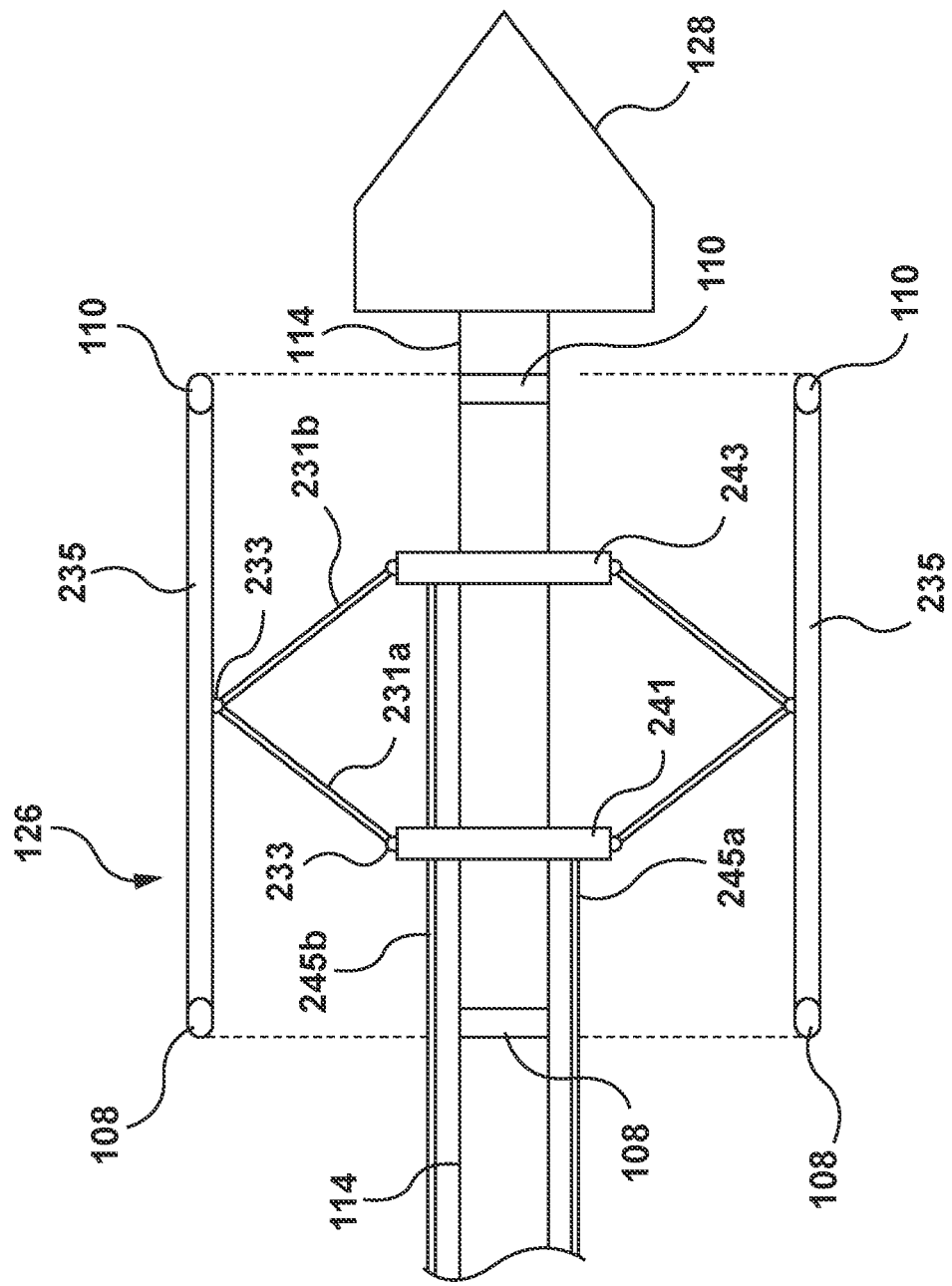
FIG. 1D depicts a perspective illustration of another delivery system for use with a medical device in a radially expanded state in accordance with an embodiment hereof.

In some embodiments, the expansion device 126 can be a mechanical expansion device (as shown in FIG. 1D) that can be mechanically coupled via one or more elongate members (e.g., push rods, pull wires, and/or an inner shaft) to the expansion controls 124 to controllably expand a mechanically expandable implantable medical device 102. In some embodiments, a pair of washers 241, 243 are movably mounted on inner shaft 114. One or more elongate wires or rods 245 extend from the washers 241, 243 to the expansion controls 124 so that longitudinal movement of elongate members 245 proximally and distally or back and forth moves washers 241, 243 toward one another or apart from one another depending on direction of movement of the one or more elongate members 245. For example, a first elongate member 245a is coupled to washer 241 and a second elongate member 245b is coupled to washer 243. Expansion device 126 shown in FIG. 1D is in a semi-expanded position. Expansion device 126 can include a plurality of spokes 231 and joints or pivots 233. Pivots 233 can flexibly or rotatably couple a pair of spokes 231a, 231b together and/or pivots 233 can flexibly or rotatably couple a spoke to a washer. In some embodiments, a first end of spoke 231a is coupled to washer 241 via a first pivot 233 and a second end of spoke 231a is coupled to a first end of spoke 231b via a second pivot 233 and the second end of spoke 231b is coupled to washer 243 via a third pivot 233. Pivots 233 coupling a pair of spokes together can be coupled to elongate member 235. In some embodiments, expansion device 126 may comprise any number of pairs of spokes, e.g., 2 pairs, 3 pairs, 4 pairs, 5 pairs, etc. In some embodiments, elongate member 235 may be a flexible tubular member, which forms a continuous radially expanding surface when washers 241, 243 are brought together. In some embodiments, elongate member 235 may comprise one or more flexible or expandable axial members. In some embodiments, elongate member 235 may comprise one or more longitudinal members. In some embodiments, elongate member 235 is sufficiently rigid to radially expand a mechanically expandable implantable medical device 102 when washers 241, 243 are brought together or moved towards one another. In some embodiments, as illustrated in FIG. 1D, one or more proximal alignment markers 108 and one or more distal alignment markers 110 can be positioned on the expansion device 126 and/or an inner shaft 114, e.g., one or more bands or rings encircling inner shaft 114, of the delivery system 100.

Figure 1E:
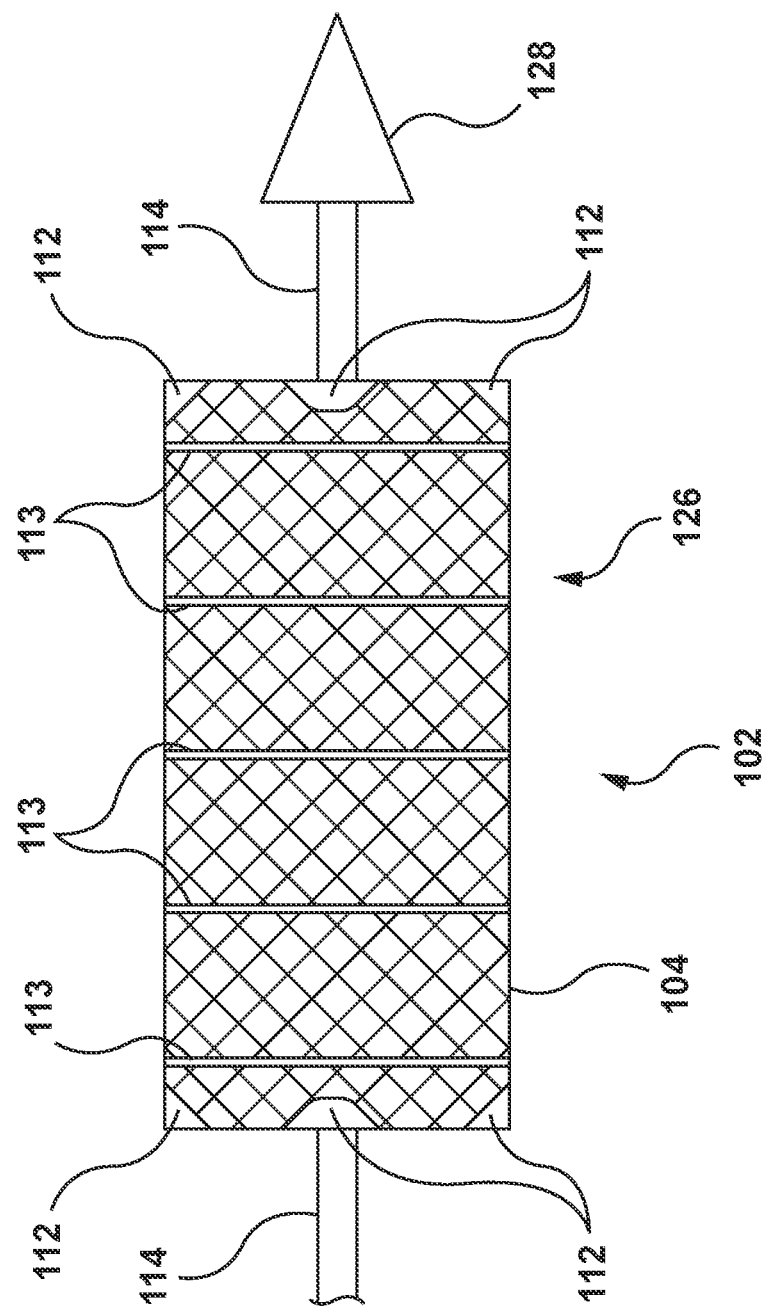
FIG. 1E depicts a perspective illustration of another delivery system for use with a medical device in a radially expanded state in accordance with an embodiment hereof.

In some embodiments, the expansion device 126 can be a device utilizing the expansion controls 124 to control the expansion of a self-expandable implantable medical device 102. In some embodiments, for example, as disclosed in U.S Patent Publication Nos. US2018/0256331 and US2018/0256332, the entire teachings of which are incorporated herein by reference, the expansion device 126 can include one or more elongate tension members 113, e.g., wires, bands, sutures or the like, which extend around the self-expandable implantable medical device 102 (as shown in FIG. 1E) and proximately to expansion controls 124. Compression and expansion of the implantable medical device 102 can be adjusted by adjusting tension in the tension members to permit the implantable medical device 102 to compress, self-expand, and ultimately release from the inner shaft 114. While FIGS. 1A-1E describe components that can be included in the delivery system 100, one skilled in the art will realize the delivery system 100 can include other components to assist with the delivery and installation of the implantable medical device 102.

In embodiments, the implantable medical device 102 can be compressible from a radially expanded or uncompressed state (as shown in FIGS. 1B-1E) to low-profile, delivery or compressed state (as shown in FIG. 1A) such that the implantable medical device 102 can be delivered to a target site of a patient. As such, the frame 104 can be constructed from a plastically deformable material such that when expanded by a dilatation balloon or other mechanical expansion device, the frame 104 maintains its radially expanded configuration. The frame 104 may be formed from stainless steel or other suitable metal, such as platinum iridium, cobalt chromium alloys such as MP35N, or various types of polymers or other materials known to those skilled in the art, including said materials coated with various surface deposits to improve clinical functionality. The frame 104 can be configured to be rigid such that it does not deflect or move when subjected to forces present at the target site (e.g., in-vivo forces), or such that deflection or movement is minimized when subjected to the forces.

In other embodiments, the frame 104 can be construed of superelastic shape memory materials that allow the frame 104 to self-expand. When the frame 104 is made from superelastic shape memory materials, such as Nitinol, the frame 104 can be collapsed into a very low profile delivery configuration suitable for delivery through the vasculature via the delivery system, and self-expand to a deployed configuration suitably sized to replace the target valve. The frame 104 can be a braided or woven frame, a laser-cut frame made from a metal tube, and/or other suitable stent structures. In some embodiments, the implantable medical device 102 can be maintained or retained over the inner shaft 114 by a sheath or capsule (not shown). In embodiments, a guide member or guidewire lumen (not shown) can be provided through the tip 128 and other portions of (including an entirety of) the support shaft assembly 114, and can be manipulated by the controls 124 or other controls (not shown) at the handle assembly 120 (e.g., a guide member or guidewire port). In embodiments, the sheath or capsule can be manipulated to withdraw a capsule from over the implantable medical device 102 via operation of the controls 124 or other controls (not shown) at the handle assembly 120.

In embodiments, the medical implant 106 can be a prosthetic heart valve. In this embodiment, the medical implant 106 can include two, three, or more leaflets that are arranged in a bicuspid, tricuspid, or other suitable valve configuration and attached to the frame 104 using sutures, adhesives, and/or other suitable attachment mechanisms for joining the medical implant 106 to the frame 104. The leaflets can be formed of various biocompatible, flexible, and at least substantially impermeable materials. For example, the leaflets can be made from polytetrafluoroethylene (PTFE), polyethylene terephthalate, pyrolytic carbon, biologic tissue (e.g., pericardial tissue or xenograft valve tissue such as porcine heart tissue or bovine pericardium), and/or other biocompatible materials.

As discussed above, one or more proximal alignment markers 108, one or more distal alignment markers 110, and one or more implant markers 112 can be utilized in a process to determine an axial position and/or orientation of the implantable medical device 102 as the implantable medical device 102 is being installed. FIGS. 2A-2E illustrate an example of operation of the delivery system 100 utilizing the implant markers 112 in accordance with an embodiment hereof. One skilled in the art will realize that FIGS. 2A-2E illustrate one example of the operation of the delivery system 100 and that existing components and/or operations illustrated in FIGS. 2A-2E may be removed and/or additional components may be added to the delivery system 100.

Figures 2A, 2B, 2C:
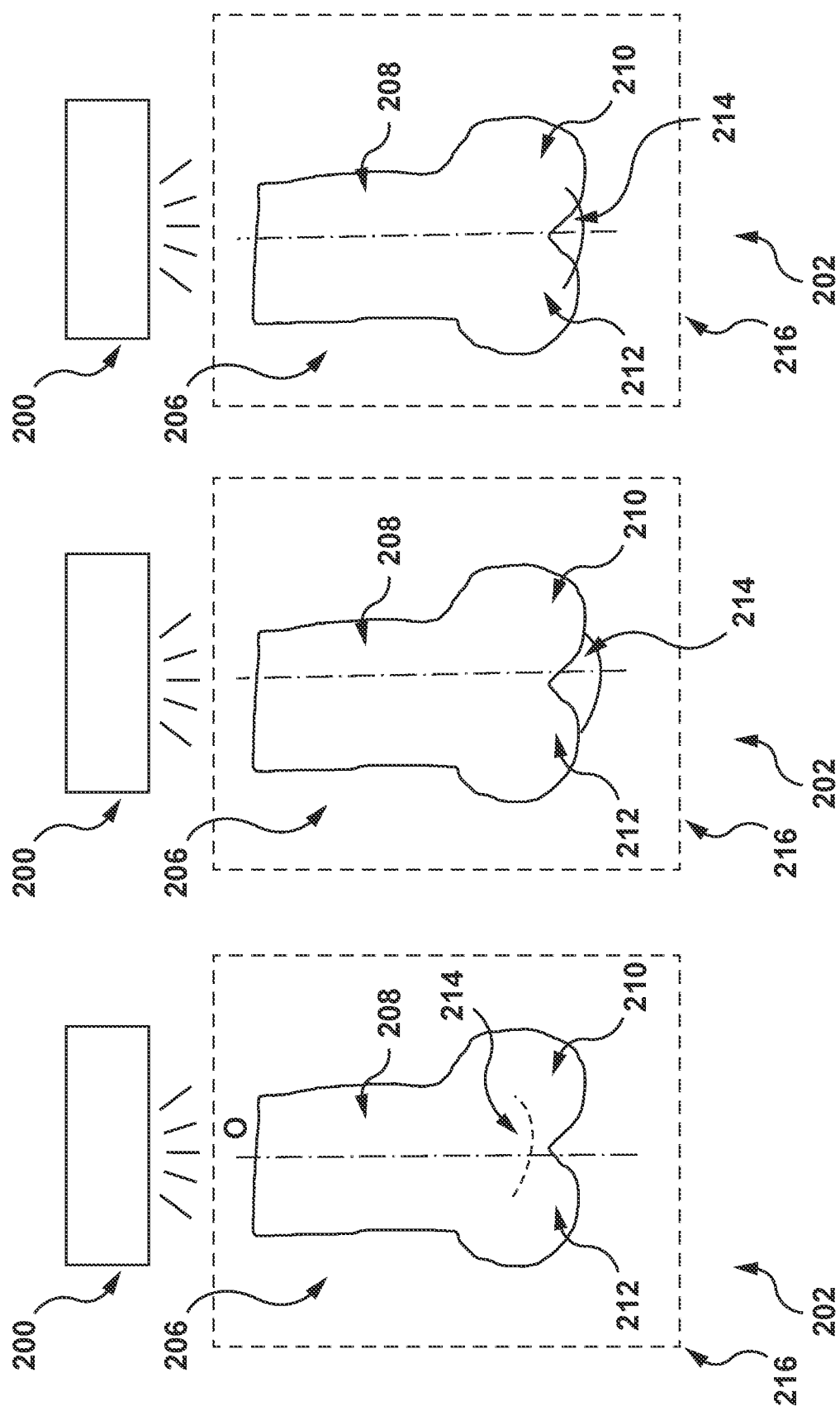
FIGS. 2A-2E depict several views an operation of the delivery system of FIGS. 1A and 1B with the implant markers in accordance with an embodiment hereof.

As illustrated in FIG. 2A, an imaging device 200 can be positioned to capture and deliver one or more images of a target site 202 of a patient. The imaging device 200 can be configured to illuminate the target site 202 with electromagnetic radiation and/or detect electromagnetic radiation emitted and/or reflected from structure and objects at the target site 202. For example, the imaging device 200 can be configured to utilize imaging techniques such as fluoroscopy, computed tomography (CT), magnetic resonance (MRI), etc.

Prior to delivering the implantable medical device 102 using the delivery system 100, the imaging device 200 can be aligned with native anatomy 206 of the target site 202. For example, as illustrated, the target site 202 can include a valve annulus 208 of a native heart valve including heart valve cusps 210, 212, and 214. In embodiments, implant markers 112 are configured to assist in the orientation (e.g., tilt, rotation, axial alignment, etc.) of the implantable medical device 102 when delivered to the native anatomy 206, e.g., the valve annulus 208. The imaging device 200, producing images, is aligned with the native anatomy 206, e.g., the valve annulus 208, such that an aligned image plane 216 of the imaging device 200 is positioned to be parallel to a desired orientation axis, O, e.g., the desired orientation axis, O, lies in the aligned image plane 216.

As illustrated in FIGS. 2A-2C, the aligned image plane 216 of the imaging device 200 is positioned relative to the desired orientation axis, O, by aligning the native anatomy 206, e.g., cusps 210, 212, and 214, viewable in the images produced by the imaging device 200. As illustrated in FIG. 2A, when directed at the target site 202, the images produced by the imaging device 200 may only show cusps 210 and 212 indicating the desired orientation axis, O, does not lie in the aligned image plane 216. Or, as illustrated in FIG. 2B, the images produced by the imaging device 200 may show a larger portion of cusp 214 relative to portions of the cusps 210 and 212 indicating the desired orientation axis, O, does not lie in the aligned image plane 216.

To align the image plane 216, the imaging device can be repositioned relative to the target site 202 until the native anatomy 206, e.g., cusps 210, 212, and 214 is correctly visible in the images produced by the imaging device 200. For example, as illustrated in FIG. 2C, the imaging device 200 may be repositioned until equal amounts of the cusps 210, 212, and 214 are visible indicating the desired orientation axis, O, lies in the aligned image plane 216.

Once the imaging device is positioned to produce the aligned image plane 216, the implant markers 112 can be utilized to position the implantable medical device at the correct orientation (e.g., tilt, rotation, radial position, etc.) For example, as illustrated in FIG. 2D, the implantable medical device 102 may be delivered and installed in a valve annulus 206 of a heart valve. In order to function properly, the implantable medical device 102 needs to be aligned relative to the valve annulus 206 so that the implantable medical device 102 engages with the valve annulus 206 when radially expanded.

In embodiments, the one or more of the implant markers 112 can be positioned on the implantable medical device 102, for example, on the proximal end 116 of the frame 104. In embodiments, the implant markers 112 can be utilized to position and align (e.g., tilt, rotate, radial position, etc.) the implantable medical device 102 to ensure proper installation. As illustrated in FIG. 2D, the one or more implant markers 112 can be used to determine an orientation of the central axis, A, relative to a desired orientation axis within native anatomy, e.g., the valve annulus 208. For example, the orientation can include a tilt of the implantable medical device 102, e.g., an angle of the central axis, A, in the x-direction, y-direction, and/or z-direction relative to the valve annulus 208. Likewise, the orientation can include a rotation of the implantable medical device 102, e.g., rotational position of various components of the implantable medical device 102 about the central axis, A, relative to the valve annulus 208. As the implantable medical device is moved and positioned in the native anatomy, e.g., the valve annulus 208, the operator of the delivery system 100 can observe the images produced by the imaging device 200 and determine the correct orientation based on the position, visual shape, relative position, etc. of the implant markers 112, as shown in FIGS. 3A-3G, 4A-4G, 5A-5B, and 6A-6B.

Figure 2E:
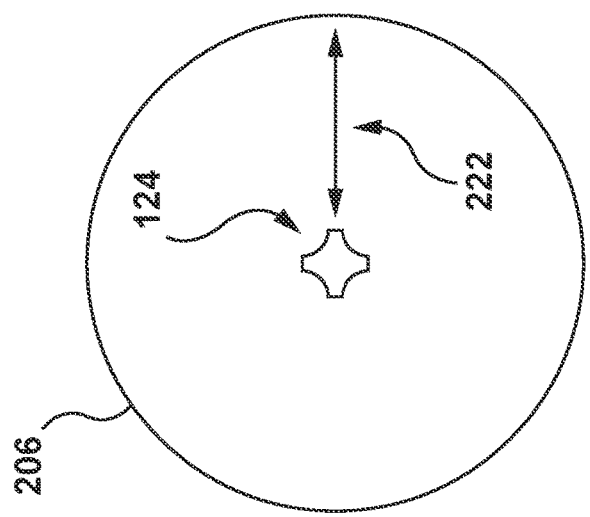
Figure 2D:
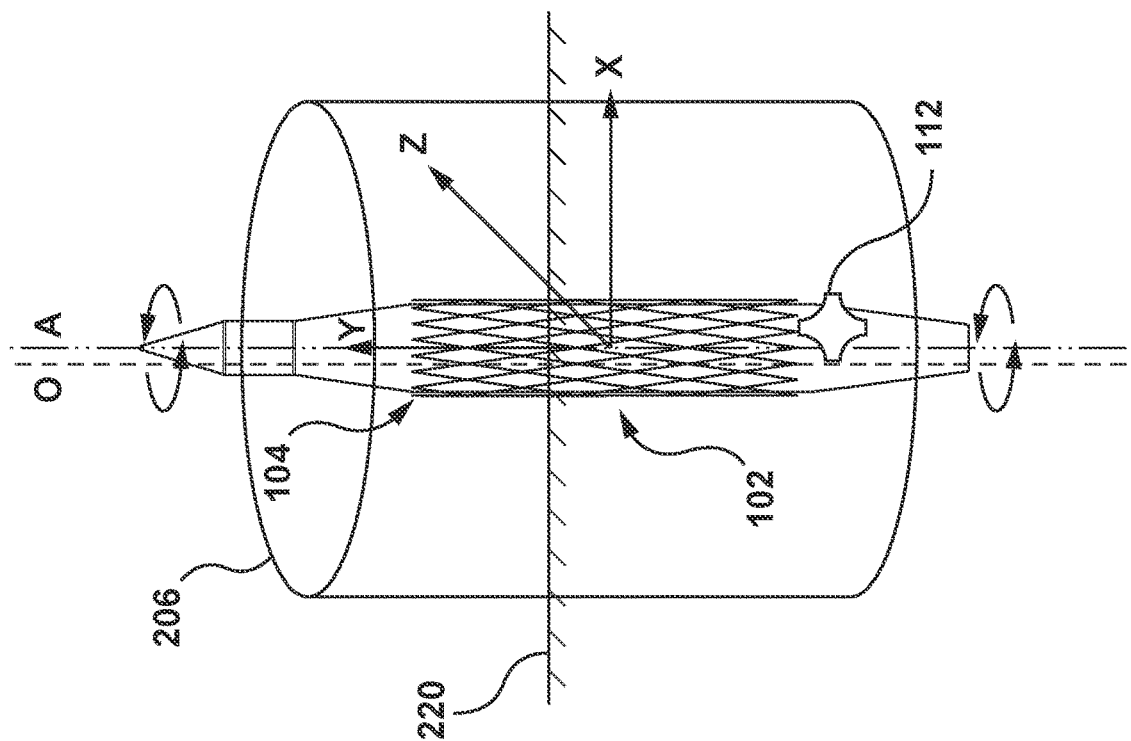

Likewise, as illustrated in FIG. 2E, when view from the annular plane 220, the implant marker 112 can be utilized to align the radial position 222 of the medical implant device 102 within the annual of the native anatomy, e.g., the annulus 208. That is, the implant marker 112 can be viewed relative to the wall of the annulus 206 in order to locate the implantable medical device 102 at the proper radial position 222 from the wall of the annulus 208.

FIGS. 3A-3G illustrate an example of an arrangement 300 of the implant markers 112 in accordance with an embodiment hereof. One skilled in the art will realize that FIGS. 3A-3G illustrate one example of an arrangement of implant markers 112 and that existing components illustrated in FIGS. 3A-3G may be removed and/or additional components may be added to the arrangement 300 of implant markers 112.

Figure 3A:
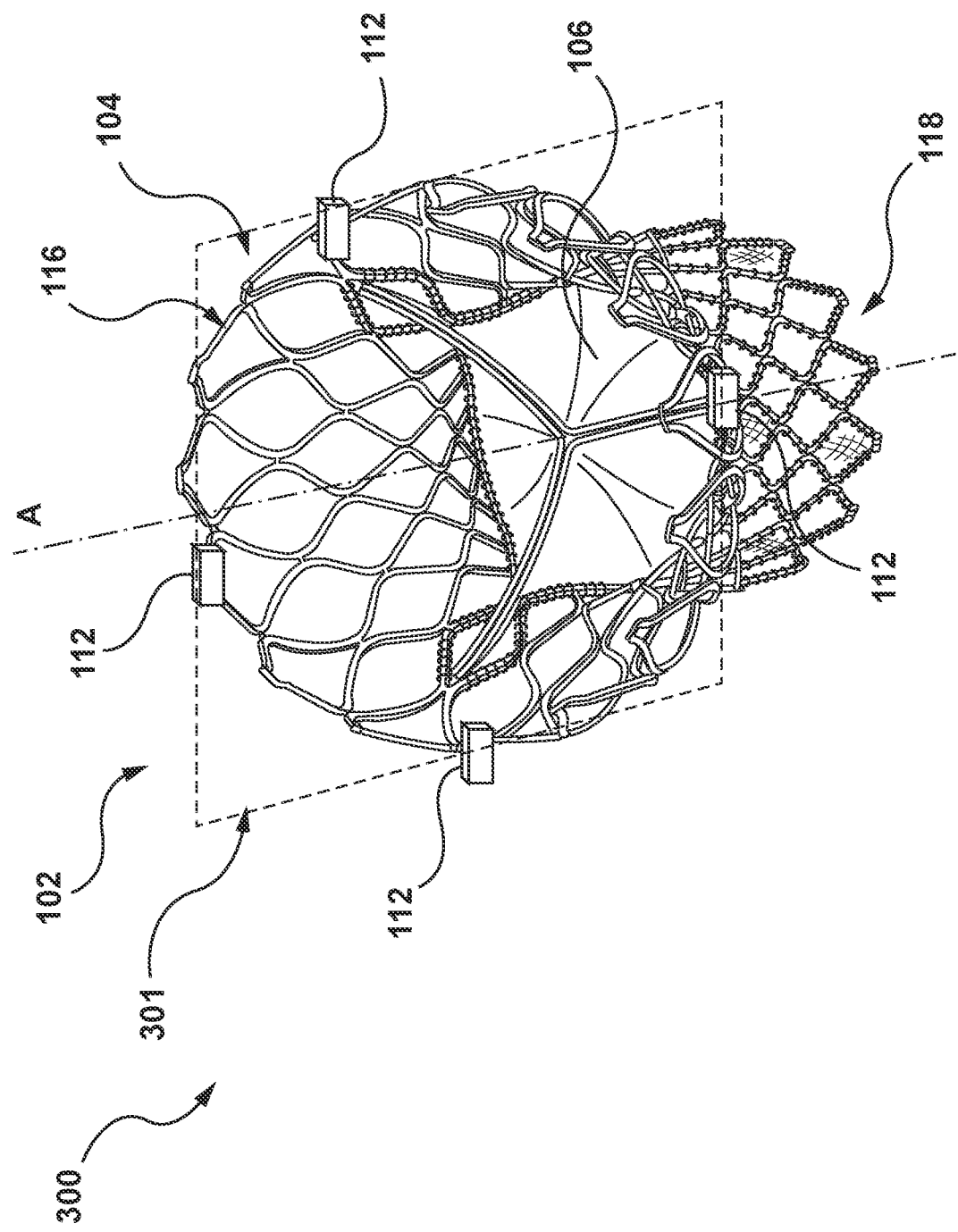
FIGS. 3A-3G depict several views of an arrangement of implant markers of the delivery system of FIGS. 1A and 1B in accordance with an embodiment hereof.

As illustrated in FIG. 3A, the implantable medical device 102 can include four (4) implant markers 112 attached to the frame 104. The implant markers 112 are positioned on the frame 104 in a marker plane 301 that is approximately perpendicular to the central axis, A. As illustrated, the implant markers 112 can be attached to the proximal end 116 of the frame 104. While FIG. 3A illustrates the implant markers 112 are positioned at the proximal end 116, in other embodiments, the implant markers 112 can be positioned, in the implant plane 301, in the axial direction along the central axis, A, of the frame 104 at any location, for example, at the distal end 118.

In an embodiment, the implant markers 112 can be formed in the shape of a bar. In other embodiments, the implant markers 112 can be formed in any shape and size to accommodate the installation of the implantable medical device 102. For example, one or more of the implant markers 112 can be pins, dots, cubes, crosses, and combinations thereof. Additionally, while FIG. 3A illustrates 4 implant markers 112, one skilled in the art will realize that the implantable medical device 102 can include additional or fewer implant markers 112.

Figure 3C:
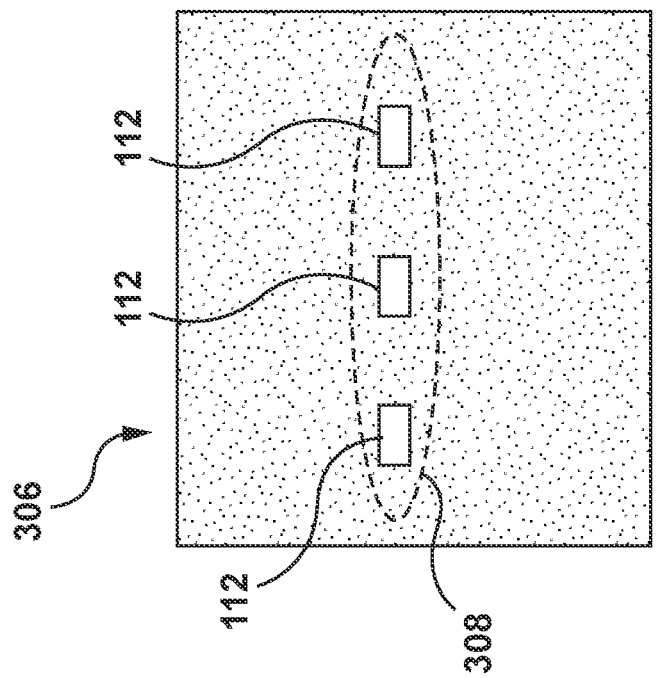
Figure 3B:
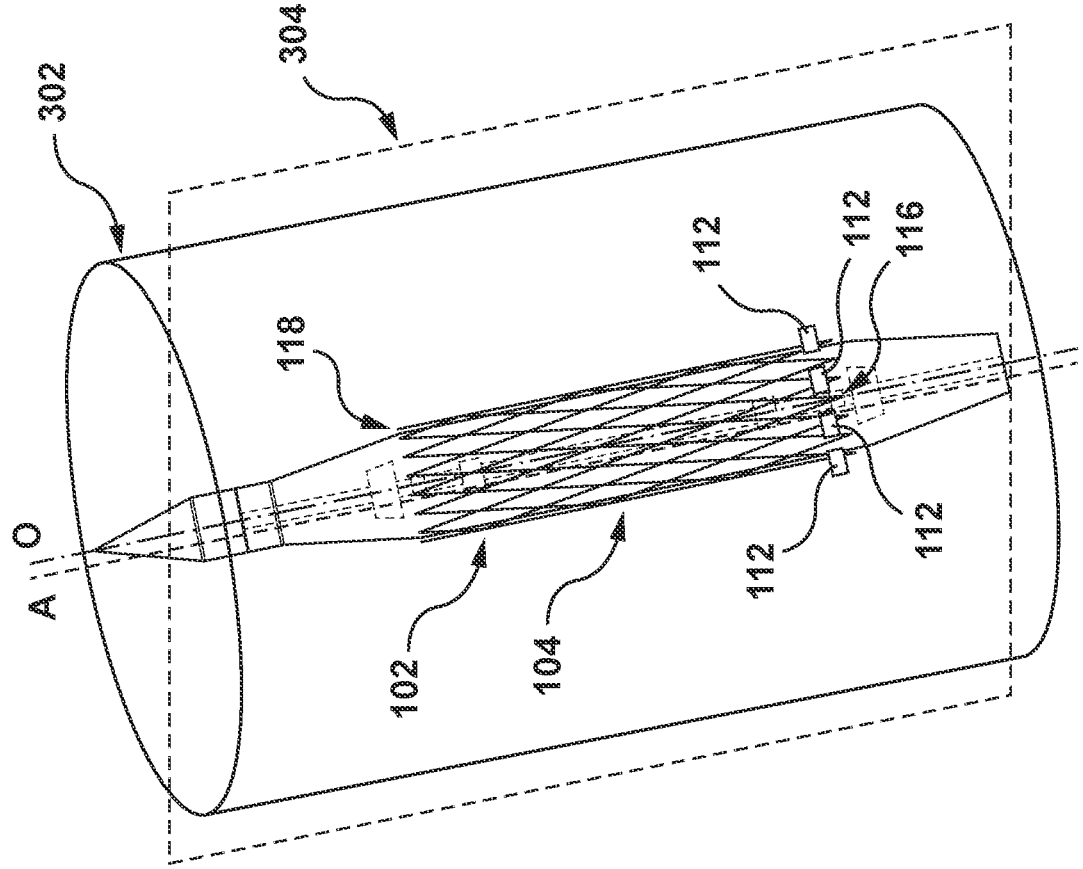

The implant markers 112 are configured to assist in the orientation (e.g., tilt, rotations, axial alignment, etc.) of the implantable medical device 102. As discussed above with reference to FIGS. 2A-2E, the imaging device 200, producing images 306, is aligned with the anatomy of the patient (e.g., an annulus 302) such that an aligned image plane 304 of the imaging device 200 is positioned to be parallel to a desired orientation axis, O, as further illustrated in FIG. 3B. To align the implantable medical device 102, the delivery system 100 can be manipulated (e.g., rotated, tilted, etc.) until all 4 of the implant markers 112 form a predetermined pattern 308 that is visible in the image 306 captured in the image plane 304, as illustrated in FIGS. 3B and 3C. For example, as illustrated in FIG. 3C, the predetermined pattern 308 for the 4 implant markers 112 can include the 4 implant markers 112 forming a line (e.g., indicating proper tilt), and/or 1 of the 4 implant markers 112 obscuring another of the implant markers 112 (e.g., indicating proper rotation).

Figure 3E:
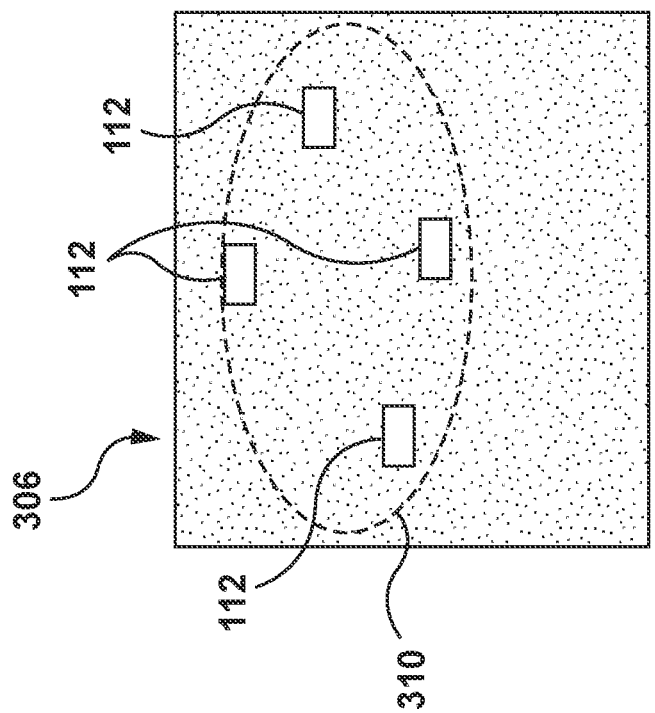
Figure 3D:
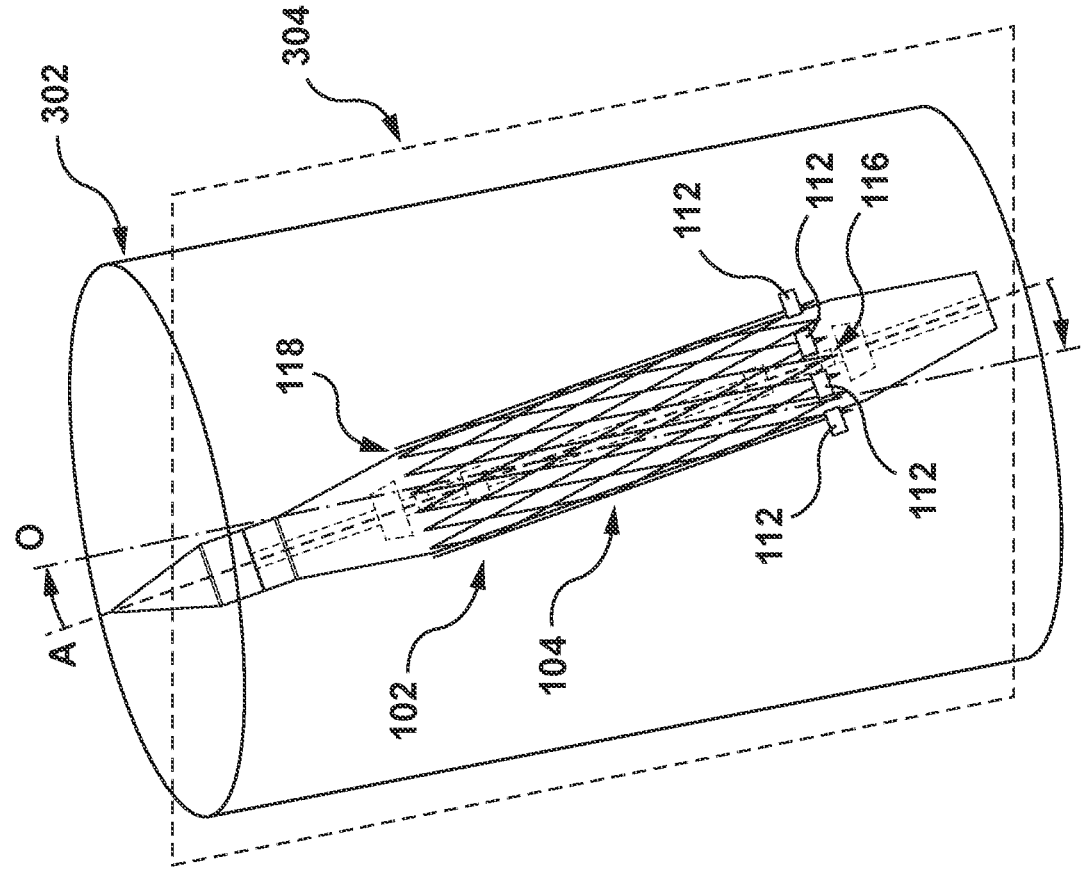

In embodiments, if the image plane 304 is aligned with the native anatomy as desired, the appearance of the pattern 308 indicates the implant plane 301 is approximately perpendicular to image plane 304 indicating proper orientation (e.g., indicating proper tilt) of the implantable medical device 102, as illustrated in FIG. 3C. As such, the central axis, A, of the implantable medical device 102 is aligned with the desired orientation axis, O. If the central axis, A, is not aligned with the desired orientation axis, O, other patterns, not the predetermined pattern 308 of the 4 implant markers 112, will be visible in the image 306 captured in the image plane 304. For example, as illustrated in FIG. 3D, the implantable medical device 102 may be tilted, e.g., the central axis, A, is tilted at an angle relative to the desired orientation axis, O. As illustrated in FIG. 3E, a pattern 310, e.g., the 4 implant markers 112 scattered and not in a line, may appear in the image 306, which indicates the tilt. To correct the orientation, the operator of the delivery system 100 can move the implantable medical device 102 (e.g., tilt) until the predetermined pattern 308 appears.

Figure 3G:
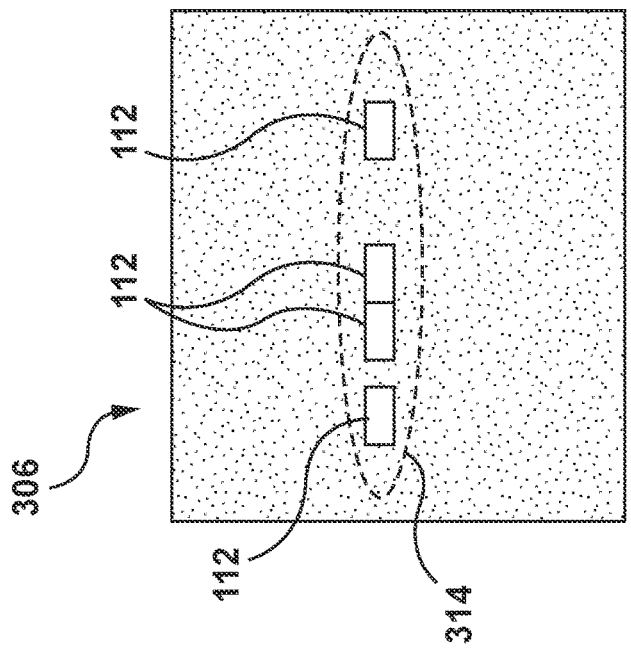
Figure 3F:
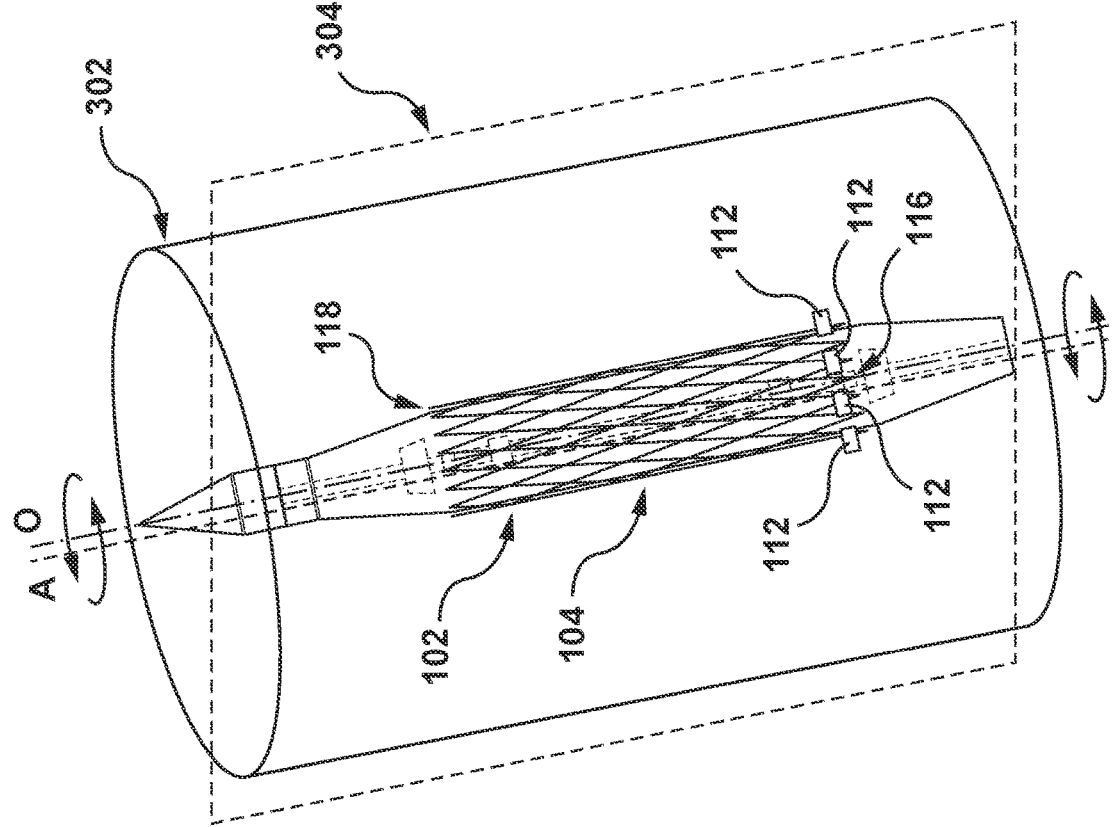

In embodiments, the 4 implant markers 112 can be utilized to align the rotational orientation (e.g., the rotation about the central axis, A) of the implantable medical device 102. For example, if the 4 implant markers 112 are placed on the frame 104 at positions that reference proper rotational orientation and 1 of the 4 implant markers 112 obscures another of the implant markers 112, the predetermined pattern indicates proper rotational orientation of the implantable medical device 102, as illustrated in FIG. 3C. Likewise, for example, as illustrated in FIG. 3F, the implantable medical device 102 may be rotated about the central axis A. As such, as illustrated in FIG. 3G, a pattern 314 may appear in the image 306, e.g., the 4 implant markers 112 aligned in a line, but all or a portion of all the 4 implant markers 112 are visible, indicating the rotation. To correct the orientation, the operator of the delivery system 100 can move the implantable medical device 102 (e.g., rotate) until the predetermined pattern 308 appears.

FIGS. 4A-4G illustrate an example of an arrangement 400 of the implant markers 112 in accordance with an embodiment hereof. One skilled in the art will realize that FIGS. 4A-4G illustrate one example of an arrangement of implant markers and that existing components illustrated in FIGS. 4A-4G may be removed and/or additional components may be added to the arrangement 400 of implant markers 112.

Figure 4A:
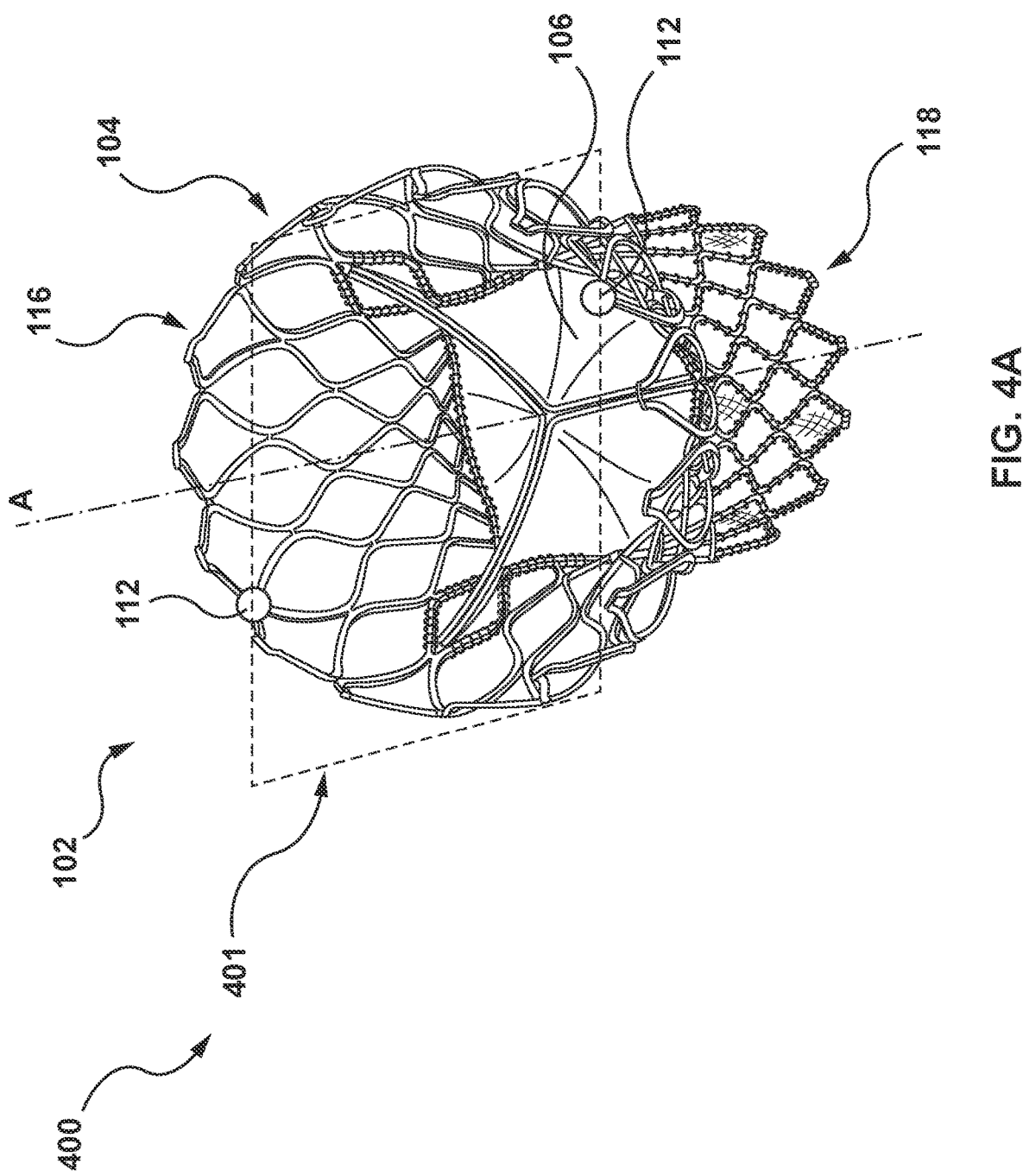

As illustrated in FIG. 4A, the implantable medical device 102 can include two (2) implant markers 112 attached to the frame 104. The implant markers 112 are positioned on the frame 104 in a marker plane 401 that is approximately perpendicular to the central axis, A. As illustrated, the implant markers 112 can be attached to the proximal end 116 of the frame 104. While FIG. 4A illustrates the implant markers 112 are positioned at the proximal end 116, in other embodiments, the implant markers 112 can be positioned, in the implant plane 401, in the axial direction along the central axis, A, of the frame 104 at any location, for example, at the distal end 118.

In an embodiment, the implant markers 112 can be formed in the shape of a circle. Each of the 2 implant markers 112 is formed having approximately the same diameter. In other embodiments, the implant markers 112 can be formed in any shape and relative size, with the 2 implant markers being approximately equal size or one of the two being larger, to accommodate the installation of the implantable medical device 102. For example, one or more of the 2 implant markers 112 can be pins, dots, cubes, crosses, and combinations thereof. Additionally, while FIG. 4A illustrates 2 implant markers 112, one skilled in the art will realize that the implantable medical device 102 can include additional or fewer implant markers 112.

Figure 4C:
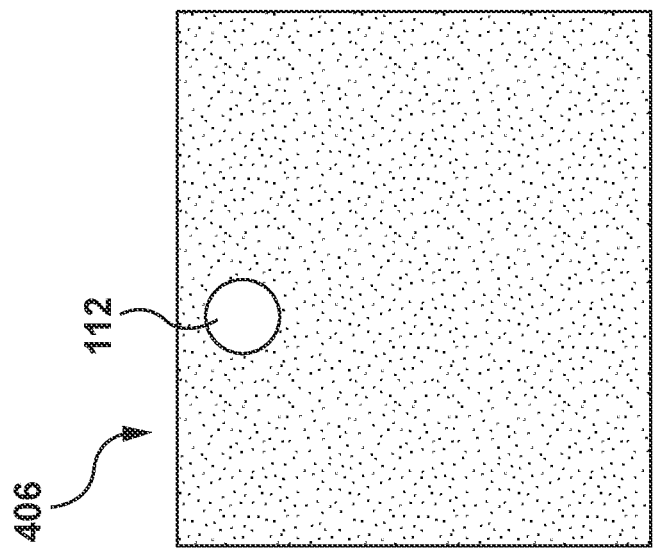
Figure 4B:
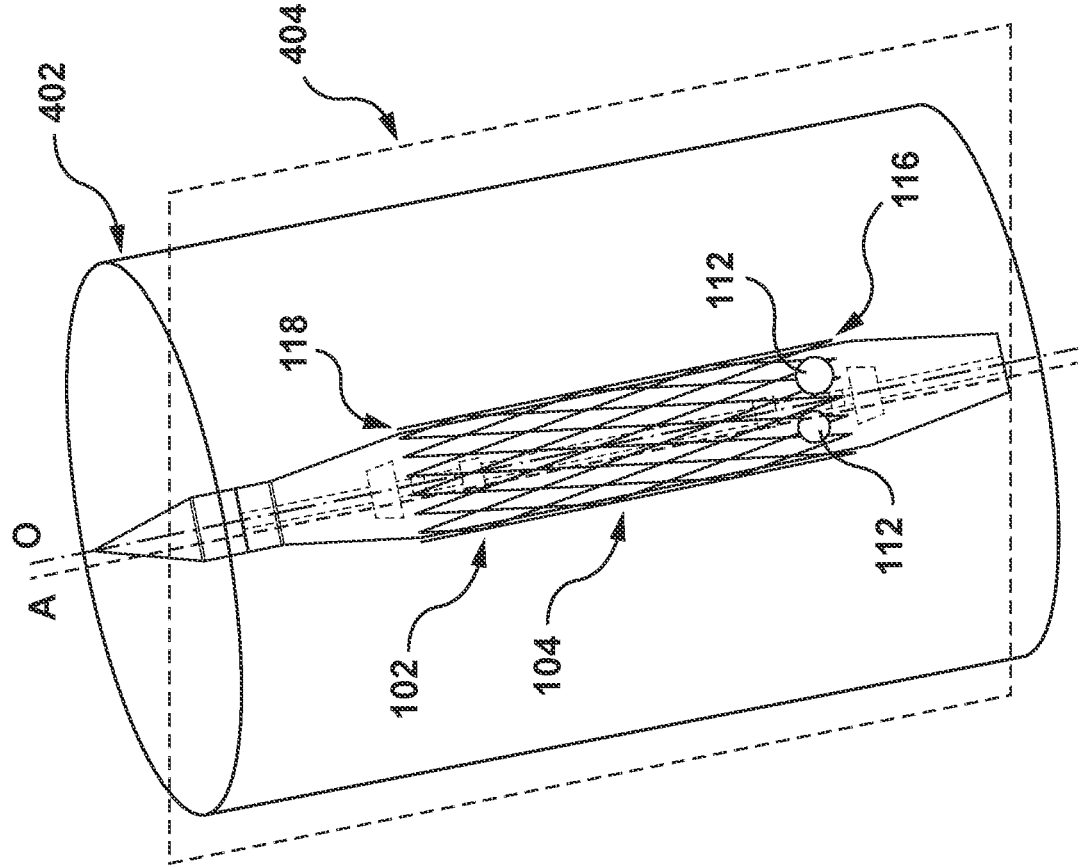

The 2 implant markers 112 are configured to assist in the orientation (e.g., tilt, rotation, etc.) of the implantable medical device 102. As discussed above with reference to FIGS. 2A-2E, the imaging device 200, producing images 406, is aligned with the anatomy of the patient (e.g., an annulus 402) such that an aligned image plane 304 of the imaging device 200 is positioned to be parallel to a desired orientation axis, O, as further illustrated in FIG. 4B. To align the implantable medical device 102, the delivery system 100 can be manipulated (e.g., rotated, tilted, etc.) until one of the 2 implant markers 112, which is visible in the image 406 captured in the image plane 404, completely obscures the other of the 2 implant markers 112, as illustrated in FIG. 4C. As illustrated in FIG. 4C, the appearance of only one of the 2 implant markers 112 can indicate proper tilt and/or proper rotation. If the image plane 404 is aligned with the native anatomy as desired, one of the 2 implant markers 112 completely obscuring the other indicates the implant plane 401 is approximately perpendicular to image plane 304 indicating proper orientation of the implantable medical device 102. As such, the central axis, A, of the implantable medical device 102 is aligned with the desired orientation axis, O.

In embodiments, if the central axis, A, is not aligned with the desired orientation axis, O, all or part of the 2 implant markers 112 are visible in the image 406 captured in the image plane 404, as illustrated in FIGS. 4D-4G. When visible, the location of the 2 implant markers 112 can indicate to the operator of the delivery system 100 type and a direction to correct orientation, e.g., tilt the implantable medical device 112, rotate the implantable medical 112, or combination of both. For example, as illustrated in FIG. 4D, the implantable medical device 102 may be tilted, e.g., the central axis, A, is tilted at an angle relative to the desired orientation axis, O). As illustrated in FIG. 4E, one of the 2 implant markers 112 may appear above the other in the image 406, which indicates the tilt. To correct the orientation, the operator of the delivery system 100 can move the implantable medical device 102 (e.g., tilt) until one of the 2 implant markers 112 obscures the other implant marker 112.

Figure 4G:
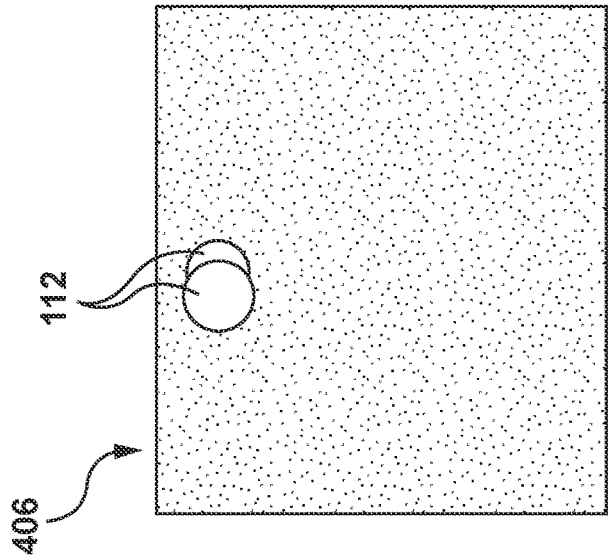
Figure 4F:
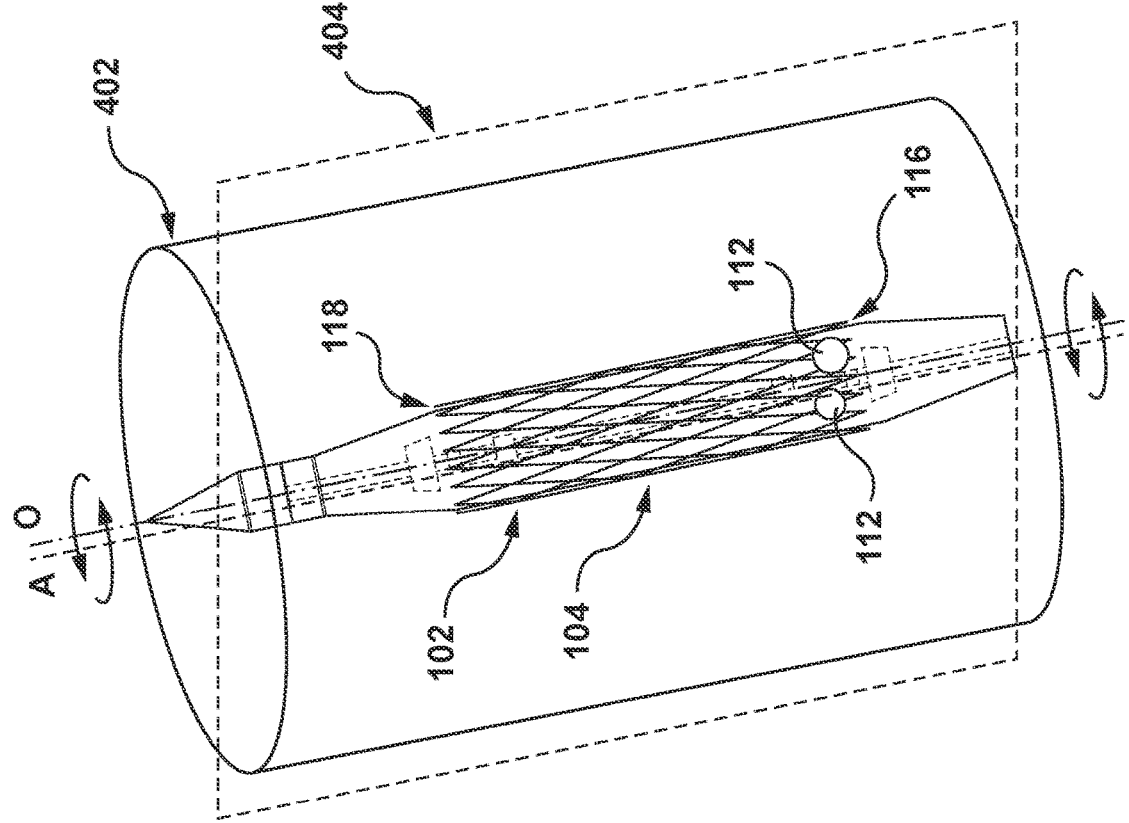

In embodiments, the 2 implant markers 112 can be utilized to align the rotational orientation (e.g., the rotation about the central axis, A) of the implantable medical device 102. For example, if the 2 implant markers 112 are placed on the frame 104 at positions that reference proper rotational orientation and one of the 2 implant markers 112 obscures the other implant marker 112, this indicates proper rotational orientation of the implantable medical device 102, as illustrated in FIG. 4C. Likewise, for example, as illustrated in FIG. 4F, the implantable medical device 102 may be rotated about the central axis, A. As such, as illustrated in FIG. 4G, all or part of one of the 2 implant markers 112 may appear beside the other implant marker 112, indicating the rotation. To correct the orientation, the operator of the delivery system 100 can move the implantable medical device 102 (e.g., rotate) until one of the 2 implant markers 112 obscures the other implant marker 112.

While FIGS. 4D-4G illustrate separate orientation of tilt and rotation, one skilled in the art will realize that the tilt and rotation may be aligned simultaneously. For example, one of the two implant markers 112 may appear diagonally from the other implant marker 112 in the image 406, indicating tilt and rotation correction is required.

Figure 5A:
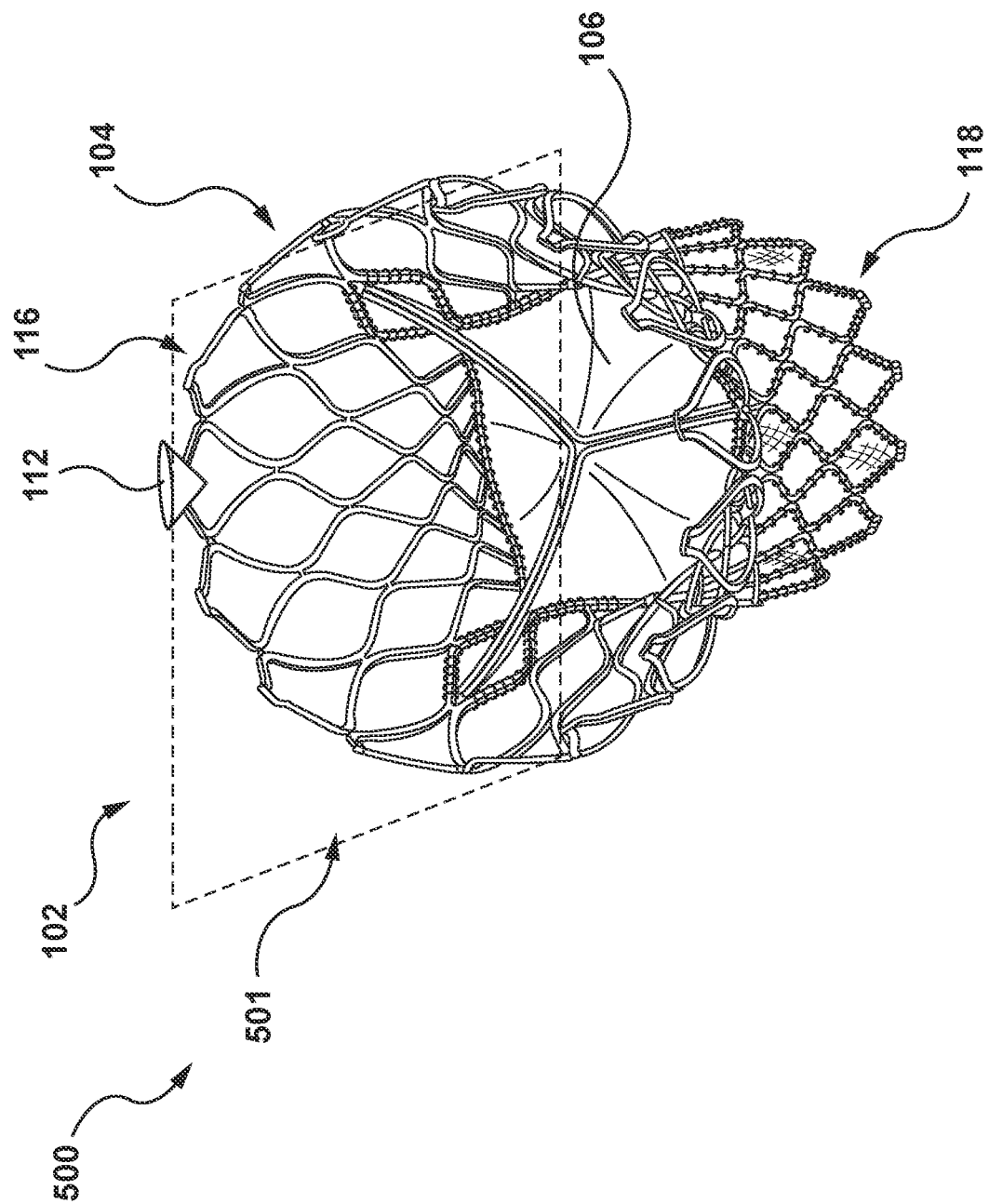
FIGS. 5A-5E depict several views of another arrangement of implant markers of the delivery system of FIGS. 1A and 1B in accordance with an embodiment hereof.
Figure 5C:
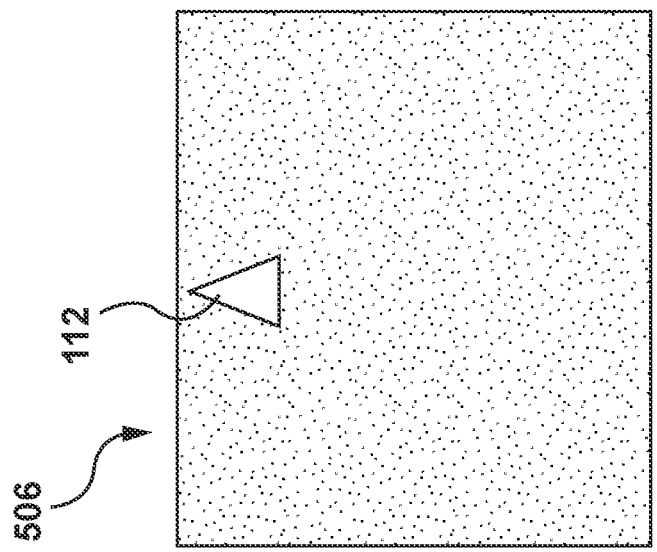
Figure 5B:
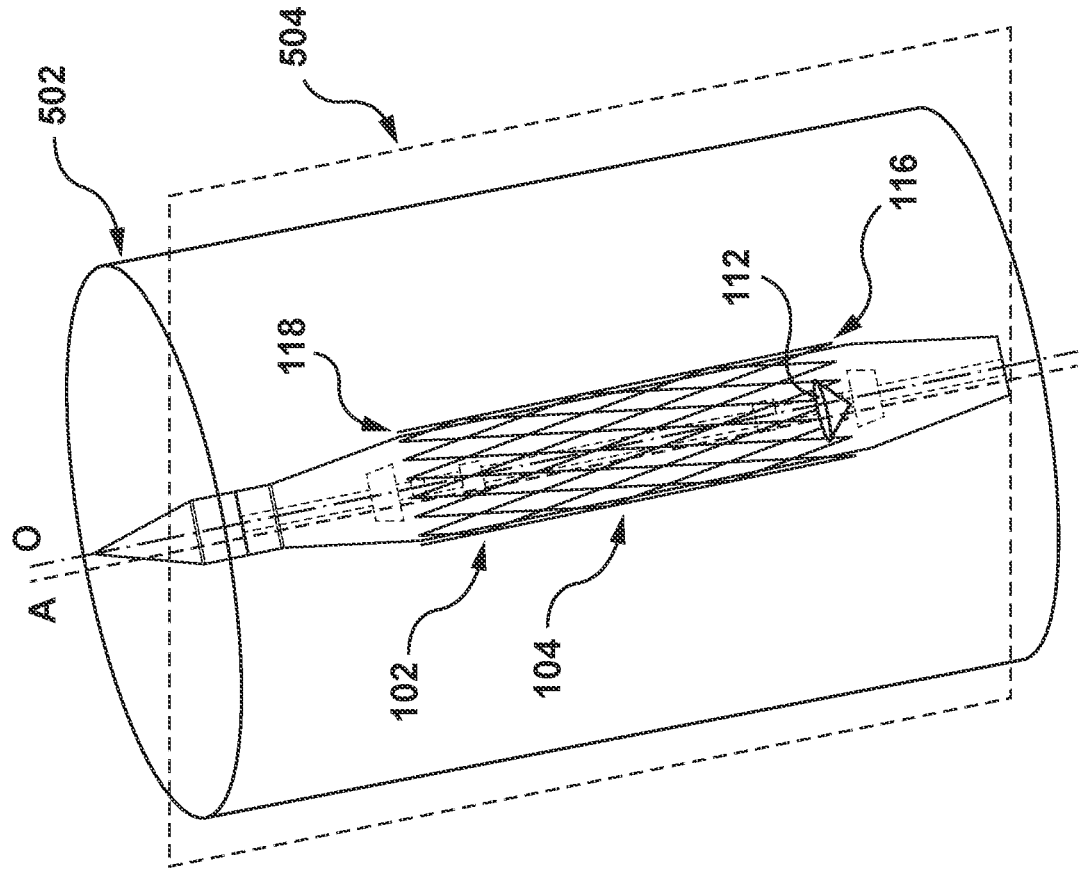
Figure 5E:
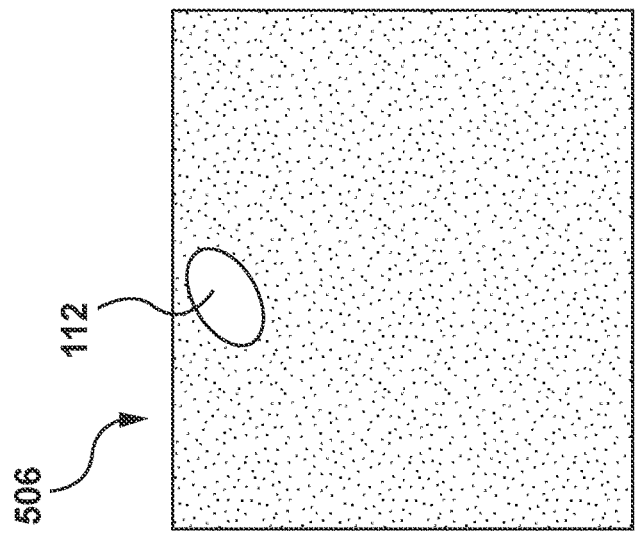

FIGS. 5A and 5B illustrate an example of an arrangement 500 of the implant markers 112 in accordance with an embodiment hereof. One skilled in the art will realize that FIGS. 5A and 5B illustrate one example of an arrangement of implant markers 112 and that existing components illustrated in FIGS. 5A and 5B may be removed and/or additional components may be added to the arrangement 500 of implant markers 112.

As illustrated in FIG. 5A, the implantable medical device 102 can include a single implant marker 112 attached to the frame 104. The implant marker 112 is positioned on the frame 104 in a marker plane 501 that is approximately perpendicular to the central axis, A. As illustrated, the implant marker 112 can be attached to the proximal end 116 of the frame 104. While FIG. 5A illustrates the implant marker 112 is positioned at the proximal end 116, in other embodiments, the implant marker 112 can be positioned, in the implant plane 501, in the axial direction along the central axis, A, of the frame 104 at any location, for example, at the distal end 118.

In an embodiment, the implant marker 112 can be formed in the shape of a three dimensional (3D) cone. As discussed above with reference to FIGS. 2A-2E, the imaging device 200, producing images 506, is aligned with the anatomy of the patient (e.g., an annulus 502) such that an aligned image plane 504 of the imaging device 200 is positioned to be parallel to a desired orientation axis, O), as further illustrated in FIG. 5B. The 3D cone shape has a property of appearing as different shapes in a two dimensional (2D) image depending on the orientation of the marker plane 501 relative to the aligned image plane 504. For example, if the aligned image plane 504 is perpendicular to the base of the 3D cone, the image of the 3D cone will appear as a triangle. Likewise, if the aligned image plane 504 is not perpendicular to the base of the 3D cone, the image of the 3D cone will appear as a different shape. As such, the implant marker 112 is configured to assist in the orientation (e.g., tilt, rotations, axial alignment, etc.) of the implantable medical device 102.

To align the implantable medical device 102, the delivery system 100 can be manipulated (e.g., rotated, tilted, etc.) until the predetermined 2D shape (e.g., triangle) is visible in the image 506 captured in the image plane 504, as illustrated in FIG. 5C. As illustrated in FIG. 5C, ff the image plane 504 is aligned with the native anatomy as desired, the appearance of the predetermined 2D shape (e.g., triangle) indicates the implant plane 501 is approximately perpendicular to image plane 504 indicating proper orientation of the implantable medical device 102. As such, the central axis, A, of the implantable medical device 102 is aligned with the desired orientation axis, O.

Figure 5D:
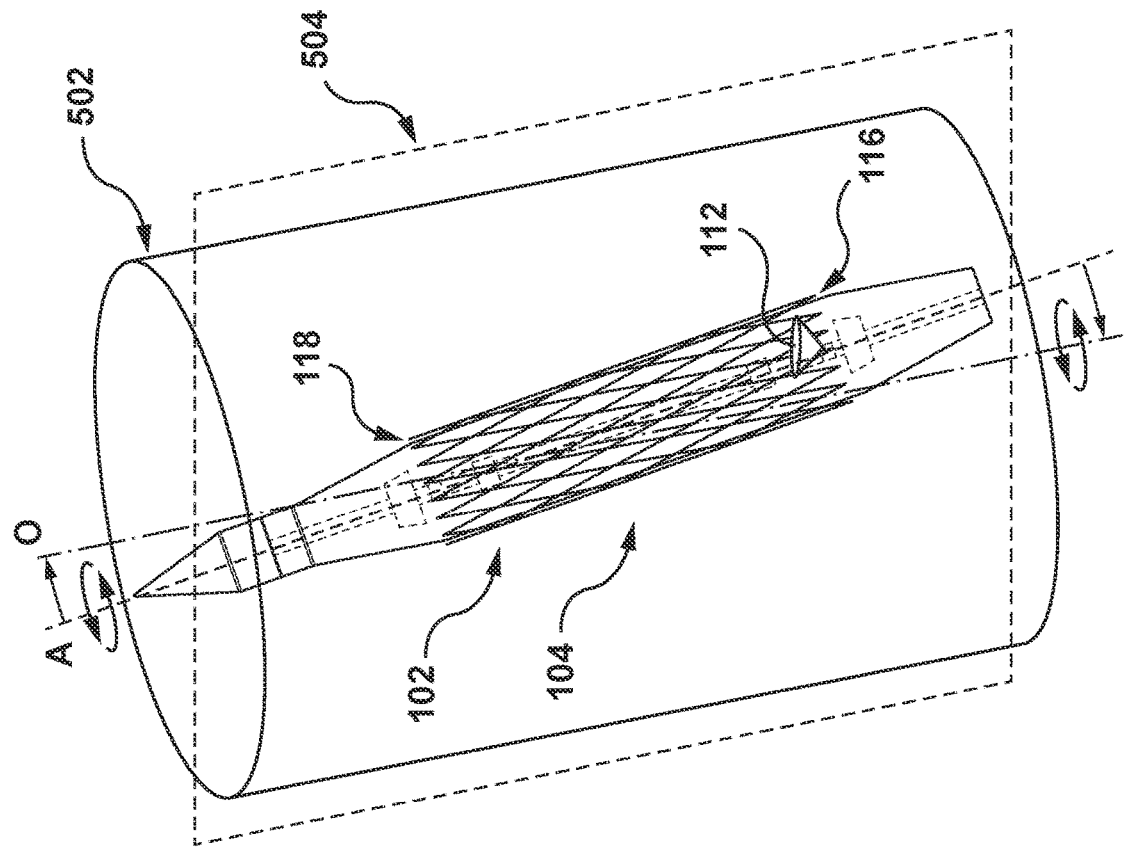

If the central axis, A, is not aligned with the desired orientation axis, O, other 2D shapes (e.g., oval or other shape), not the predetermined 2D shape (e.g., triangle) of the implant marker 112, will be visible in the image 506 captured in the image plane 504. For example, as illustrated in FIG. 5D, the implantable medical device 102 may be tilted, e.g., the central axis, A, is tilted at an angle relative to the desired orientation axis, O, and/or rotated about the central axis, A. As illustrated in FIG. 5F, other 2D shapes (e.g., oval or other shape) may appear above the other in the image 506, which indicates the tilt and/or rotated. To correct the orientation, the operator of the delivery system 100 can move the implantable medical device 102 (e.g., tilt and/or rotate the implantable medical device) until the predetermined 2D shape (e.g., triangle) appears.

While FIG. 5A illustrates only a single implant marker 112, one skilled in the art will realize that additional implant markers 112 can be positioned on the implantable medical device 102. Likewise, while the implant marker 112 is formed in the shape of a 3D cone, one skilled in the art will realize that the implant marker 112 can be formed in any shape that produces distinct 2D images depending on the angle of the image plane.

Figure 6A:
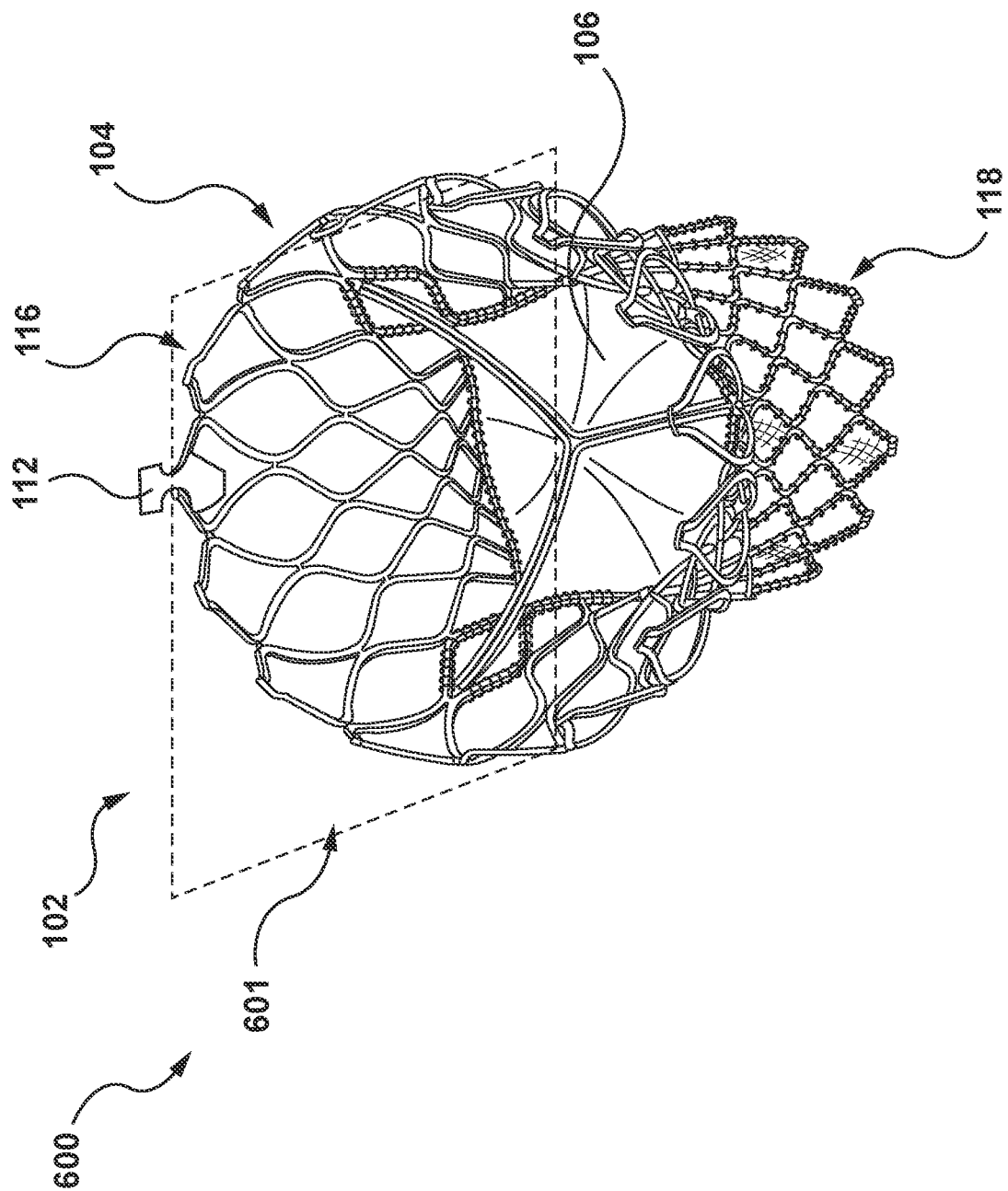
FIGS. 6A-6E depict several views of another arrangement of implant markers of the delivery system of FIGS. 1A and 1B in accordance with an embodiment hereof.
Figure 6C:
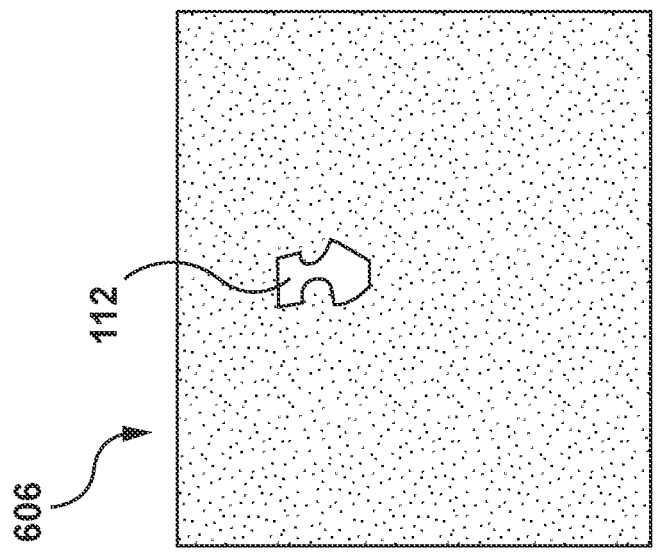
Figure 6B:
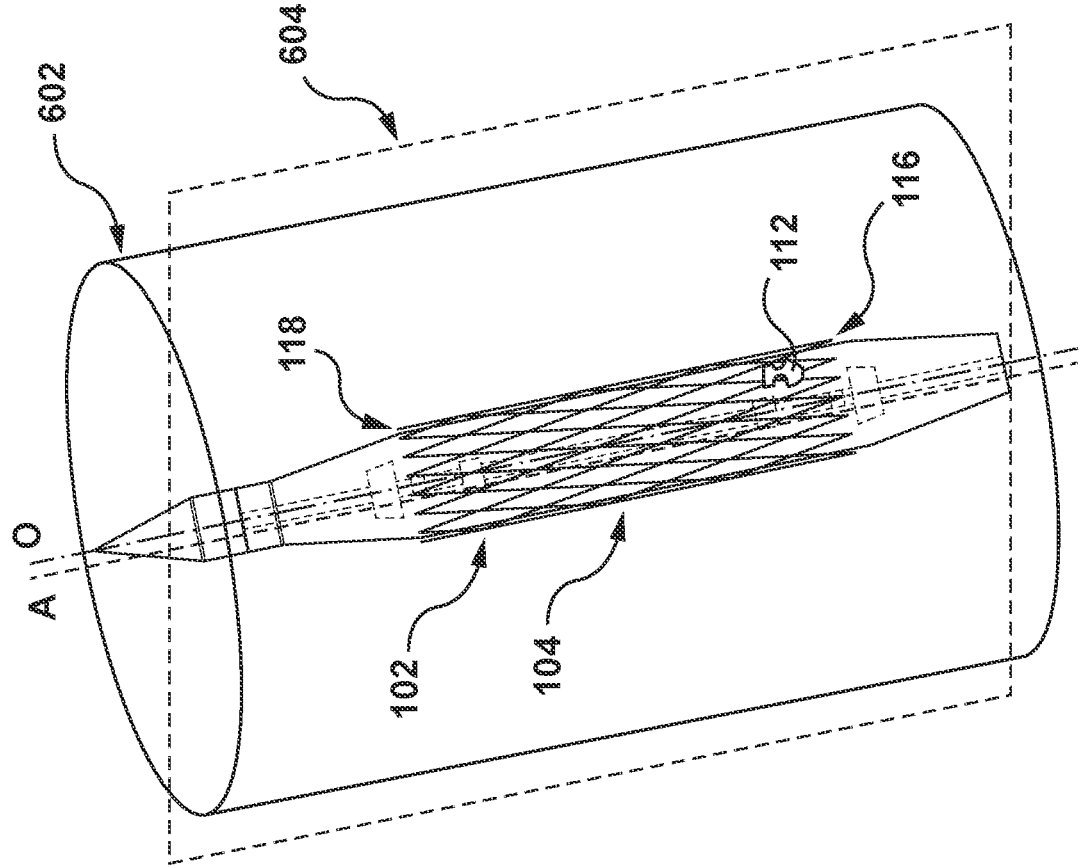
Figure 6E:
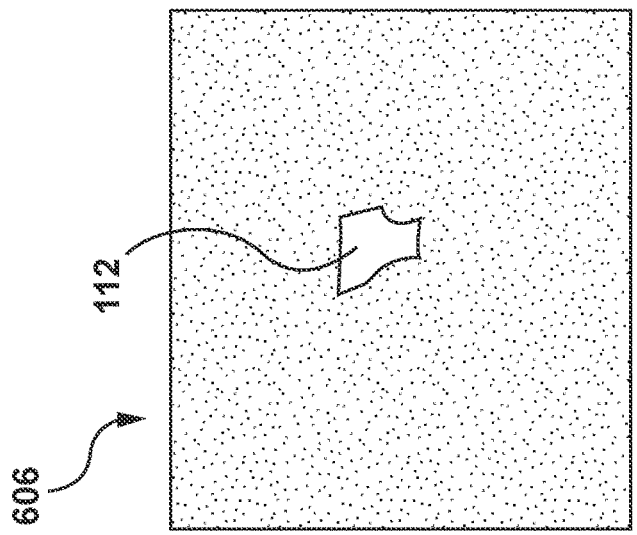

FIGS. 6A and 6B illustrate an example of an arrangement 600 of the implant markers 112 in accordance with an embodiment hereof. One skilled in the art will realize that FIGS. 6A and 6B illustrate one example of an arrangement of implant markers 112 and that existing components illustrated in FIGS. 6A and 6B may be removed and/or additional components may be added to the arrangement 600 of implant markers 112.

As illustrated in FIG. 6A, the implantable medical device 102 can include a single implant marker 112 attached to the frame 104. The implant marker 124 is positioned on the frame 104 in a marker plane 601 that is approximately perpendicular to the central axis, A. As illustrated, the implant marker 112 can be attached to the proximal end 116 of the frame 104. While FIG. 6A illustrates the implant marker 112 is positioned at the proximal end 116, in other embodiments, the implant marker 112 can be positioned, in the implant plane 601, in the axial direction along the central axis, A, of the frame 104 at any location, for example, at the distal end 118.

In an embodiment, the implant marker 112 can be formed in the shape of a defined 2D cross-sectional shape. As discussed above with reference to FIGS. 2A-2E, the imaging device 200, producing images 606, is aligned with the anatomy of the patient (e.g., an annulus 602) such that an aligned image plane 604 of the imaging device 200 is positioned to be parallel to a desired orientation axis, O, as further illustrated in FIG. 6B. The defined 2D cross-sectional shape has a property of appearing as different shapes in a 2D image depending on the orientation of the marker plane 601 relative to the aligned image plane 604. For example, if the aligned image plane 604 is parallel to cross-sectional area of the defined 2D cross-sectional shape, the image of the defined 2D cross-sectional shape will appear. Likewise, if the aligned image plane 604 is not parallel to the cross-sectional area of defined 2D cross-sectional shape, the image of the different 2D shape will appear. As such, the implant marker 112 is configured to assist in the orientation (e.g., tilt, rotations, axial alignment, etc.) of the implantable medical device 102.

To align the implantable medical device 102, the delivery system 100 can be manipulated (e.g., rotated, tilted, etc.) until the defined 2D cross-sectional shape is visible in the image 606 captured in the image plane 604, as illustrated in FIG. 6C. As illustrated in FIG. 6C, if the image plane 604 is aligned with the native anatomy as desired, the appearance of the defined 2D cross-sectional shape indicates the implant plane 601 is approximately perpendicular to image plane 604 indicating proper orientation of the implantable medical device 102. As such, the central axis, A, of the implantable medical device 102 is aligned with the desired orientation axis, O.

Figure 6D:
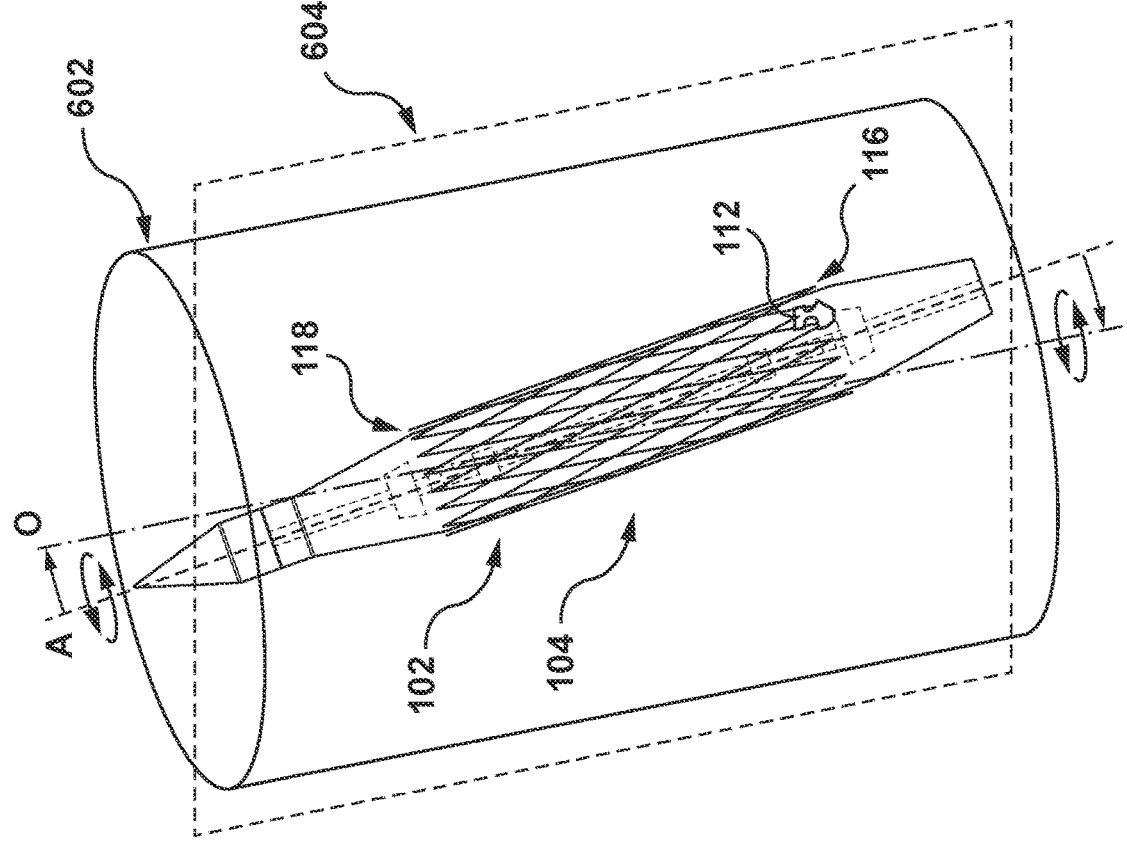

If the central axis, A, is not aligned with the desired orientation axis, O, other 2D shapes, not the defined 2D cross-sectional shape of the implant marker 112, will be visible in the image 606 captured in the image plane 604. For example, as illustrated in FIG. 6D, the implantable medical device 102 may be tilted, e.g., the central axis, A, is tilted at an angle relative to the desired orientation axis, O, and/or rotated about the central axis, A. As illustrated in FIG. 6F, other 2D cross-sectional shape may appear above the other in the image 606, which indicates the tilt and/or rotated. To correct the orientation, the operator of the delivery system 100 can move the implantable medical device 102 (e.g., tilt, rotate, etc.) until the defined 2D cross-sectional shape appears.

While FIG. 6A illustrates only a single implant marker 112, one skilled in the art will realize that additional implant markers 112 can be positioned on the implantable medical device 102. Likewise, while the implant marker 112 is formed in the defined 2D cross-sectional shape as illustrated, one skilled in the art will realize that the implant marker 112 can be formed in any shape that produces distinct 2D images depending on the angle of the image plane.

The above description of FIGS. 3A-3G, 4A-4G, 5A-5B, and 6A-6B discusses various examples of arrangement of the implant markers 112. One skilled in the art will realize that any of the arrangement described in FIGS. 3A-3G, 4A-4G, 5A-5B, and 6A-6B can be used in combination in the delivery system 100. Moreover, one skilled in the art will realize that one or more proximal alignment markers 108 and one or more distal alignment markers 110 can be used in the arrangement described in FIGS. 3A-3G, 4A-4G, 5A-5B, and 6A-6B.

FIG. 7 illustrates a method 700 of operating of the delivery system 100 utilizing one or more proximal alignment markers 108, one or more distal alignment markers 110, and one or more implant markers 112 in accordance with an embodiment hereof. One skilled in the art will realize that FIG. 7 illustrates one example of steps that can be performed and that existing steps illustrated in FIG. 7 may be removed and/or additional steps may be added to the method 700.

In step 702 an image plane of an imaging device is aligned with anatomy at a target site. For example, as discussed above with reference to FIGS. 2A-2C, the imaging device 200, producing images, can be aligned with the anatomy of the patient (e.g., an annulus) such that an aligned image plane of the imaging device 200 is positioned to be parallel to a desired orientation axis, O.

In step 704, an implantable medical device is delivered to the target site. In embodiments, the implantable medical device 102 can be loaded onto the delivery system 100, which is then utilized to deliver the implantable medical device to the target site. In embodiments, the implantable medical device 102 includes the frame 104 and the medical implant 106.

For example, the implantable medical device 102 can include a frame and/or stent as the frame 104 and a replacement heart valve as the medical implant 106. Delivery of the implantable medical device 102 can be accomplished via any type of procedure utilized to install medical devices in patients. For example, if the implantable medical device includes a replacement heart valve, delivery of the implantable medical device 102 by the delivery system 100 can be accomplished via a percutaneous transfemoral approach or a transapical approach directly through the apex of the heart via a thoracotomy, or may be positioned within the desired area of the heart via different delivery methods known in the art for accessing heart valves. During delivery, the frame 104 remains compressed until it reaches a target site, e.g., a diseased native heart valve.

In step 706, the implantable medical device is positioned in an axial direction at the target site. In embodiments, the alignment markers (e.g., proximal alignment markers 108 and distal alignment markers 110) can be utilized to position the implantable medical device 102 in the axial direction.

For example, in the images captured by the imaging device, the proximal alignment markers 108 and the distal alignment markers 110 provide a visual alignment reference for aligning the implantable medical device 102 in the axial direction along a central axis, A (as illustrated in FIG. 1A). One or more proximal alignment markers 108 and one or more distal alignment markers 110 are positioned at a location or locations that indicate an expanded location of a proximal end 116 and a distal end 118 of the frame 104. When the frame 104 is fully expanded, one or more proximal alignment markers 108 indicates a relative position, P, of the proximal end 116 in the axial direction along the central axis, A. Likewise, one or more distal alignment markers 110 indicates a relative position, D, of the distal end 118 in the axial direction along the central axis, A. As the operator of the delivery system 100 views the images captured by the imaging system, the operator can position the one or more proximal alignment markers 108 and/or the one or more distal alignment markers 110 to align with a desired location of the implantable medical device when expanded. Using the visual reference points, an operator of the delivery device 100 can position the implantable medical device 102 to ensure the implantable medical device 102 properly engages with native structure of at the target site once the frame 104 is expanded.

In step 708, an orientation of the implantable medical device is aligned at the target site. In embodiments, the implant markers 112 operate solely or in combination to provide visual references to an orientation of the implantable medical device 102 relative to the native structure of the target site of the implantable medical device 102 is being installed.

For example, as discussed above in FIGS. 3A-3G, the implantable medical device 102 can include 4 implant markers 112 to assist in the orientation (e.g., tilt, rotations, axial alignment, etc.) of the implantable medical device 102. In embodiments, if the image plane 304 is aligned with the native anatomy as desired, the appearance of the pattern 308 indicates the implant plane 301 is approximately perpendicular to image plane 304 indicating proper orientation (e.g., indicating proper tilt) of the implantable medical device 102, as illustrated in FIG. 3C. As such, the central axis, A, of the implantable medical device 102 is aligned with the desired orientation axis, O. If the central axis, A, is not aligned with the desired orientation axis, O, other patterns, not the predetermined pattern 308 of the 4 implant markers 112, will be visible in the image 306 captured in the image plane 304. For example, as illustrated in FIG. 3D, the implantable medical device 102 may be tilted, e.g., the central axis, A, is tilted at an angle relative to the desired orientation axis, O. As illustrated in FIG. 3E, a pattern 310, e.g., the 4 implant markers 112 scattered and not in a line, may appear in the image 306, which indicates the tilt. To correct the orientation, the operator of the delivery system 100 can move the implantable medical device 102 (e.g., tilt) until the predetermined pattern 308 appears.

In embodiments, the 4 implant marker 112 can be utilized to align the rotational orientation (e.g., the rotation about the central axis, A) of the implantable medical device 102. For example, if the 4 implant markers 112 are placed on the frame 104 at positions that reference proper rotational orientation and 1 of the 4 implant markers 112 obscures another of the implant markers 112, the predetermined pattern indicates proper rotational orientation of the implantable medical device 102, as illustrated in FIG. 3C. Likewise, for example, as illustrated in FIG. 3F, the implantable medical device 102 may be rotated about the central axis A. As such, as illustrated in FIG. 3G, a pattern 314 may appear in the image 306, e.g., the 4 implant markers 112 aligned in a line, but all or a portion of all the 4 implant markers 112 are visible, indicating the rotation. To correct the orientation, the operator of the delivery system 100 can move the implantable medical device 102 (e.g., rotate) until the predetermined pattern 308 appears.

In step 710, the implantable medical device is deployed at the target site. In embodiments, the implantable medical device 102 can be deployed. In embodiments, the implantable medical device 102 can be deployed using the expansion device 126 of the delivery system 100. For example, the operator of the delivery system 100 can activate the expansion device 126 (e.g., inflate a balloon, release tension in one or more sutures or bands, or manipulate one or more wires or rods) in order to radially expand the frame 104 in situ. The inner shaft 114 is then removed and the implantable medical device 102 remains deployed within the native target heart valve.

In some embodiments, if the medical implant 106 is a replacement heart valve, the medical implant 106 is configured to block flow in one direction to regulate flow therethrough via valve leaflets that may form a bicuspid or tricuspid replacement valve. When the implantable medical device 102 is deployed within the valve annulus of a native heart valve, the frame 104 of the implantable medical device 102 is configured to be radially expanded within native valve leaflets of the defective valve, to thereby retain the native valve leaflets in a permanently open state. In some embodiments, the implantable medical device 102 is configured for replacement for an aortic valve such that an inflow end of the implantable medical device 102 extends into and anchors within the aortic annulus of a patient's left ventricle, while an outflow end of the implantable medical device 102 is positioned within the aortic sinuses.

FIGS. 8A-8E illustrate a transcatheter valve prosthesis 800, which is a non-limiting example of an implantable medical device 102, in which a radially-expandable stent 802 thereof incudes one or more inflow markers 860, and an first outflow marker 870, according to another embodiment hereof. In embodiments, the inflow markers 860 and the first outflow marker 870 can be utilized in orientation (e.g., axial/annular alignment, tilt alignment, circumferential (rotational) alignment, etc.) of the transcatheter valve prosthesis 800, in situ, as discussed in detail below.

One skilled in the art will realize that FIGS. 8A-8E illustrate one example of an implantable medical device and that existing components illustrated in FIGS. 8A-8E may be removed and/or additional components may be added. Additionally, while the transcatheter valve prosthesis 800 is described below as including the one or more inflow markers 860) and the first outflow marker 870, one skilled in the art will realize that the transcatheter valve prosthesis 800 can include additional markers, for example, any of the markers described herein. Moreover, while examples of operations and advantages of the transcatheter valve prosthesis 800, one or more inflow markers 860, and an first outflow marker 870) are discussed below, one skilled in the art will realize any of the operations and processes described above can be performed using the transcatheter valve prosthesis 800.

Figure 8A:
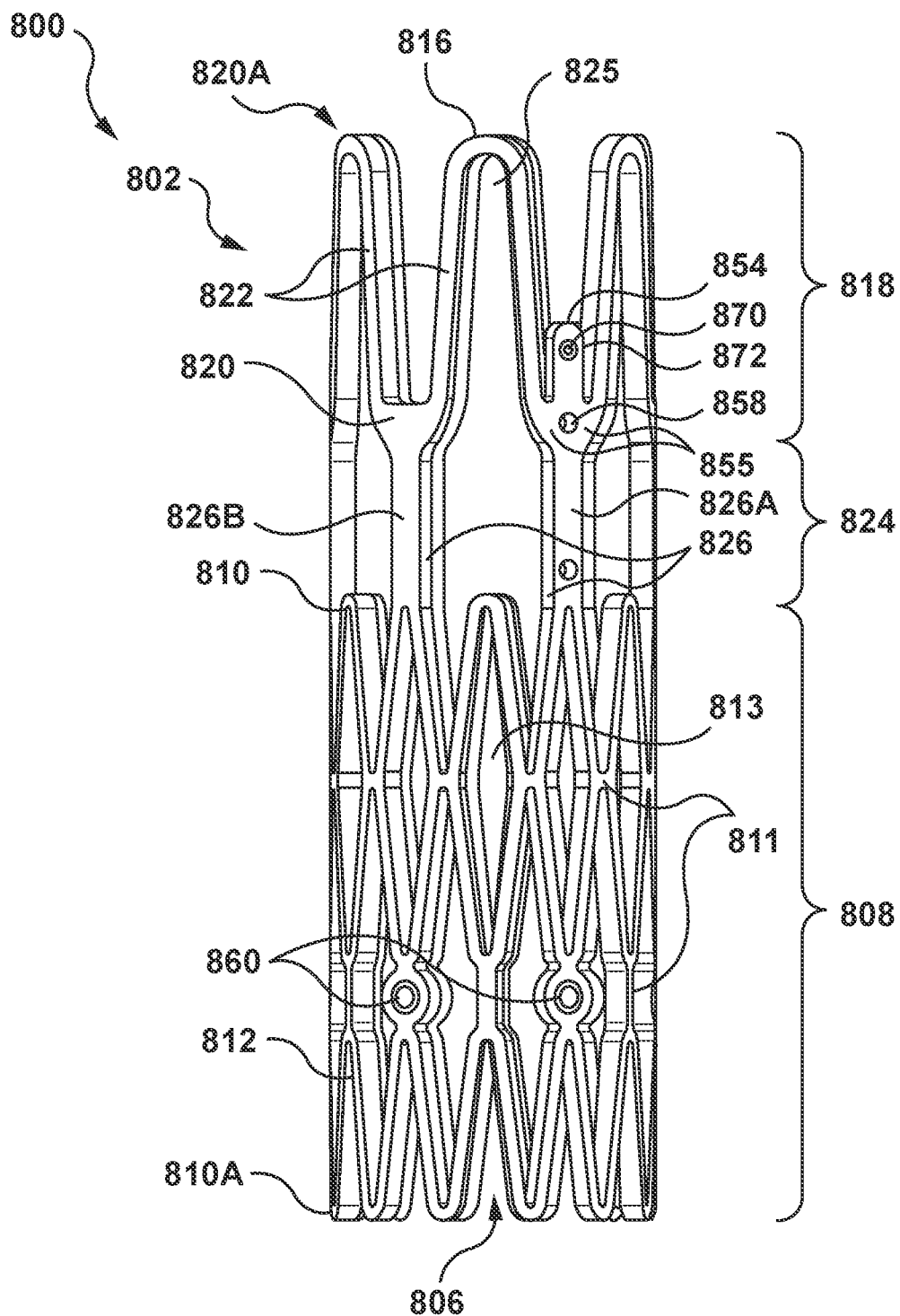
FIGS. 8A-8E illustrate a transcatheter valve prosthesis in accordance with an embodiment hereof.
Figure 8B:
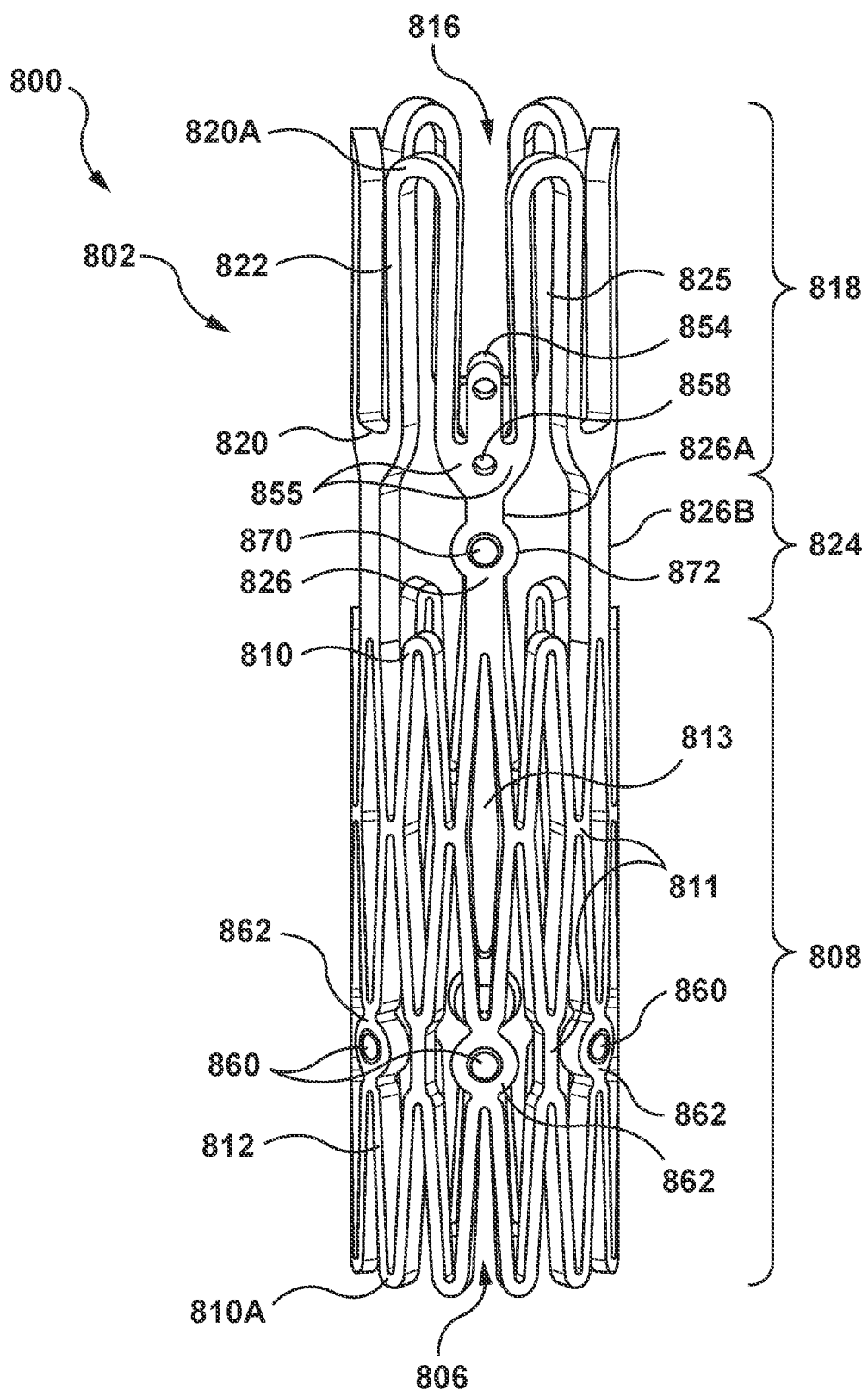
Figure 8C:
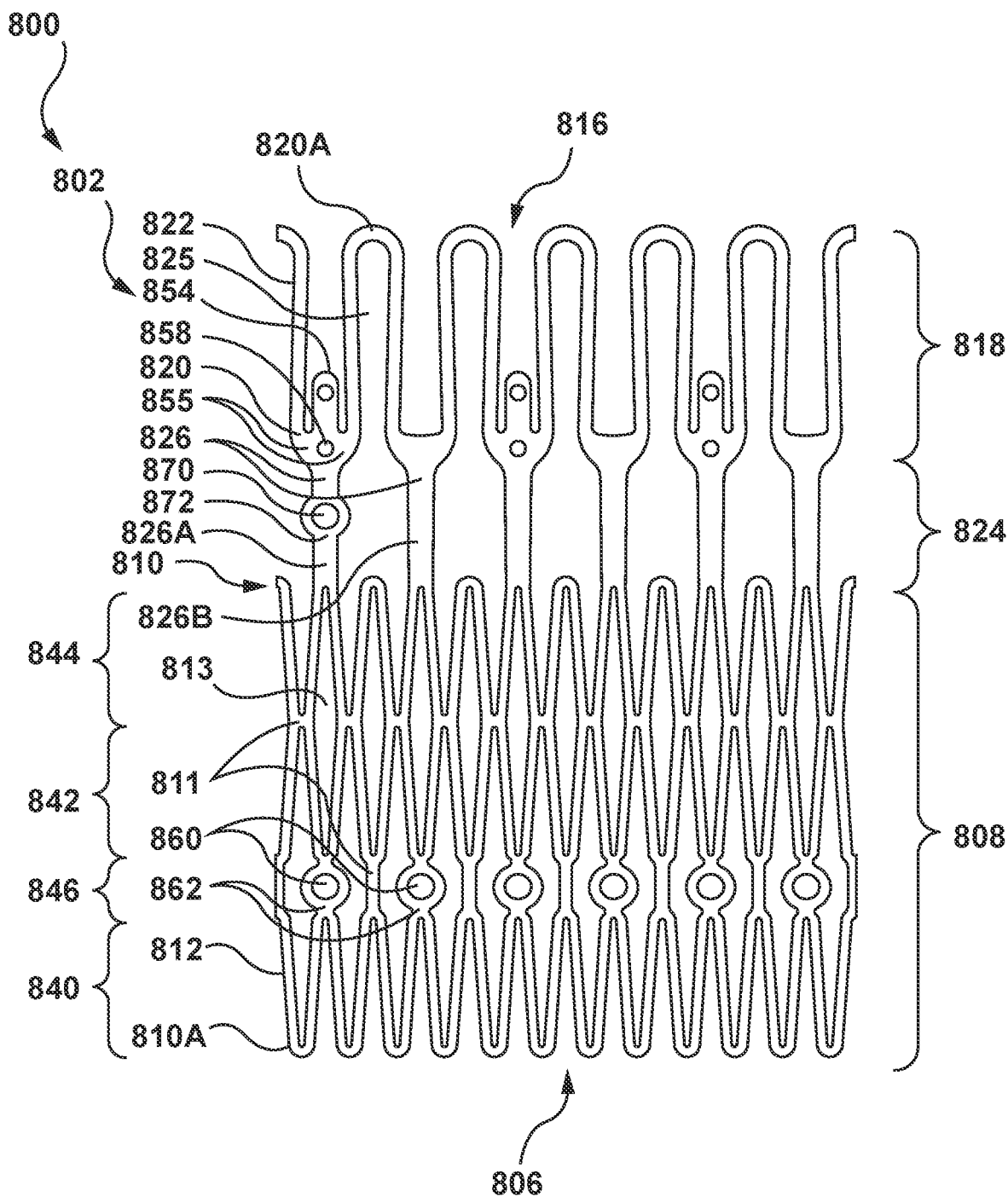
Figure 8D:
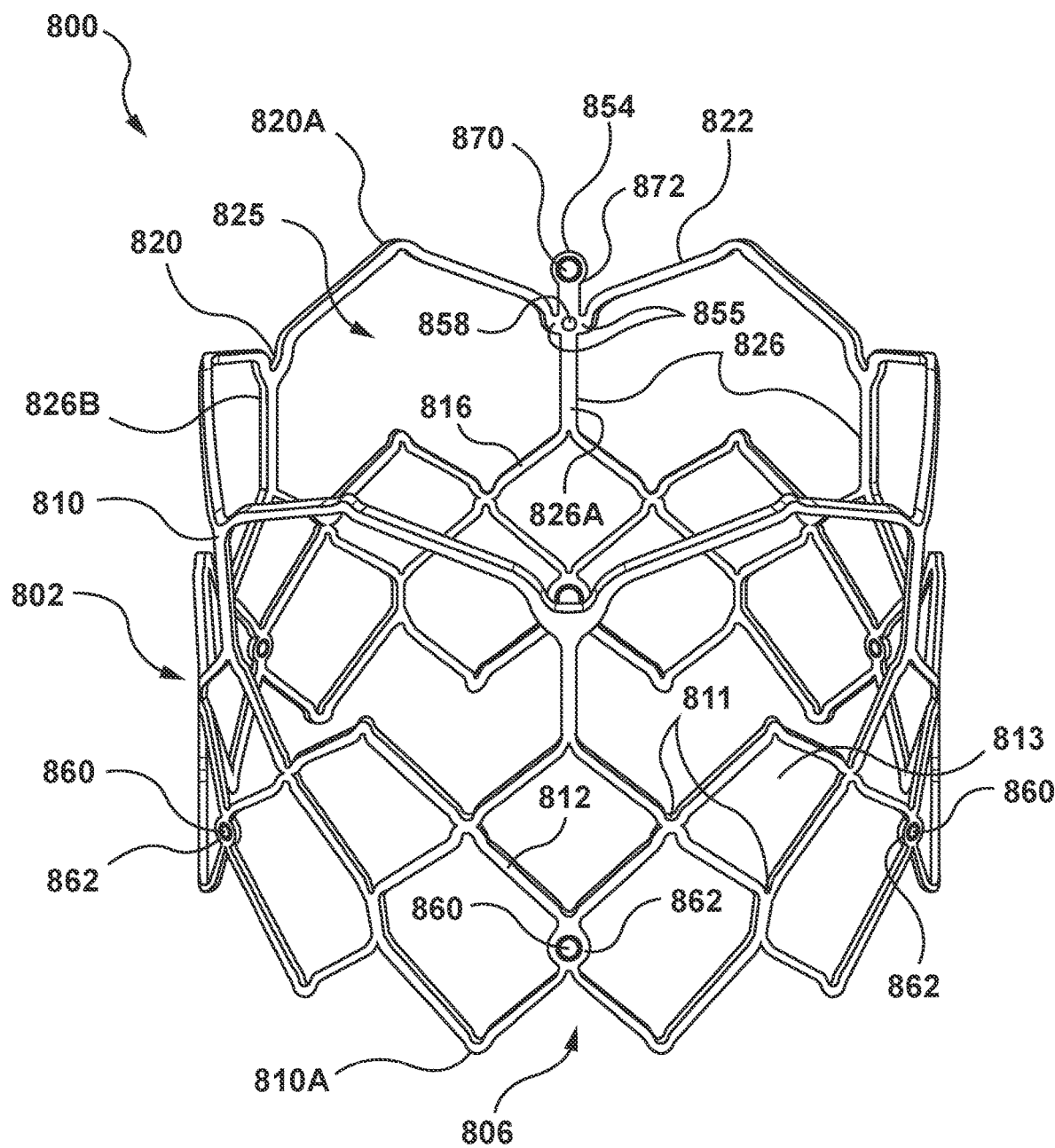
Figure 8E:
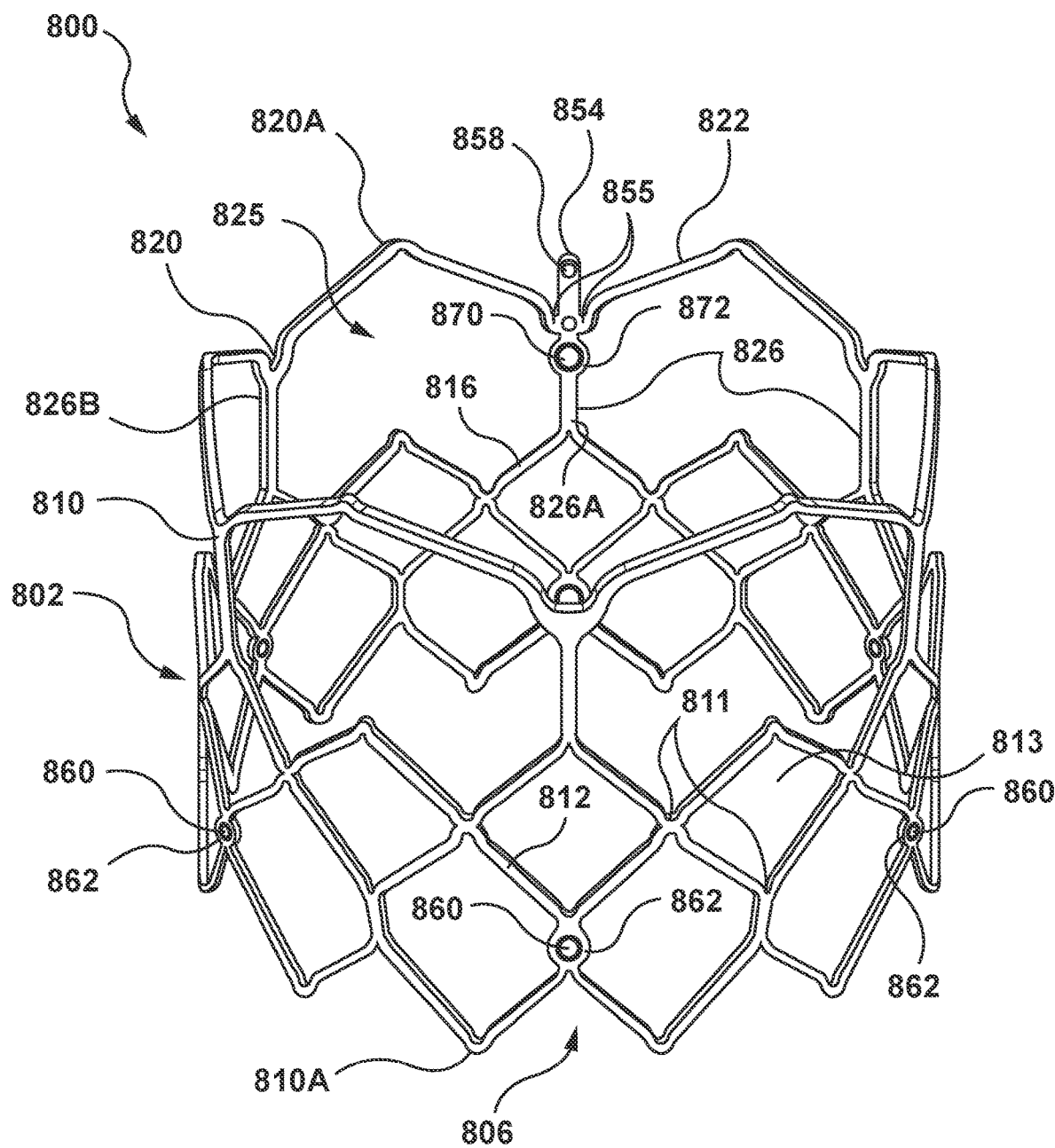

The stent 802 has a non-expanded or crimped configuration, which is shown in a side view of FIGS. 8A and 8B, and an expanded configuration, which is shown FIGS. 8D and 8E. Non-expanded or crimped configuration as used herein refers to the configuration of the stent 802 after crimping, for example, onto a balloon of a balloon catheter for delivery. The stent 802 is mechanically or balloon expandable. As such, the stent 802 can be made from a plastically deformable material such that, when expanded by a dilatation balloon, the stent 802 maintains its radially expanded configuration after balloon deflation. The stent 802 can be formed from stainless steel or other suitable metal, such as platinum iridium, cobalt chromium alloys such as MP35N, or various types of polymers or other materials known to those skilled in the art, including said materials coated with various surface deposits to improve clinical functionality.

The stent 802 can be configured to be rigid such that it does not deflect or move when subjected to in-vivo forces, or such that deflection or movement is minimized when subjected to in-vivo forces. In an embodiment, the radial stiffness (i.e., a measurement of how much the stent 802 deflects when subjected to in-vivo forces) of the stent 802 can be between 80 N/m and 120 N/m, and the radial stiffness of the stent 802 scaled across the deployed height thereof is approximately 5 N/mm$^2$. In an embodiment, the radial stiffness of the stent 802 can be greater than 100 N/m. Further, in an embodiment, the device recoil (i.e., a measurement of how much the stent 802 relaxes after balloon deployment) can below 15% and the approximate recoil after deployment is between 0.5 mm and 2 mm. Further, in an embodiment, the device crush or yield (i.e., the radial force at which the stent 802 yields) can be approximately 200 N. While the above describes examples of radial stiffness for the stent 802, one skilled in the art will realize that the stent 802 may have any radial stiffness as required by a given application and/or governed by the design and construction of the stent 802.

The stent 802 can be formed from a unitary frame or scaffold having an inflow portion 808, an outflow portion 818, and a transition portion 824 bridging, connecting, or otherwise extending between the inflow portion 808 and the outflow portion 818. The stent 802 can be a generally tubular component defining a central lumen or passageway and can have an inflow or proximal end 806 and an outflow or distal end 816. When expanded, a diameter of the inflow end 806 of the stent 802 can be the same as a diameter of the outflow end 816 of the stent 802. The stent 802 can be formed by a laser-cut manufacturing method and/or another conventional stent forming method as would be understood by one of ordinary skill in the art. The cross-section of the stent 802 can be trapezoidal, circular, ellipsoidal, rectangular, hexagonal, square, or other polygonal shape, although at present it is believed that trapezoidal, circular or ellipsoidal may be preferable when utilized with the replacement of an aortic valve. FIG. 8C shows an open, flat view of an example of the stent 802 with a circular or ellipsoidal example of the unitary frame.

A prosthetic valve (not shown) is disposed within and secured to at least the transition portion 824 of the stent 802. In addition, the prosthetic valve can also be disposed within and secured to the inflow portion 808 of the stent 802 and/or the outflow portion 818 of the stent 802. One skilled in the art will realize that the prosthetic valve can be disposed within and secured to one or more of the inflow portion 808, outflow portion 818, or the transition portion 824, for example, depending on the design and construction of the prosthetic valve and/or the design and construction of the stent 802

The inflow portion 808 can be formed proximate to the inflow end 806 of the stent 802. The inflow portion 808 of the stent 802 may be formed with crowns 810, struts 812, and nodes 811 formed at an intersection of pairs of struts 812. The inflow end 806 of the tubular stent 802 can include a total of twelve endmost inflow crowns 810A. Pairs of the struts 812, coupled at the nodes 811, form cell 813 that define an open space in the stent 802.

The outflow portion 818 can be formed proximate to the outflow end 816 of the stent 802. The outflow portion 818 can be configured in a shape that forms a central lumen or passageway, for example, a ring. The outflow portion 818 can include a plurality of crowns 820 and a plurality of struts 822 with each crown 820 being formed between a pair of opposing struts 822. Each crown 820 can be a curved segment or bend extending between opposing struts 822. A series of endmost outflow crowns 820A are formed at the outflow end 816 of the stent 802. For example, the outflow end 816 of the stent 802 can have a total of six endmost outflow crowns 820A.

The transition portion 824 bridges, connects, or otherwise extends between the inflow portion 808 and the outflow portion 818. The transition portion 824 can includes a minimum of three axial frame members 826, each axial frame member 826 extending between an outflow crown 820 of the outflow portion 818 and a crown 810 of the inflow portion 808. Each axial frame member 826 can be connected to a crown 820 of the outflow portion 818 and connected to a crown 810 of the inflow portion 808. The axial frame members 826 can be substantially parallel to the central longitudinal axis of the stent 802. Each axial frame member 826 can be disposed approximately halfway between a pair of adjacent endmost outflow crowns 820A. While the stent 802 has been described as including a transition portion 824, one skilled in the art will realize that the transition portion 824 may form a portion of the inflow portion 808 and/or the outflow portion 818.

In an embodiment, the transition portion 824 can include up to six axial frame members 826, with three of the axial frame members 826 being commissure posts 826A and three of the axial frame members 826 being axial struts 826B being alternatingly positioned, as illustrated, for example, in FIG. 8C. The commissure posts 826A can be circumferentially spaced apart and aligned with and attached to a respective commissure of the three leaflets of the prosthetic valve, and the axial struts 826B can be disposed between adjacent commissure posts 826A. The axial frame members 826 aid in valve alignment and coaptation. More particularly, the axial frame members 826 reinforce or strengthen the commissure region of the prosthetic valve by shaping the leaflets and supporting the leaflets during opening and closing thereof, and thus provide more reliable leaflet coaptation. In addition, the axial frame members 826 maximize symmetrical cell expansion.

In this embodiment, the endmost outflow crowns 820A are not connected to the axial frame members 826 but rather may be considered to be free or unattached while the remaining outflow crowns 820 of the outflow portion 818 are connected to the axial frame members 826 and disposed closer to the inflow end 806 than the endmost outflow crowns 820A. In the embodiment shown, the stent 802 includes a single row of struts 822 and crowns 820 coupled to the axial frame members 826 and defining the outflow end 816 of the stent 802. Further, in the embodiment shown, exactly two struts 822 and a single crown 820 of the outflow portion 818 are disposed between adjacent axial frame members 826. Such an arrangement can provide a series of six endmost cells 825 formed at the outflow portion 818 of the stent 802. Each endmost cells 825 can define an open space in the stent 802, which is formed in any type of shape, in the radially expanded configuration (see FIGS. 8D-8E). More particularly, each endmost cells 825 can be defined by two adjacent struts 822 of the outflow portion 818, four adjacent struts 812 of the inflow portion 808, and two adjacent axial frame members 826 of the transition portion 824. The endmost cells 825 of the outflow portion 818 are relatively larger than the cells 813 of the inflow portion 808 to improve access to the coronary arteries. More particularly, the endmost cells 825 of the outflow portion 818 can be configured to be of sufficient size to be easily crossed with a coronary guide catheter into either the right coronary artery or the left main coronary artery once the transcatheter valve prosthesis 800 is deployed, in situ.

In one embodiment, the inflow portion 808 can include exactly three rows of struts 812 and crowns 810 between the axial frame members 826 and the inflow end 806 of the stent 802. Further, in this embodiment, the four struts 812 and three crowns 810 can be disposed between adjacent axial frame members 826. In an embodiment, a height or length of the stent 802 in the expanded configuration can be between 14 and 23 mm, the height being measured from the most proximal part thereof to the most distal part thereof, and a diameter of the stent 802 in the expanded configuration can be between 18 and 31 mm. For example, an expanded 21 mm diameter device would be 15 mm in height. An expanded 30 mm diameter device would have a 21 mm height. One skilled in the art will realize that the above configuration of the inflow portion 808 is one example of a configuration of the inflow portion 808 and that the inflow portion 808 can include fewer or additional rows of struts 812 and crowns 810. Likewise, one skilled in the art will realize that each row can include fewer or additional numbers of struts 812 and crowns 810. Additionally, one skilled in the art will realize that the ranges of the height and diameter of the stent 802 are examples and that the height and diameter of the stent 802 may vary based on an amount of expansion of the stent 802, for example, as required by a given application and/or governed by the design and construction of the stent 802

In an embodiment, the axial frame members 826 can include commissure posts 826A that are formed to have an axial length greater than the axial struts 826B. In this embodiment, a first end of each of the axial struts 826B can be coupled, to a pair of struts 812. A second end of each of the axial struts 826B can be coupled to a pair of the struts 822. A first end of each of the commissure posts 826A can be coupled to a pair of the struts 812. Because the commissure posts 826A are longer than the axial struts 826B, pairs of struts 822 are coupled to the commissure posts 826A at side portions 855 of the commissure posts 826A. The location of the connection to the side portions 855 is spaced a distance, in the direction of the inflow end 806, from the second end of the commissure posts 826A. In other words, each commissure posts 826A can be a relatively stiff, axial segment or planar bar having a first end connected to a pair of struts 812 at a crown 820 of the inflow portion 808 and having an unattached or free second end. As such, the connection of the struts 822 to the side portions 855 defines an outflow portions 854 of the commissure posts 826A, which is positioned in the outflow portion 818.

The outflow portions 854 can be configured as support features that allow for lengthened commissure posts 826A to further reinforce or strengthen the commissure region of the transcatheter valve prosthesis 800. Each of the outflow portions 854 can extend into the outflow portion 818 of the stent 802 to allow for lengthened commissure posts 826A without increasing the overall height of the transcatheter valve prosthesis 800. More particularly, the stent 802 can include a total of three commissure posts 826A, which include three outflow portions 854. The commissure posts 826A, which include the outflow portions 854, can extend substantially parallel to the central longitudinal axis of the stent 802 and are circumferentially spaced apart from each other. The commissure posts 826A, which include the outflow portions 854, can include holes or openings 858 formed therein configured to attach a respective commissure of the three leaflets of the prosthetic valve to the stent 802. Additionally, in some embodiments, the commissure posts 826A, which include the outflow portions 854, can include one or more holes or openings to support alignment markers, as described further below. One skilled in the art will realize that the above configuration of the outflow portion 818 is one example of a configuration of the outflow portion 818 and that the outflow portion 818 can include fewer or additional numbers of commissure posts 826A, axial struts 826B, crowns 820, and struts 822.

As discussed above, the commissure posts 826A can be formed to be lengthened relative to the axial struts 826B. The commissure posts 826A can reduce stresses observed at the commissure region during valve loading by spreading out such stresses across a larger area. More particularly, as compared to self-expanding valve stents, balloon expandable valves stents are stiffer and stronger but therefore may place more stress on the valve leaflets attached thereto attached to the stent 802. The valve leaflets, which are often formed from tissue, are more durable when the portion of the stent to which they are attached is more flexible, but such stent flexibility may be detrimental to stent fatigue. As such, the commissure posts 826A achieve a balance between stent durability and tissue durability because the stent 802 maintains its strength and durability while the lengthened commissure supports improve or increase tissue durability of the valve leaflets by stress relief from the lengthened commissure supports.

Further, the performance of the transcatheter valve prosthesis 800 may be enhanced by the lengthened commissure posts 826A without increasing the overall height of the transcatheter valve prosthesis 800. For example, in the unexpanded or compressed state, as illustrated in FIGS. 8A and 8B, the outflow portions 854 of the commissure posts 826A extend into the outflow portion 818, but do not extend beyond the endmost outflow crowns 820A. In the expanded or uncompressed state, as illustrated in FIGS. 8D and 8E, the outflow portions 854 of the commissure posts 826A extend into the outflow portion 818, but do not extend beyond the endmost outflow crowns 820A. In other words, the length of the commissure post 826A is increased without increasing the length of the transition portion 824 and the overall height of the transcatheter valve prosthesis 800. A relatively short or minimized overall height is desirable to increase coronary access and improve system deliverability.

In another embodiment hereof (not shown), the axial struts 826B of the stent 802 can be replaced with the commissure posts 826A, which include the outflow portions 854. Inclusion of the commissure posts 826A, which include the outflow portions 854, may aid in valve alignment and coaptation. Symmetrical cell expansion ensures that the stent crimps well onto a balloon of a balloon catheter for delivery. Poor crimp quality may lead to portions of the stent overlapping when crimped, which in turn may cause tissue damage to the valve leaflets of the prosthetic valve during the crimping process.

In embodiments, to ensure the proper placement in the native anatomy of a subject, the transcatheter valve prosthesis 800 can include the one or more inflow markers 860 and the first outflow marker 870. In embodiments, the inflow markers 860 can be positioned towards the inflow end 806 of the stent 802 in the inflow portion 808. As illustrated in FIG. 8C, the stent 802 can include three rows of the struts 812: a first row 840 of the struts 812 formed proximate to the inflow end 806, a second row 842 of the struts 812 formed between the first row 840 and a third row 844, and the third row 844 of struts 812 formed proximate to the transition portion 824. In an embodiment, the inflow markers 860 can be positioned at the intersection 846 of the first row 840 and the second row 842. For example, as illustrated in FIG. 8C, the inflow markers 860 can be positioned at every other intersection of a pair of the struts 812 of the first row 840 and the second row 842. The inflow markers 840 are circumferentially aligned with each other around a circumference of the stent 802.

While FIG. 8C illustrates one example of the positioning and number of inflow markers 860, one skilled in the art will realize that the stent 802 can include any number of inflow markers 860, positioned at any location within the inflow portion 808. For example, the inflow markers 860 can be portioned on the struts 812. Likewise, for example, the inflow markers 860 can be asymmetrically aligned, circumferentially, around a circumference of the stent 802, e.g., with different circumferential distances between the inflow markers 860. Additionally, for example, the inflow markers 860 can be positioned at different distances from the inflow end 806.

In embodiments, the inflow markers 860 can be formed in any shape to assist in the alignment of the transcatheter valve prosthesis 800. In embodiments, as illustrated in FIGS. 8A-8E, the inflow markers 860 can be formed having a circular cross-sectional shape. In other embodiments, the inflow markers 860 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the inflow markers 860 may be provided to provide a benefit for a given application.

In embodiments, the inflow markers 860 include radiopaque or other material that allow the inflow markers 860 to be detected and/or viewed during the installation of the transcatheter valve prosthesis 800. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc.

In embodiments, the inflow markers 860 can be attached to the stent 802 within a containment member 862. The containment member 862 can be configured as a hollow structure or opening in the stent 802 which can receive the inflow markers 860. In an embodiment, the containment member 862 can be open to the interior and exterior of the stent 802, thereby allowing the inflow markers 860 to be exposed to the interior and exterior of the stent 802 and increasing visibility at multiple angles. In some embodiments, the containment member 862 can be open only to the interior or exterior of the stent 802, thereby forming a cavity or depression in the stent 802.

The containment member 862 can be configured in a shape that matches a shape of the inflow markers 860. For example, as illustrated in FIGS. 8A-8C, if the inflow markers 860 have a circular cross-sectional shape, the containment member 862 can be define a cavity that is circular, e.g., a hollow ring. In some embodiments, the containment member 862 need not extend from an exterior or an interior of the stent 802 such that the containment member 862 includes a surface aligned with the exterior surface or interior surface of the stent 802. In some embodiments, the containment member 862 may extend from an exterior or an interior surface of the stent 802.

In some embodiments, when placed in the containment member 862, one or more the inflow markers 860 may be contained within the containment member 862 and may be recessed from an exterior and/or an interior surface of the stent 802. In some embodiments, when placed in the containment member 862, one or more the inflow markers 860 may be contained within the containment member 862 and may be flush with an exterior and/or an interior surface of the stent 802. In some embodiments, when placed in the containment member 862, one or more the inflow markers 860 may be extend from the containment member 862 and may be extend from an exterior and/or an interior surface of the stent 802.

In embodiments, the inflow marker 860 can be attached to, positioned in, and/or formed in the containment member 862 utilizing any type of processes and/or procedure. In an embodiment, radiopaque beads or spheres (or lines of radiopaque beads or spheres) may be press fit, swaged, interference fit, etc. into the containment member 862. In an embodiment, the stent 802 may not include a containment member 862. In this embodiment, the inflow markers 860 may be attached and/or applied to the stent 802. For example, the inflow markers 860 may comprise radiopaque bands that are attached to the stent 802. Likewise, for example, the inflow markers 860 may be formed by applying radiopaque materials to the stent 802 in any shape. One skilled in the art will realize that the inflow markers 860 may be attached to or formed on the stent 802 utilizing any processes as required by the design of the stent 802 and/or application of the transcatheter valve prosthesis 800.

In any embodiment, the inflow markers 860 can be formed to dimensions such that the inflow markers 860 do not affect the operation of the transcatheter valve prosthesis 800. For example, the inflow markers 860 can be formed to not extend beyond the exterior diameter of the stent 802 or extend into the central lumen of the stent 802, e.g., having a radial depth that is equal to or less than the radial depth of the struts 812. In an embodiment, the inflow markers 860 can have a circular cross-sectional shape with a diameter ranging between approximately 0.5 mm and 1.0 mm, for example, approximately 0.8 mm. In this embodiment, the containment member 862 can have a circular cross-sectional shape with a diameter ranging between approximately 0.5 mm and 1.0 mm, for example, approximately 0.8 mm. In another embodiment, the inflow markers 860 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm. In this embodiment, the containment member 862 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm.

In embodiments, the stent 802 can include any number of the inflow markers 860. In an embodiment, the stent 802 can include one or more inflow markers 860 positioned at different locations of the intersection 846 of the first row 840 of struts 812 and the second row 842 of the struts 812. In another embodiment, the stent 802 can include six (6) inflow markers 860 positioned at alternating locations of the intersection 846 of the first row 840 of struts 812 and the second row 842 of struts 812. In the embodiment, the inflow markers 860 form a ring of distinct marker points around the circumference of the stent 802. where each distinct marker point is equal distance from the inflow end 806. One skilled in the art will realize that the stent 802 may include any number of the inflow markers 860, which are positioned at any location within the inflow portion 808. The inflow markers 860 are preferably located at the lengthwise location of the stent 802 that is desired to be aligned with the annulus of the native heart valve when the transcatheter valve prosthesis 800 is deployed at the native heart valve. For example, inflow markers 860 allows for better depth positioning of the transcatheter valve prosthesis 800, in a crimped or compressed state, such that it can be more accurately deployed and reduce the incidence rate of permanent pacemaker (PPM) post-implantation.

In embodiments, the transcatheter valve prosthesis 800 can also include the first outflow marker 870 to assist with the alignment of the commissure posts 826A. The first outflow marker 870 can operate to assist in rotational orientation of the stent 802, as described below. Additionally, the first outflow marker 870 can operate as a guide for determining a front or rear location the first outflow marker 870 in 2D image during implantation, as described below. The first outflow marker 870 can be positioned towards the outflow end 816 of the stent 802 in the outflow portion 818 or the transition portion 824. In an embodiment, the first outflow marker 870) can be circumferentially aligned with one of the inflow markers 860, as illustrated in FIG. 8A or 8B.

In an embodiment, the first outflow marker 870 can be positioned on one of the outflow portions 854 of a commissure post 826A in the outflow portion 818. As illustrated in FIGS. 8A and 8D, the first outflow marker 870 can be attached to the stent 802 within a containment member 872 formed in one of the outflow portions 854. In embodiments, the first outflow marker 870 can be attached to the outflow portion 854 within a containment member 872. The containment member 872 can be configured as a hollow structure or opening in the outflow portion 854 which can receive the first outflow marker 870.

In another embodiment (not shown), the first outflow marker 870 can be attached to an exterior surface of the commissure post 856A at a location that does not affect the operation of the transcatheter valve prosthesis 800. For example, the first outflow marker 870 can be attached to a top surface of the outflow portion 854, proximal to the outflow end 816. In this example, the first outflow marker 870 can be configured not to extend beyond the exterior diameter of the stent 802 or extend into the central lumen of the stent 802, e.g., having a radial depth that is equal to or less than the radial depth of the outflow portion 854.

In another embodiment, the first outflow marker 870 can be positioned on the commissure posts 826A. As illustrated in FIGS. 8B, 8C, and 8E, the first outflow marker 870) can be attached to the stent 802 within a containment member 872 formed in a commissure post 826A. In this embodiment, the containment member 872 can be positioned at any location along the commissure post 826A, for example, proximal to the outflow portion 854, in the center of the commissure post 826, biased towards the inflow end 806, or at any location with the transition portion 824, and the like.

In any embodiment, the containment member 872 can be configured in a shape that matches a shape of the first outflow marker 870. For example, as illustrated in FIGS. 8A-8E, if the first outflow marker 870 have a circular cross-sectional shape, the containment member 872 can be define a cavity that is circular, e.g., a hollow ring. In some embodiments, the containment member 872 need not extend from an exterior or an interior of the outflow portion 854 and/or any location on the commissure post 826A such that the containment member 872 includes a surface aligned with the exterior surface or interior surface of the stent 802. In some embodiments, the containment member 872 may extend from an exterior or an interior surface of the outflow portion 854 and/or any location on the commissure post 826A. In some embodiment, the containment member 872 can be open to the interior and exterior of the stent 802, thereby allowing the first outflow marker 870 to be exposed to the interior and exterior of the stent 802 and increasing visibility at multiple angles. In some embodiments, the containment member 872 can be open only to the interior or exterior of the stent 802, thereby forming a cavity or depression in the outflow portion 854.

In some embodiments, when placed in the containment member 872, the first outflow marker 870 may be contained within the containment member 872 and may be recessed from an exterior and/or an interior surface of the outflow portion 854 and/or any location on the commissure post 826A. In some embodiments, when placed in the containment member 872, the first outflow marker 870 may be contained within the containment member 872 and may be flush with an exterior and/or an interior surface of the outflow portion 854 and/or any location on the commissure post 826A. In some embodiments, when placed in the containment member 872, the first outflow marker 870 may be extend from the containment member 872 and may be extend from an exterior and/or an interior surface of the outflow portion 854 and/or any location on the commissure post 826A.

In any embodiment, the first outflow marker 870 can be attached to, positioned in, and/or formed in the containment member 872 utilizing any type of processes and/or procedure. In an embodiment, radiopaque beads or spheres (or lines of radiopaque beads or spheres) may be press fit, swaged, interference fit, etc. into the containment member 872. In any embodiment, the stent 802 may not include a containment member 872. In this embodiment, the first outflow marker 870 may be attached and/or applied to the outflow portion 854 and/or any location on the commissure post 826A. For example, the first outflow marker 870 may comprise radiopaque bands that are attached to the outflow portion 854 and/or any location on the commissure post 826A. Likewise, for example, the first outflow marker 870 may be formed by applying radiopaque materials to the outflow portion 854 and/or any location on the commissure post 826A in any shape. One skilled in the art will realize that the first outflow marker 870 may be attached to or formed on the stent 802 utilizing any processes as required by the design of the stent 802 and/or application of the transcatheter valve prosthesis 800.

In any embodiment, the first outflow marker 870 can be formed in any shape to assist in the alignment of the transcatheter valve prosthesis 800. In embodiments, as illustrated in FIGS. 8A-8C, the first outflow marker 870 can be formed in a circular cross-sectional shape. In other embodiments, the first outflow marker 870 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the outflow marker may be provided to provide a benefit for a given application.

In any embodiment, the first outflow marker 870 include radiopaque or other material that allow the first outflow marker 870 to be detected and/or viewed during the installation of the transcatheter valve prosthesis 800. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc.

In any embodiment, the first outflow marker 870 can be formed to dimensions such that the first outflow marker 870 does not affect the operation of the transcatheter valve prosthesis 800. For example, the first outflow marker 870 can be formed to not extend beyond the exterior diameter of the stent 802 or extend into the central lumen of the stent 802, e.g., having a radial depth that is equal to or less than the radial depth of the commissure post 826A. In an embodiment, the first outflow marker 870) can have a circular cross-sectional shape with a diameter ranging between approximately 0.5 mm and 1.0 mm, for example, approximately 0.8 mm. In this embodiment, the containment member 872 can have a circular cross-sectional shape with a diameter ranging between approximately 0.5 mm and 1.0 mm, for example, approximately 0.8 mm. In another embodiment, the first outflow marker 870 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm. In this embodiment, the containment member 872 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm.

Figure 9B:
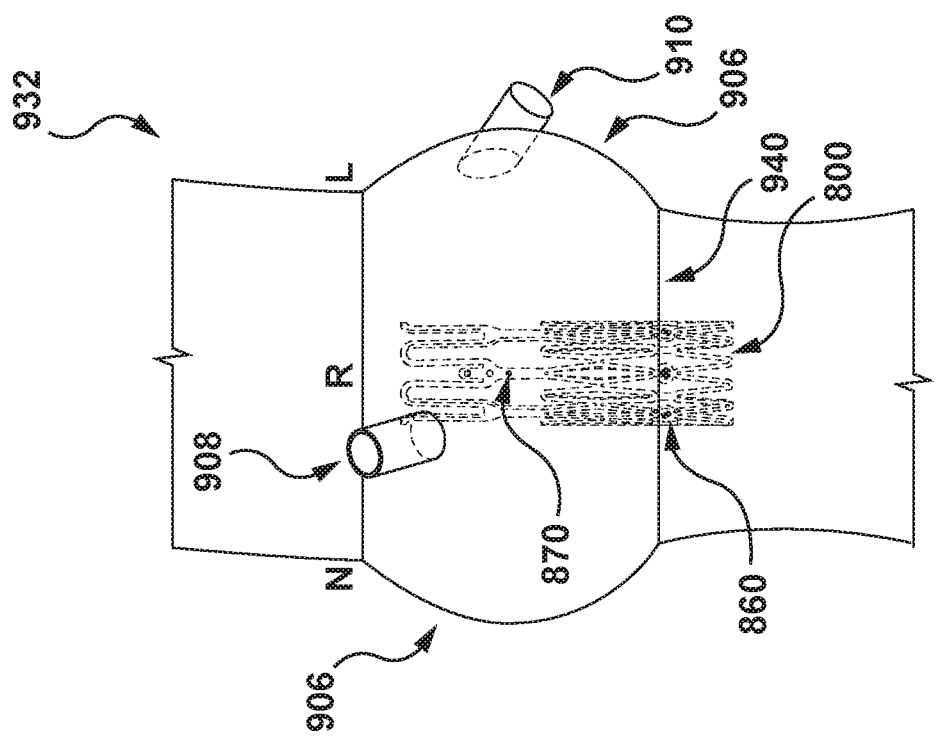
FIGS. 9A-9F illustrate various views of a target site for the transcatheter valve prosthesis of FIGS. 8A-8E in accordance with an embodiment hereof.
Figure 9A:
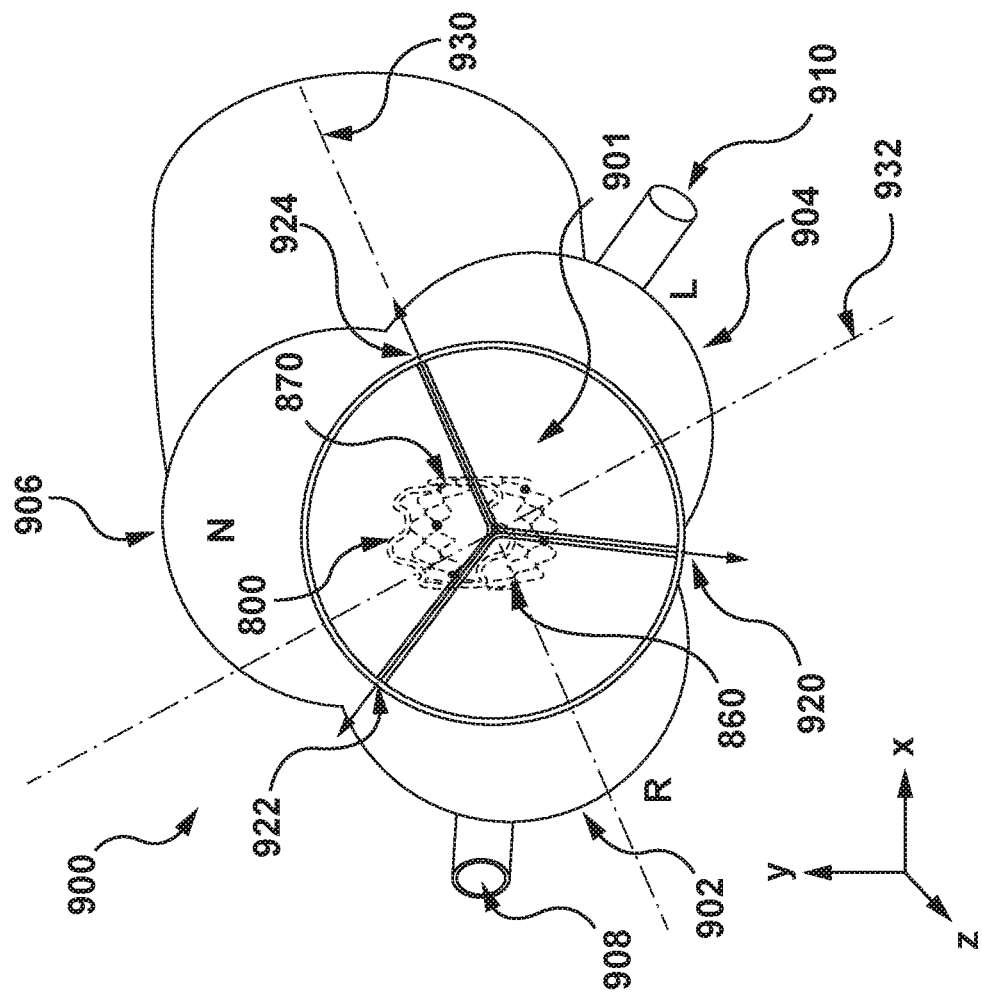
Figure 9C:
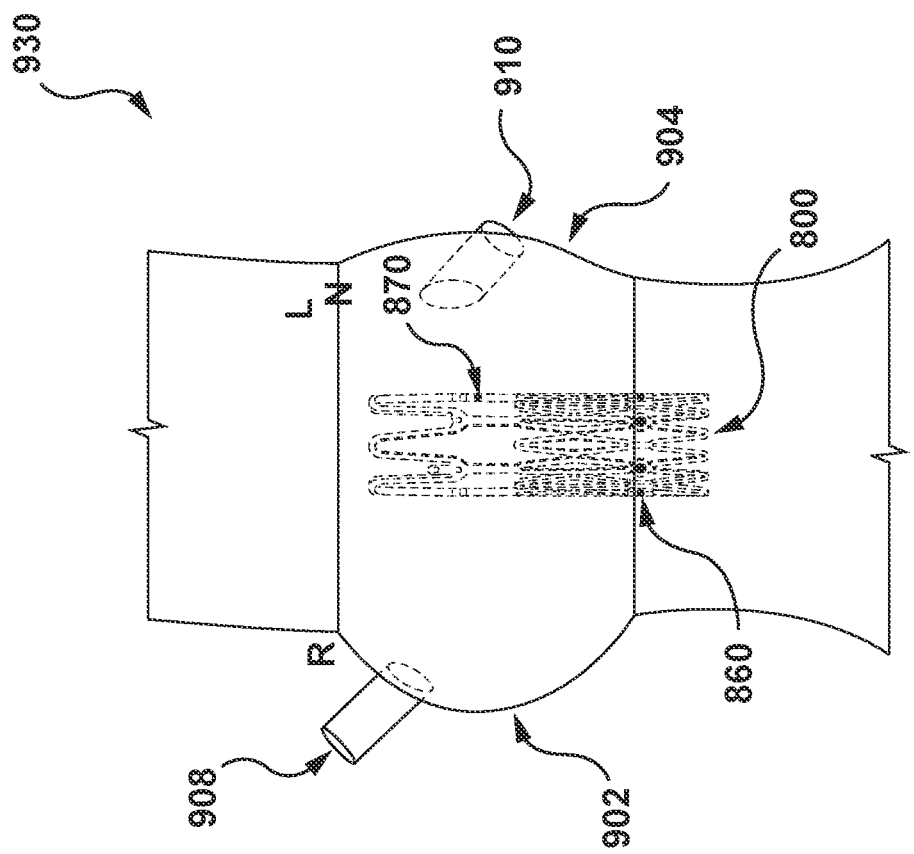

In embodiments, the inflow markers 860 and the first outflow marker 870 can be utilized in orientation (e.g., axial/annular alignment, tilt alignment, circumferential (rotational) alignment, etc.) of the transcatheter valve prosthesis 800, in situ, during installation as described below with reference to FIGS. 9A-9E. FIGS. 9A-9C illustrate various views of a target site 900, e.g., an aortic heart valve, of the transcatheter valve prosthesis 800. As illustrated in FIG. 9A, which is a 2-D annular view of the target site 900 taken perpendicular to an annulus 901, the target site 900 includes three valve cusps of the aortic root, the right coronary cusp 902, the left coronary cusp 904 and the non-coronary cusp 906. The region of the right coronary cusp 902 includes ostia of the right coronary artery 908. Likewise, the region of the left coronary cusp 904 includes ostia of the left main coronary artery 910.

When installing the transcatheter valve prosthesis 800, it is desirable to properly align the stent 802 within the target site 900. For example, the transcatheter valve prosthesis 800 needs to be properly aligned, axially/annularly, so that the transcatheter valve prosthesis 800 properly engages the native leaflets/tissue of the target site 900, e.g., the aortic annulus without causing conduction blockages by implanting too deep or causing an embolization of the transcatheter valve prosthesis 800 because it was implanted too high. Likewise, the transcatheter valve prosthesis 800 needs to be aligned circumferentially or rotationally. When being positioned, in situ, it is very important to avoid blocking the ostia of the right coronary artery 908 and/or the left main coronary artery 910. Proper circumferential or rotational orientation within the target site 900 reduces the risk of blocking coronary access.

As illustrated in FIG. 9A, the right coronary cusp 902, the left coronary cusp 904, and the non-coronary cusp 906 include commissure regions: right/left commissure 920, right/non-coronary commissure 922, and left/non-coronary commissure 924. FIG. 9B illustrates a 2-D side view of the target site 900 taken in an image plane 932 (represented as a line in FIG. 9A). The image plane 932 is approximately perpendicular to an image plane 930 (represented as a line in FIG. 9A) in an x-direction and y-direction, and the image plane 932 extends in the z-direction (a direction normal to the 2D view of FIG. 9A). FIG. 9C illustrates a 2-D side view of the target site 900 taken in the image plane 930. The image plane 930 approximately bisects the right coronary cusp 902 in the x-direction and y-direction (e.g., approximately perpendicular to the image plane 932) and extends in the z-direction.

Figures 9D, 9E:
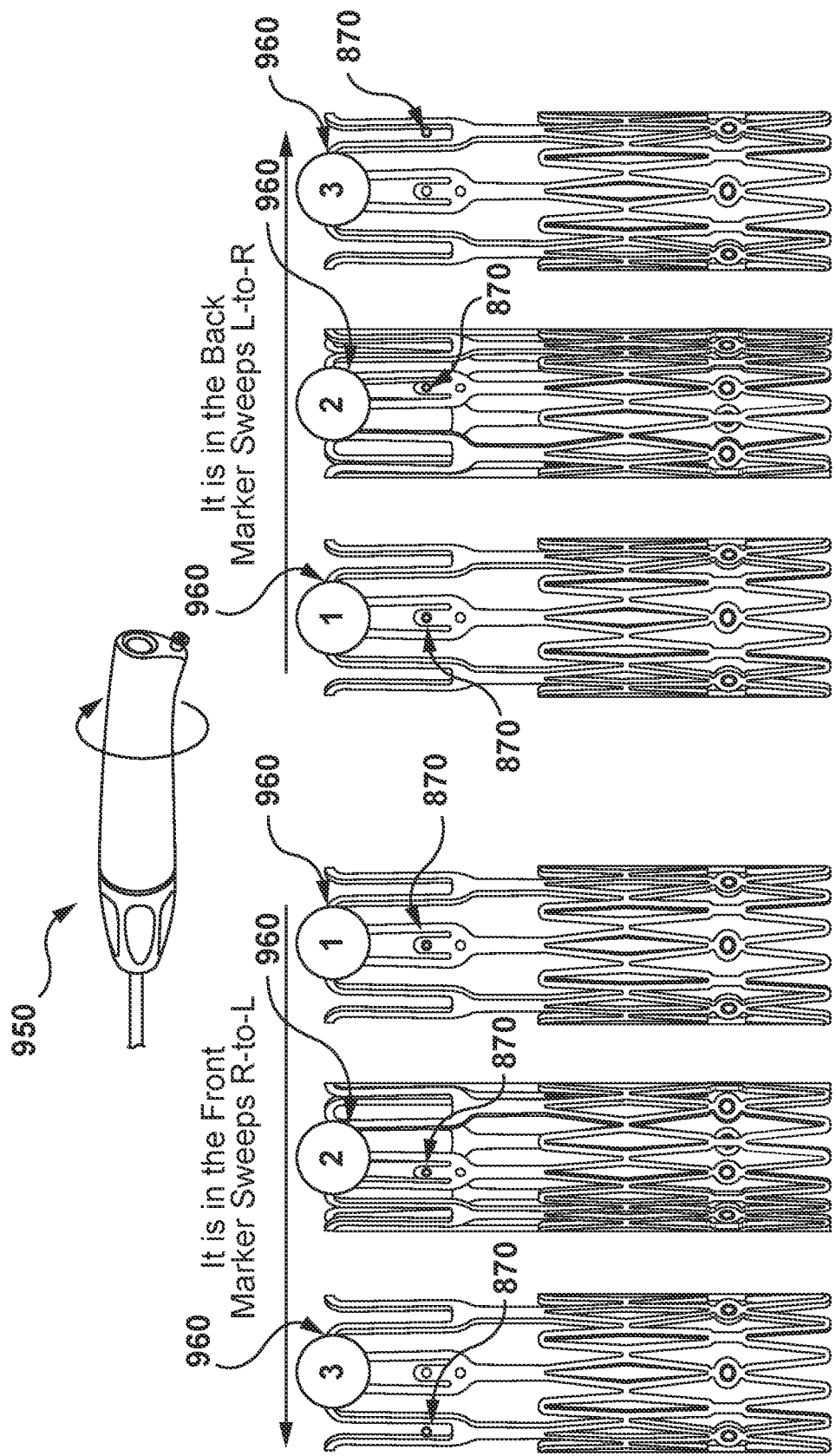
Figure 9F:
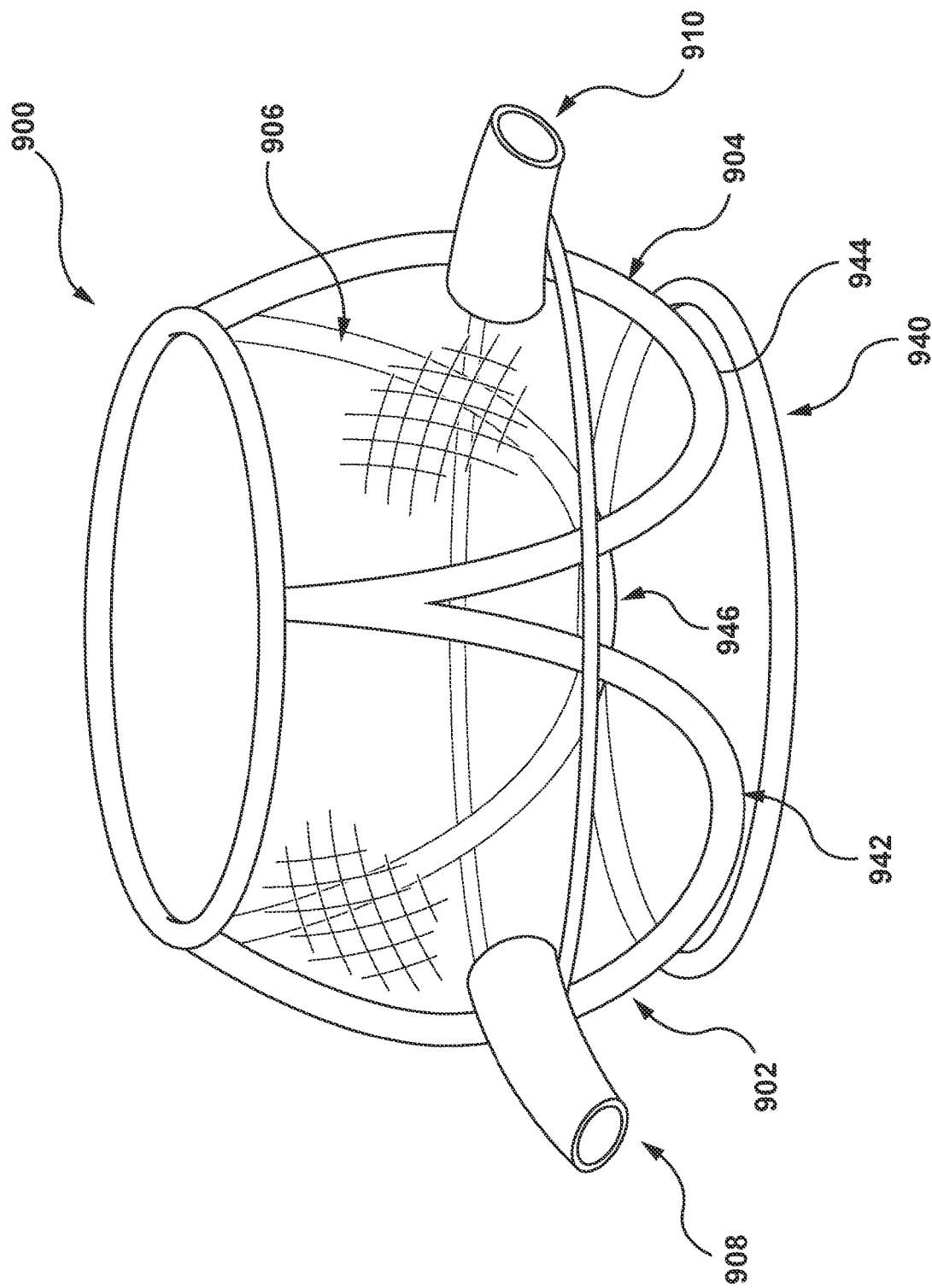

As illustrated in FIG. 9B, the inflow markers 860 can be utilized to axially align the stent 802 with features in the target site 900, e.g., basal plane 940 of the right coronary cusp 902, the left coronary cusp 904 and the non-coronary cusp 906. For example, as illustrated in FIG. 9F, which is a three dimension view of the target site 900, the basal plane 940 can be defined as a plane that intersects a nadir 942 of the right coronary cusp 902, a nadir 944 of the left coronary cusp 904, and a nadir 946 of the non-coronary cusp 906. To align the transcatheter valve prosthesis 800, the stent 802, via a delivery system (e.g., delivery system 100), can be manipulated (e.g., advanced, retracted, etc.) until the inflow markers 860 align with the basal plane 940, as illustrated in FIG. 9B. As such, the transcatheter valve prosthesis 800 can be positioned at a proper depth within the target site 900, thereby ensuring proper engagement with the native tissue.

Additionally, the inflow markers 860 can be utilized to align the tilt and/or rotation of the stent 802. For example, to align the transcatheter valve prosthesis 800, the stent 802, via a delivery system (e.g., delivery system 100), can be manipulated (e.g., rotated, tilted, etc.) until the inflow markers 860 form a predetermined pattern visible in the image captured in the image plane 930 and/or 932, for example, as described above with reference to FIGS. 3A-3G. For example, as illustrated in FIGS. 9D and 9E, the stent 802 may include six (6) inflow markers 860. As the stent 802 is rotated, different numbers of the inflow markers 860 may be visible in the 2D image, e.g., 6 markers in image 2 and 6 markers in image 3. In this example, to align the transcatheter valve prosthesis 800, the delivery system (e.g., the delivery system 100) can be manipulated (e.g., rotated, tilted, etc.) until all 6 of the inflow markers 860 form a predetermined pattern, e.g., only 3 inflow markers 860, that is visible in the image captured in the image plane 932. In other words, 3 of the inflow markers 860 overlap and obscure the other 3 of the inflow markers 860 in the 2D image. If the image plane 932 is aligned with the native anatomy as desired, the appearance of the predetermined pattern, e.g., only 3 inflow markers 860, indicates the transcatheter valve prosthesis 800 is approximately perpendicular to image plane 932 indicating proper orientation (e.g., indicating proper tilt, proper rotation, etc.) of the transcatheter valve prosthesis 800, as shown in FIG. 9D and FIGS. 9E, image 3.

In embodiments, the first outflow marker 870 can be utilized to align circumferential or rotational orientation of the transcatheter valve prosthesis 800. More particularly, the first outflow marker 870 can allow a physician to correctly interpret the circumferential orientation of the transcatheter valve prosthesis 800 and to clock or rotate the transcatheter valve prosthesis 800 relative to the anatomy to correct the circumferential or rotational orientation, if necessary, to avoid blocking the ostia of the right coronary artery 908 and/or the left main coronary artery 910. In addition, the first outflow marker 870 clocks the commissures of the transcatheter valve prosthesis 800 so they rotationally align with the native valve commissures. Commissure to commissure alignment (transcatheter valve prosthesis 800 commissure to native commissure) may improve transcatheter valve prosthesis 800 hemodynamics and leaflet durability. To align the transcatheter valve prosthesis 800, the stent 802 can rotated, in situ. by a delivery system (e.g., delivery system 100) to be positioned in a desired circumferential or rotational alignment.

For example, to avoid blocking the ostia of the left main coronary artery 910, the first outflow marker 870 can be positioned on the stent 802 such that for proper rotational orientation of the stent 802, the first outflow marker 870 is aligned with the left/non-coronary commissure 924 of the left coronary cusp 904 and the non-coronary cusp 906. As illustrated in FIG. 9B, if viewed in the image plane 932 (parallel to the annulus 901 and bisecting the right coronary cusp 902), the first outflow marker 870 can be rotated until the first outflow marker 870 is centered in the image, thereby indicating alignment with the left/non-coronary commissure 924. Likewise, for example, as illustrated in FIG. 9C, if viewed in the image plane 930 (parallel to the annulus 901 and perpendicular to the image plane 932), the first outflow marker 870 can be rotated until the first outflow marker 870 appears in the right of the image, thereby indicating alignment with the left/non-coronary commissure 924. This alignment ensures that the commissure post 826A does not block the ostia of the left main coronary artery 910. Likewise, this alignment can allow the additional commissure post 826A to be aligned with the right/left commissure 920 and the right/non-coronary commissure 920. While the above describes, the first outflow marker 870 being aligned with the left/non-coronary commissure 924, the first outflow marker 870 can be aligned with other structure at the target site 900, e.g., right/left commissure 920, right/non-coronary commissure 922, etc.

In embodiments, the first outflow marker 870 can also be used as a guide to a front or rear location of the first outflow marker 870 appearing in 2D image. That is, the first outflow marker 870 can be utilized to determine whether the first outflow marker 870 is positioned on a side of the stent 802 closest to the imaging apparatus (front location) or positioned on a side of the stent 802 furthest from the imaging apparatus (rear location). FIGS. 9D and 9E illustrate several sequential images 960 captured in the image plane 932 as the transcatheter valve prosthesis 800 is rotated in different directions using a handle 950 of a delivery system (e.g., delivery system 100.)

As illustrated in FIG. 9D and FIG. 9E, as the handle 950 is rotated in a clockwise direction (thereby rotating the stent 802 counter-clockwise), the first outflow marker 870 moves in the images 960 to the right or left depending on the front or rear location of the first outflow marker 870. That is, based on the transcatheter approach to the target site 900, a tip of the delivery system 100 may be point in a direction opposite the direction of the handle 950 (e.g., in a direction back towards the handle 950), thereby causing the stent 802 to rotate in a direction opposite a direction of rotation of the handle 950, when viewed in a 2D image. For example, as illustrated in FIG. 9D, as the handle 950 is rotated clockwise (thereby rotating the stent 802 counter-clockwise), the first outflow marker 870 moves from right to left in the images 960, thereby indicating that the first outflow marker 870 is in the front (where an emitter of the imaging device is positioned on the front side of the stent 802 and the detector being is on a back side of the stent 802). As illustrated in FIG. 9E, as the handle 950 is rotated clockwise (thereby rotating the stent 802 counter-clockwise), the first outflow marker 870 moves from left to right in the images 960, thereby indicating that the first outflow marker 870 is in the rear (on the back side of the stent 802 relative to positioning of the imaging device). If the handle 950 is rotated counter-clockwise (thereby rotating the stent 802 clockwise), the above movements would be reversed, e.g., left to right movement in the images would indicate front and right to left would indicate rear. While the particular movement of the first outflow marker 870 is discussed above in reference to transcatheter approach, one skilled in the art will realize that the relative movement of the first outflow marker 870 may change based on a different approach.

Figure 10A:
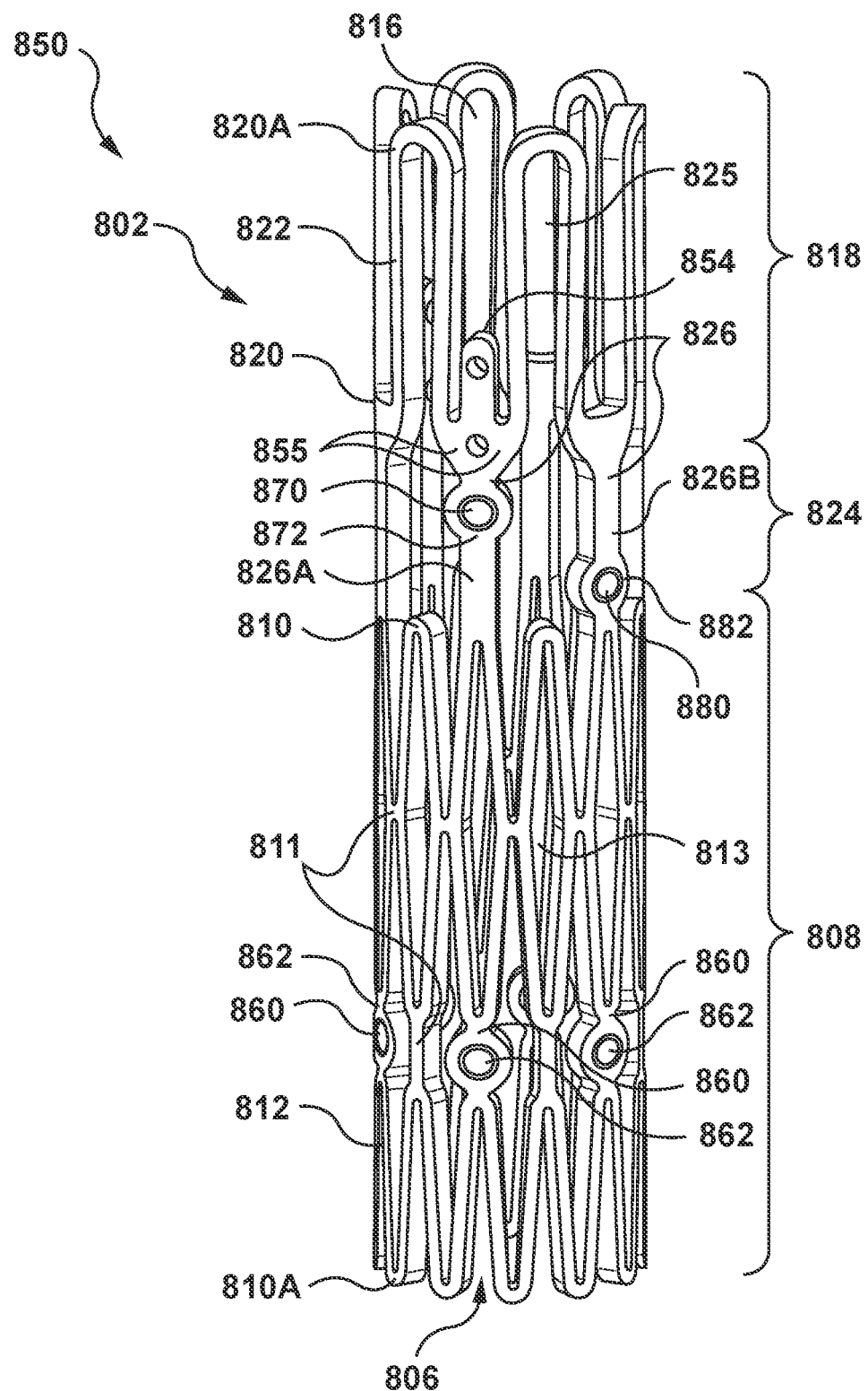
FIGS. 10A-10C illustrate another transcatheter valve prosthesis in accordance with an embodiment hereof.
Figure 10B:
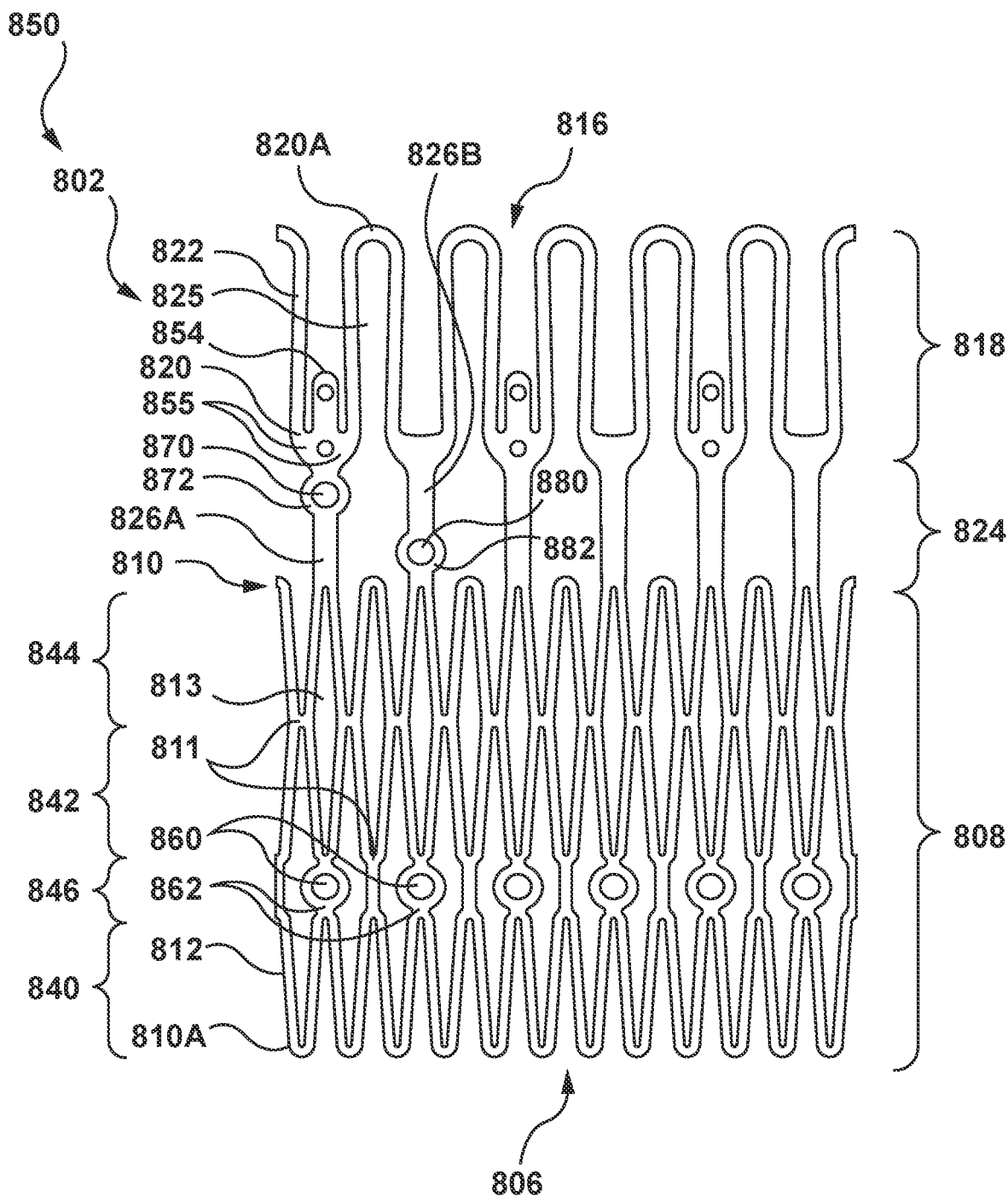
Figure 10C:
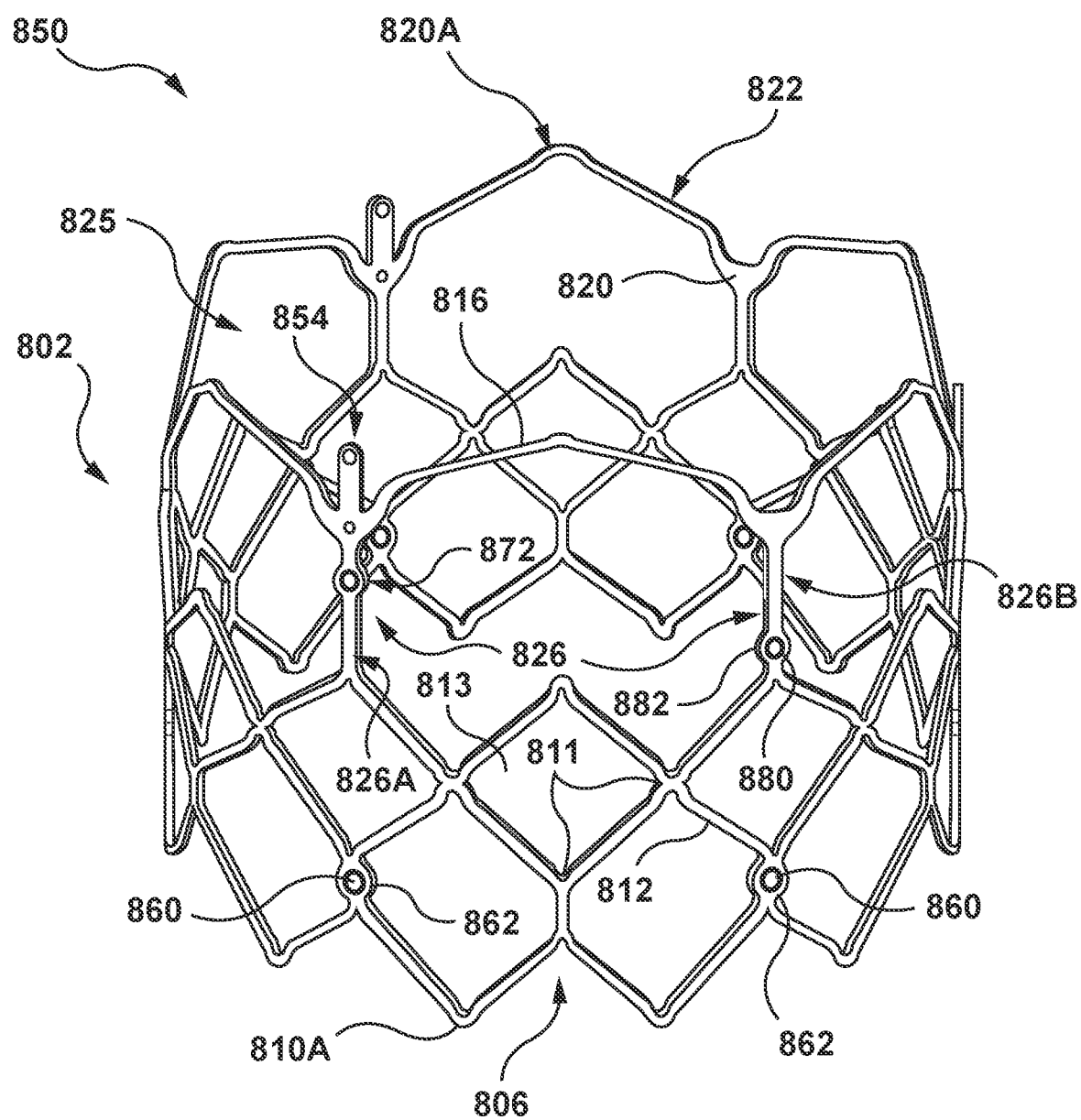

FIGS. 10A-10C illustrate a transcatheter valve prosthesis 850, which is a non-limiting example of an implantable medical device 102, in which a radially-expandable stent 802 one or more inflow markers 860, the first outflow marker 870, and an second outflow marker 880, according to another embodiment hereof. In embodiments, the inflow markers 860, the first outflow marker 870, and the second outflow marker 880 can be utilized in orientation (e.g., axial/annular alignment, tilt alignment, circumferential (rotational) alignment, etc.) of the transcatheter valve prosthesis 850, in situ, as discussed in detail below:

One skilled in the art will realize that FIGS. 10A-10C illustrate one example of an implantable medical device and that existing components illustrated in FIGS. 10A-10C may be removed and/or additional components may be added. Additionally, while the transcatheter valve prosthesis 850 is described below as including the one or more inflow markers 860, the first outflow marker 870, and the second outflow marker 880, one skilled in the art will realize that the transcatheter valve prosthesis 850 can include additional markers, for example, any of the markers described herein. Moreover, while examples of operations and advantages of the transcatheter valve prosthesis 850 one or more inflow markers 860, first outflow marker 870, and second outflow marker 880 are discussed below, one skilled in the art will realize any of the operations and processes described above can be performed using the transcatheter valve prosthesis 850.

As discussed above, the stent 802 of the transcatheter valve prosthesis 850 has a non-expanded or crimped, which is shown in a side view of FIG. 10A, and an expanded configuration, which is shown FIG. 10C. FIG. 10B shows an open, flat view of an example of the stent 802 with a circular or ellipsoidal example of the unitary frame. As illustrated in FIGS. 10A-10C, the transcatheter valve prosthesis 850 can include similar components to the transcatheter valve prosthesis 800, a description of which can be found above in the discussion of FIGS. 8A-8E. Additionally, the transcatheter valve prosthesis 850 can include the second outflow marker 880. The second outflow marker 880 can be utilized in combination with the first outflow marker 870 to align the circumferential or rotation orientation of the stent 802, as discussed below.

In embodiments, the second outflow marker 880 can be positioned on an axial strut 826B. In an embodiment, the second outflow marker 880 can be positioned on an axial strut 826B that is adjacent (e.g., adjacent in a clockwise direction or adjacent in a counter clockwise direction) to the commissure post 826A containing the first outflow marker 870. As illustrated in FIG. 10A-10C, the second outflow marker 880 can be attached to the stent 802 within a containment member 882 formed in an axial strut 826B. The containment member 882 can be configured as a hollow structure or opening in the axial strut 826B which can receive the second outflow marker 880. In an embodiment, the containment member 882 can be open to the interior and exterior of the stent 802, thereby allowing the second outflow marker 880 to be exposed to the interior and exterior of the stent 802 and increasing visibility at multiple angles. In some embodiments, the containment member 882 can be open only to the interior or exterior of the stent 802, thereby forming a cavity or depression in the stent 802. While the above discloses an example of the positioning of the first outflow marker 870) and the second outflow marker 880, one skilled in the art will realize that the first outflow marker 870 and the second outflow marker 880 can be positioned on any component of the outflow portion 818 and/or transition portion 824.

The containment member 882 can be configured in a shape that matches a shape of the second outflow marker 880. For example, as illustrated in FIGS. 8A-8C, if the second outflow marker 880 have a circular cross-sectional shape, the containment member 882 can be define a cavity that is circular, e.g., a hollow ring. In some embodiments, the containment member 882 need not extend from an exterior or an interior of the axial strut 826B such that the containment member 882 includes a surface aligned with the exterior surface or interior surface of the stent 802. In some embodiments, the containment member 882 may extend from an exterior or an interior surface of the axial strut 826B.

In some embodiments, when placed in the containment member 882, the second outflow marker 880 may be contained within the containment member 882 and may be recessed from an exterior and/or an interior surface of the axial strut 826B. In some embodiments, when placed in the containment member 882, the second outflow marker 880) may be contained within the containment member 882 and may be flush with an exterior and/or an interior surface of the axial strut 826B. In some embodiments, when placed in the containment member 882, the second outflow marker 880 may be extend from the containment member 882 and may be extend from an exterior and/or an interior surface of the axial strut 826B.

In embodiments, the second outflow marker 880 can be attached to, positioned in, and/or formed in the containment member 882 utilizing any type of processes and/or procedure. In an embodiment, radiopaque beads or spheres (or lines of radiopaque beads or spheres) may be press fit, swaged, interference fit, etc. into the containment member 882. In an embodiment, the axial strut 826B may not include a containment member 882. In this embodiment, the second outflow marker 880 may be attached and/or applied to the axial strut 826B. For example, the second outflow marker 880 may comprise radiopaque bands that are attached to the axial strut 826B. Likewise, for example, the second outflow marker 880 may be formed by applying radiopaque materials to the axial strut 826B in any shape. One skilled in the art will realize that the second outflow marker 880 may be attached to or formed on the axial strut 826B utilizing any processes as required by the design of the stent 802 and/or application of the transcatheter valve prosthesis 850.

In any embodiment, the second outflow marker 880 can be formed in any shape to assist in the alignment of the transcatheter valve prosthesis 800. In embodiments, as illustrated in FIGS. 10A-10C, the second outflow marker 880 can be formed in a circular cross-sectional shape. In other embodiments, the second outflow marker 880 can be formed in any other 2D or 3D shape, which has any type of 2D or 3D cross-sectional shape, such as pins, dots, ovals, spheres, triangles, cones, squares, cubes, bars, crosses, bands, rings, letters, and combination thereof. One skilled in the art will realize that other configurations and shapes of the outflow marker may be provided to provide a benefit for a given application.

In any embodiment, the second outflow marker 880 include radiopaque or other material that allow the second outflow marker 880 to be detected and/or viewed during the installation of the transcatheter valve prosthesis 850. Examples of radiopaque materials include metals, e.g., stainless steel, titanium, tungsten, tantalum, gold, platinum, platinum-iridium, and/or other polymeric materials, e.g., nylon, polyurethane, silicone, pebax, PET, polyethylene, that have been mixed or compounded with compounds of barium, bismuth and/or zirconium, e.g., barium sulfate, zirconium oxide, bismuth sub-carbonate, etc.

In any embodiment, the second outflow marker 880 can be formed to dimensions such that the second outflow marker 880 do not affect the operation of the transcatheter valve prosthesis 800. For example, the second outflow marker 880 can be formed to not extend beyond the exterior diameter of the stent 802 or extend into the central lumen of the stent 802, e.g., e.g., having a radial depth that is equal to or less than the radial depth of the axial strut 826B. In an embodiment, the second outflow marker 880 can have a circular cross-sectional shape with a diameter ranging between approximately 0.5 mm and 1.0 mm, for example, approximately 0.8 mm. In this embodiment, the containment member 882 can have a circular cross-sectional shape with a diameter ranging between approximately 0.5 mm and 1.0 mm, for example, approximately 0.8 mm. In another embodiment, the second outflow marker 880 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm. In this embodiment, the containment member 882 can have an elliptical cross-sectional shape with an axial diameter ranging between approximately 0.5 mm and 1.0 mm, for example, approximately 0.8 mm, and a circumferential diameter ranging between approximately 0.5 mm and 1.0 mm, for example, approximately 0.9 mm.

Figure 11C:
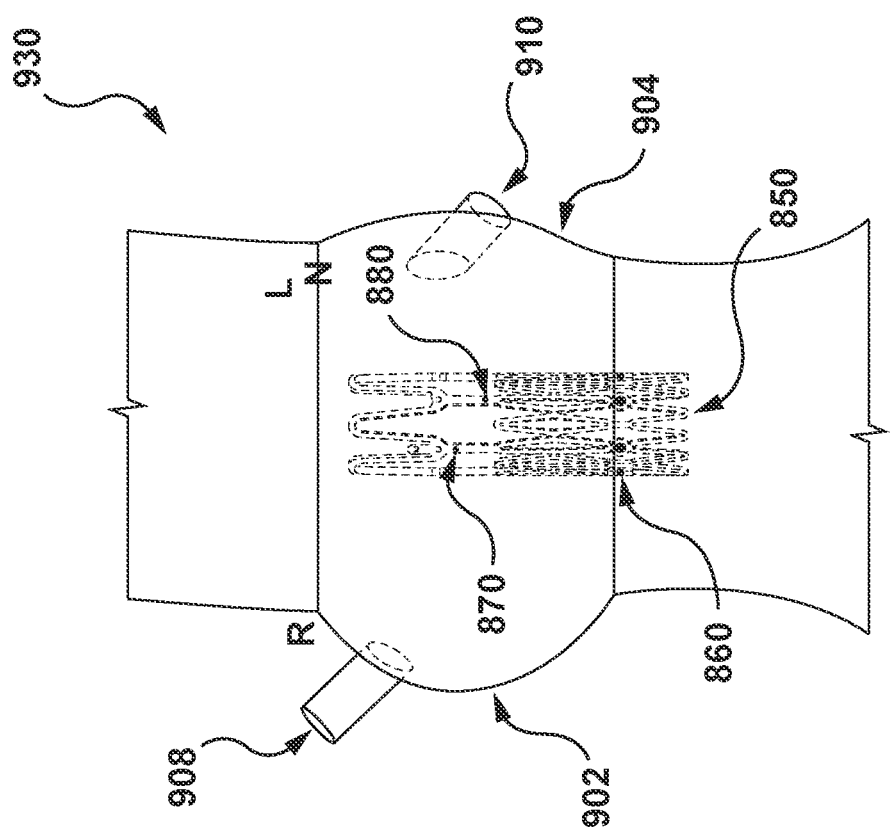

In embodiments, the inflow markers 860, the first outflow marker 870, and the second outflow marker 880 can be utilized in orientation (e.g., axial/annular alignment, tilt alignment, circumferential (rotational) alignment, etc.) of the transcatheter valve prosthesis 850, in situ, during installation as described below with reference to FIGS. 11A-11D. FIGS. 11A-11D illustrate various views of a target site 900 e.g., an aortic heart valve, for the transcatheter prosthesis 850. As illustrated in FIG. 11A, which is an annular view of the target site 900 taken perpendicular to an annulus 901, the target site 900 includes three valve cusps of the aortic root, the right coronary cusp 902, the left coronary cusp 904 and the non-coronary cusp 906. The region of the right coronary cusp 902 includes ostia of the right coronary artery 908. Likewise, the region of the left coronary cusp 904 includes ostia of the left main coronary artery 910.

When installing the transcatheter valve prosthesis 850, it is desirable to properly align the stent 802 with the target site 900, as discussed above. For example, the transcatheter valve prosthesis 850 needs to be properly aligned, axially/annularly, so that the transcatheter valve prosthesis 850 properly engages the native tissue of the target site 900. Likewise, the transcatheter valve prosthesis 850 needs to be aligned circumferentially or rotationally. When being positioned, in situ, it is very important to avoid blocking the ostia of the right coronary artery 908 and/or the left main coronary artery 910. Proper circumferential or rotational orientation within the target site 900 may reduce the risk of blocking coronary access and may enhance hemodynamics and valve durability because of commissure-to-commissure alignment. As illustrated in FIG. 11A, the right coronary cusp 902, the left coronary cusp 904, and the non-coronary cusp 906 include commissure regions: right/left commissure 920, right/non-coronary commissure 922, and left/non-coronary commissure 924. FIG. 11B illustrates a 2-D side view of the target site 900 taken in an image plane 932 (represented as a line in FIG. 11A). The image plane 932 is approximately perpendicular to an image plane 930 (represented as a line in FIG. 11A) in an x-direction and y-direction, and the image plane 932 extends in the z-direction (a direction normal to the 2D view of FIG. 11A). FIG. 11C illustrates a 2-D side view of the target site 900 taken in the image plane 930. The image plane 930 approximately bisects the right coronary cusp 902 in the x-direction and y-direction (e.g., approximately perpendicular to the image plane 932) and extends in the z-direction.

As illustrated in FIG. 11B, the inflow markers 860 can be utilized to axially align the stent 802 with features in the target site 900, e.g., basal plane 940 of the right coronary cusp 902, the left coronary cusp 904 and the non-coronary cusp 906. For example, as discussed above with reference to FIG. 9F, which is a three dimension view of the target site 900, the basal plane 940 can be defined as a plane that intersects a nadir 942 of the right coronary cusp 902, a nadir 944 of the left coronary cusp 904, and a nadir 946 of the non-coronary cusp 906. To align the transcatheter valve prosthesis 800, the stent 802, via a delivery system (e.g., delivery system 100), can be manipulated (e.g., advanced, retracted, etc.) until the inflow markers 860 align with the basal plane 940, as illustrated in FIG. 11B. As such, the transcatheter valve prosthesis 800 can be positioned at a proper depth within the target site 900, thereby ensuring proper engagement with the native tissue.

In embodiments, as described above with reference to FIGS. 9A-9E, the first outflow marker 870), alone, can be utilized to align circumferential or rotational orientation of the transcatheter valve prosthesis 850. For example, the first outflow marker 870 can be aligned to the right/left commissure 920, right/non-coronary commissure 922, or left/non-coronary commissure 924, thereby aligning the commissure post 826A to the right/left commissure 920, right/non-coronary commissure 922, or left/non-coronary commissure 924, respectively. The second outflow marker 880, alone, can similarly be utilized to align circumferential or rotational orientation of the transcatheter valve prosthesis 850. For example, the second outflow marker 880 can be aligned to the right/left commissure 920, right/non-coronary commissure 922, or left/non-coronary commissure 924, thereby aligning the axial strut 826B to the right/left commissure 920, right/non-coronary commissure 922, or left/non-coronary commissure 924, respectively. One skilled in the art will realize that the first outflow marker 870) and/or the second outflow marker 880 can be aligned to any feature at the target site 900.

In embodiments, the combination of the first outflow marker 870) and the second outflow marker 880 can be utilized to align circumferential or rotational orientation of the transcatheter valve prosthesis 850. That is, the relative appearance and/or location in a 2D image can be utilized to align circumferential or rotational orientation of the transcatheter valve prosthesis 850. In particular, the relative radial appearance in 2D image can indicate the relative positioning of the outflow markers 870 and 880 when an image plane is aligned to a desired feature at the target site 900. For example, to avoid blocking the ostia of the left main coronary artery 910, the commissure post 826A, containing the first outflow marker 870, can be aligned with the right/left commissure 920 of the right coronary cusp 902 and the left coronary cusp 904, as illustrated in FIG. 11A. Because the second outflow marker 880) positioned adjacent to the first outflow marker 870, the axial strut 826B will be aligned near the left main coronary artery 910.

The first outflow marker 870 and the second outflow marker 880 can be utilized in combination for circumferential or rotational alignment by setting up an image plane to be approximately parallel to the desired alignment feature and rotating the stent 802 until the first outflow marker 870 and the second outflow marker 880 appear with no radial offset. When aligning the second outflow marker 880, the image plane can be aligned with a desired feature of the target site 900. For example, to align the axial strut 826B, containing the second outflow marker 880, to the left coronary artery, the imaging device can be positioned to produce an image in the image plane 932, which is normal to the left/non-coronary commissure 924. The relative radial appearance in a 2D image from the image plane 932 can indicate the relative positioning of the first outflow marker 870 and the second outflow marker 880 can be utilized to indicate proper alignment. That is, proper alignment can be indicated by both the first outflow marker 870) and the second outflow marker 880 appearing on the right side of the image, as illustrated in FIG. 11B.

As illustrated in FIG. 11B, when the axial strut 826B, containing the second outflow marker 880, is aligned with the left coronary, the first outflow marker 870) and the second outflow marker 880 appear to be in a straight line (e.g., no radial offset) in the 2D image. This is due to the first outflow marker 870 and the second outflow marker 880 lying in the image plane 932 or being perpendicular, along an axial line, to the image plane 932 relative to the imaging device. As illustrated in FIG. 11C, when the first outflow marker 870 and the second outflow marker 880 do not approximately lie in or are perpendicular, along an axial line, to an image plane, e.g., image plane 930, the first outflow marker 870 and the second outflow marker 880 appear radially offset.

Figure 11D:
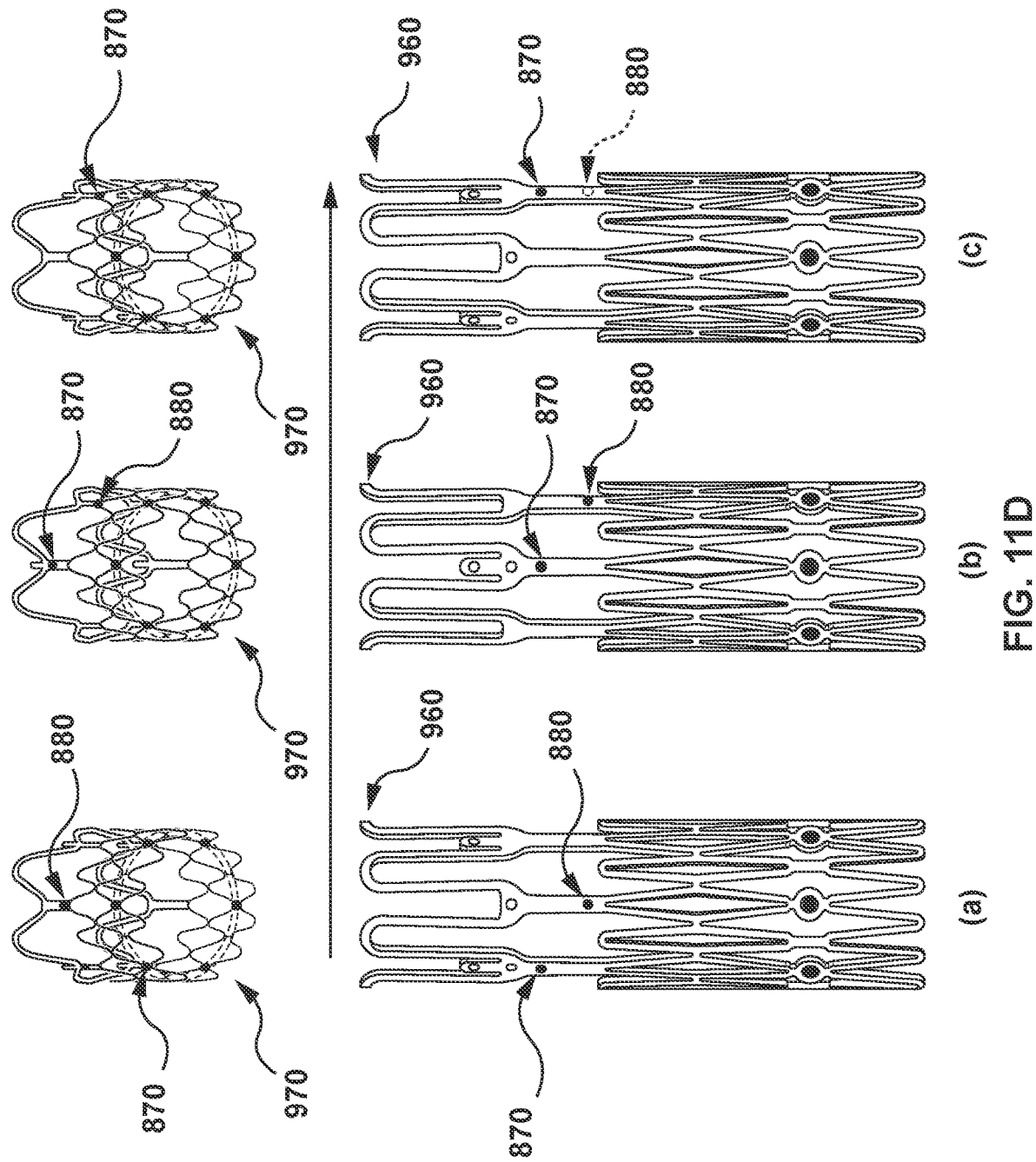

To align the transcatheter valve prosthesis 850, the stent 802 can be rotated, in situ. by a delivery system (e.g., delivery system 100) until the first outflow marker 870 and the second outflow marker 880 do not appear radially offset, as illustrated in FIG. 11D. FIG. 11D illustrates several sequential images 960 captured in the image plane 930, and corresponding images 970 captured in the annular image plane, as the transcatheter valve prosthesis 850 is rotated using a handle 950 of a delivery system (e.g., delivery system 100.) For example, in FIG. 11D, panel (a), the first outflow marker 870 and the second outflow marker 880 appear radially offset. To align the transcatheter valve prosthesis 800, the stent 802 can rotated, in situ. by a delivery system (e.g., delivery system 100) until the first outflow marker 870 and the second outflow marker 880 do not appear radially offset (e.g., in a straight line) as illustrated in FIG. 11D, and panel (c), thereby indicating the first outflow marker 870 and the second outflow marker 880 lying in the image plane 930 or being perpendicular to the image plane 930 relative to the imaging device.

In embodiments, the first outflow marker 870 and/or the second outflow marker 880, alone, can also be used as a guide to the front or rear location of the first outflow marker 870 appearing in 2D image, as described above. The relative motion of the first outflow marker 870 and the outflow markers 880, when rotated, can be used to indicate the front or rear location of the first outflow marker 870 appearing in 2D image. In particular, the right or left location of the first outflow marker 870 relative to the outflow markers 880, during rotation of the stent 802, can indicate the front or rear location. For example, if the second outflow marker 880 is placed on an axial strut 826B to the left of the commissure post 826A containing the first outflow marker 870, the appearance of the second outflow marker 880 to the left of the first outflow marker 870, during rotation, would indicate a front location, as shown in FIG. 11D, panel (a). Likewise, the appearance of the outflow marker to the right of the first outflow marker 870 would indicate a rear location. While the particular movement of the first outflow marker 870 is discussed above in reference to transcatheter approach, one skilled in the art will realize that the relative movement of the first outflow marker 870 may change based on a different approach.

In any embodiment described above, the inflow markers 860, the first outflow marker 870, and/or the second outflow marker 880 include radiopaque or other material that allow the inflow markers 860, the first outflow marker 870, the second outflow marker 880 during the installation of the transcatheter valve prosthesis 800 and 850 as described above in further detail.

In any embodiment described above, the inflow markers 860, the first outflow marker 870, and/or the second outflow marker 880 can be formed as a directional marker that assists in the circumferential (rotational) orientation based on the shape of the directional marker. For example, the inflow markers 860, the first outflow marker 870, and/or the second outflow marker 880 include formed in and/or can include an element that appears differently based on the rotational orientation, e.g., "C-shaped," "P-shaped," etc. The directional marker can assist a physician with correctly orienting the transcatheter valve prosthesis 800 and/or 850, in situ. The directional marker can allow a physician to correctly interpret the circumferential orientation of the transcatheter valve prosthesis 800 and/or 850 and to clock or rotate the transcatheter valve prosthesis 800 and/or 850 relative to the anatomy to correct the circumferential or rotational orientation if necessary. As discussed above, when being positioned in situ, it is very important to avoid blocking the ostia of the right coronary artery and/or the left main coronary artery and attaining commissure-to-commissure alignment. Proper circumferential or rotational orientation within the native anatomy reduces the risk of blocking coronary access.

The transcatheter valve prosthesis 800 and/or 850 is rotatable, in situ. by the delivery system to be positioned in a desired orientation. When formed as a direction marker, the inflow markers 860, the first outflow marker 870, and/or the second outflow marker 880 can further assist the physician to determine the orientation of the stent 802, in situ, and rotate the transcatheter valve prosthesis relative to the anatomy if needed to avoid blocking the coronary arteries and attaining commissure-to-commissure alignment.

For example, the inflow markers 860, the first outflow marker 870, and/or the second outflow marker 880 can be formed as directional marker that includes a C-shaped feature. Because the C-shape of the directional marker looks different when viewed from a front view or position as compared to when viewed from a reverse view or position, the physician can determine whether a particular portion of the stent 802, a commissure post 826A, etc., is facing toward or away from the viewing direction. In other words, the C-shape of the directional marker can be an axially non-symmetrical element such that depending upon the location, in situ. the C-shape of the directional marker may be displayed to the physician as a "C" or may be displayed to the physician backwards or as a mirror image of a "C". Since the optimal circumferential or rotational orientation of the transcatheter valve prosthesis 800 and/or 850 relative to the coronary arteries can be verified prior to releasing the transcatheter valve prosthesis 800 and/or 850 from the delivery system, the physician can ensure that the transcatheter valve prosthesis 800 and/or 850 is properly oriented in the native anatomy so as to not block the coronary arteries and commissure-to-commissure alignment. In embodiments, the inflow markers 860, the first outflow marker 870, and/or the second outflow marker 880 can be formed as directional marker that is formed as or includes any letter, number, symbol, or shape that looks different when viewed from a front view or position as compared to when viewed from a reverse view or position, e.g., a letter "P," a letter "S," a number "7," etc.

Figure 12:
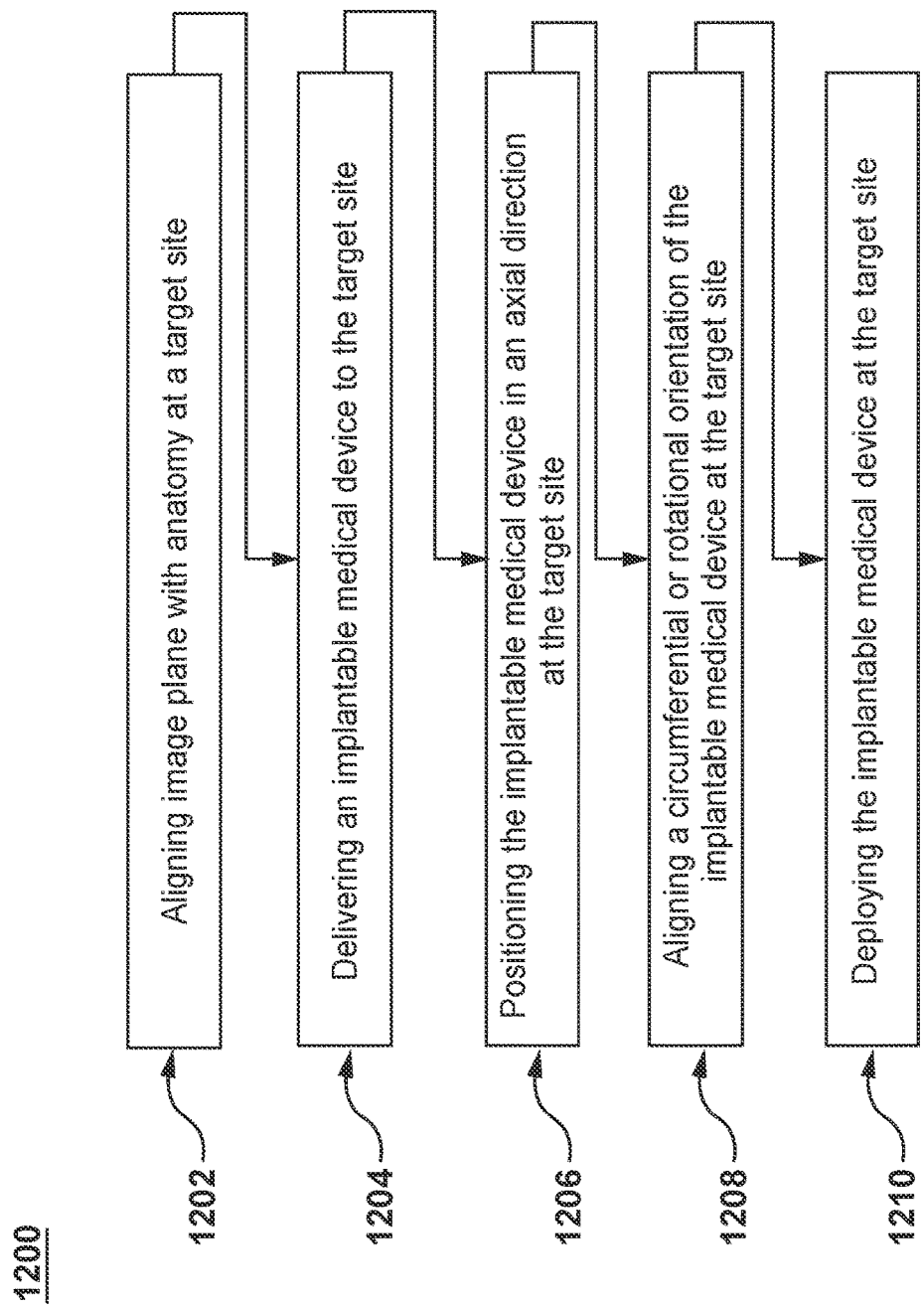
FIG. 12 depicts a flow of a method for operating of the delivery system of the delivery system of FIGS. 1A and 1B with the transcatheter valve prosthesis of FIGS. 8A-8E or FIGS. 10A-10C in accordance with an embodiment hereof.

FIG. 12 illustrates a method 1200 of operating of the delivery system 100 utilizing the inflow markers 860, the first outflow marker 870, and/or the second outflow marker 880 in accordance with an embodiment hereof. One skilled in the art will realize that FIG. 12 illustrates one example of steps that can be performed and that existing steps illustrated in FIG. 12 may be removed and/or additional steps may be added to the method 1200.

In step 1202, an image plane of an imaging device is aligned with anatomy at a target site. For example, as discussed above with reference to FIGS. 11A-11D, the imaging device 200, producing images, can be aligned with the anatomy of the patient (e.g., an annulus) to produce images in an image plane 930 and/or 932. One skilled in the art will realize that the images in the image plane 930 and/or 932 are examples and that the operations and procedures described herein can be performed using 2D image produced in any image plane of the target site and/or using 3D images of the target site.

In step 1204, an implantable medical device is delivered to the target site. In embodiments, the transcatheter valve prosthesis 800 and/or 850 can be loaded onto the delivery system 100, which is then utilized to deliver the implantable medical device to the target site. Delivery of the transcatheter valve prosthesis 800 and/or 850 can be accomplished via any type of procedure utilized to install medical devices in patients. For example, delivery of the transcatheter valve prosthesis 800 and/or 850 by the delivery system 100 can be accomplished via a percutaneous transfemoral approach or a transapical approach directly through the apex of the heart via a thoracotomy, or may be positioned within the desired area of the heart via different delivery methods known in the art for accessing heart valves. During delivery, the stent 802 of the transcatheter valve prosthesis 800 and/or 850 remains compressed (in a crimped state) until it reaches a target site, e.g., a diseased native heart valve.

In step 1206, the implantable medical device is positioned in an axial direction at the target site. In embodiments, the inflow markers 860 of the transcatheter valve prosthesis 800 and/or 850 can be utilized to position the stent 802 in the axial direction relative to native annulus. This may ensure a correct implant depth of the transcatheter valve prosthesis 800 and/or 850.

For example, the inflow markers 860 can be utilized to axially/annularly align the stent 802 with features in the target site 900, e.g., the basal plane 940 of the right cusp 902, the left cusp 904 and the non-coronary cusp 906. For example, the inflow markers 860 can be aligned with the basal plane 940 of the right cusp 902, the left cusp 904 and the non-coronary cusp 906. To align the transcatheter valve prosthesis 800 and/or 850, the stent 802, via a delivery system (e.g., delivery system 100), can be manipulated (e.g., advanced, retracted, etc.) until the inflow markers 860 align with the basal plane 940 of the right coronary cusp 902, the left coronary cusp 904 and the non-coronary cusp 906.

In step 1208, a circumferential or rotational orientation of the implantable medical device is aligned at the target site. In embodiments, the outflow markers 870 and outflow markers 880 operate solely or in combination to provide visual references to an orientation of the transcatheter valve prosthesis 800 and/or 850 relative to the native structure of the target site of the transcatheter valve prosthesis 800 and/or 850 is being installed.

For example, the first outflow marker 870 or the second outflow marker 880 can be utilized to align circumferential or rotational orientation of the transcatheter valve prosthesis 800 and/or 850. More particularly, the first outflow marker 870 or the second outflow marker 880 can allow a physician to correctly interpret the circumferential orientation of the transcatheter valve prosthesis 800 and to clock or rotate the transcatheter valve prosthesis 800 and/or 850 relative to the anatomy to correct the circumferential or rotational orientation, if necessary, to avoid blocking the ostia of the right coronary artery 908 and/or the left main coronary artery 910 and attain commissure-to-commissure alignment. To align the transcatheter valve prosthesis 800 and/or 850, the stent 802 can rotated, in situ. by a delivery system (e.g., delivery system 100) to be positioned in a desired circumferential or rotational alignment using the first outflow marker 870 or the second outflow marker 880 as a visual reference, as described above.

Likewise, for example, the first outflow marker 870) and the second outflow marker 880) can be utilized in combination for circumferential or rotational alignment by rotating the stent 802 until the first outflow marker 870 and the second outflow marker 880) appear with no radial offset. For instance, to align the axial strut 826B, containing the second outflow marker 880, to the left coronary, the imaging device can be positioned (in step 1202) to produce an image in the image plane 932, which is parallel to the annulus 901 and perpendicular to the left/non-coronary commissure 924. As illustrated in FIG. 11B (as discussed above), when the axial strut 826B, containing the second outflow marker 880, is aligned with the left coronary, the first outflow marker 870) and the second outflow marker 880 appear to be in a straight line (e.g., no radial offset) in the 2D image. This is due to the first outflow marker 870 and the second outflow marker 880 lying in the image plane 932 or being perpendicular to the image plane 932 relative to the imaging device. To align the transcatheter valve prosthesis 850, the stent 802 can be rotated, in situ, by a delivery system (e.g., delivery system 100) until the first outflow marker 870) and the second outflow marker 880 do not appear radially offset, as illustrated in FIG. 11D (described above).

Additionally, for example, the inflow markers 860 can be utilized to align the tilt and/or rotation of the stent 802. For example, to align the transcatheter valve prosthesis 800 and/or 850, the stent 802, via a delivery system (e.g., delivery system 100), can be manipulated (e.g., rotated, tilted, etc.) until the inflow markers 860 form a predetermined pattern visible in the image captured in the image plane 930 and/or 932, for example, as described above with reference to FIGS. 3A-3G and FIGS. 9A-9E.

In step 1210, the implantable medical device is deployed at the target site. In embodiments, the transcatheter valve prosthesis 800 and/or 850 can be deployed. In embodiments, the transcatheter valve prosthesis 800 and/or 850 can be deployed using the expansion device 126 of the delivery system 100. For example, the operator of the delivery system 100 can activate the expansion device 126 (e.g., inflate a balloon, release tension in one or more sutures or bands, or manipulate one or more wires or rods) in order to radially expand the stent 802, in situ. The inner shaft 114 is then removed and the transcatheter valve prosthesis 800 and/or 850 remains deployed within the native target heart valve.

In some embodiments, if the transcatheter valve prosthesis 800 and/or 850 is a replacement heart valve, the transcatheter valve prosthesis 800 and/or 850 is configured to block flow in one direction to regulate flow there-through via valve leaflets that may form a bicuspid or tricuspid replacement valve. When the transcatheter valve prosthesis 800 and/or 850 is deployed within the valve annulus of a native heart valve, the stent 802 of the transcatheter valve prosthesis 800 and/or 850 is configured to be radially expanded within native valve leaflets of the defective valve, to thereby retain the native valve leaflets in a permanently open state. In some embodiments, the transcatheter valve prosthesis 800 and/or 850 is configured for replacement for an aortic valve such that an inflow end of the transcatheter valve prosthesis 800 and/or 850 extends into and anchors within the aortic annulus of a patient's left ventricle, while an outflow end of the transcatheter valve prosthesis 800 and/or 850 is positioned within the aortic sinuses.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device.

What is claimed is:

1. A transcatheter valve prosthesis comprising:
 a stent having a crimped configuration for delivery within a vasculature and an expanded configuration for deployment within a native heart valve, wherein the stent comprises an inflow portion, an outflow portion, and a plurality of axial frame members connecting the inflow portion to the outflow portion, wherein the plurality of axial frame members comprises a plurality of commissure posts and a plurality of axial struts;

a first outflow marker positioned on a first commissure post of the plurality of commissure posts, wherein only the first commissure post of the plurality of commissure posts includes a marker disposed thereon and the first outflow marker is the only marker on the first commissure post; and a second outflow marker positioned on a first axial strut of the plurality of axial struts, the first axial strut being adjacent to the first commissure post, wherein only the first axial strut of the plurality of axial struts includes a marker disposed thereon and the second outflow marker is the only marker on the first axial strut, wherein one of the first outflow marker and the second outflow marker is positioned closer to an outflow end of the stent relative to the other of the first outflow marker and the second outflow marker, wherein the first outflow marker and the second outflow mater marker are visible relative to the stent in one or more images captured during delivery and deployment of the stent, and wherein the first outflow marker and the second outflow marker are positioned such that, in an image plane parallel to an annulus of the native heart valve and bisecting a right coronary cusp of the native heart valve, if the first outflow marker and the second outflow marker appear with no radial offset, the transcatheter valve prosthesis is properly rotationally aligned.

2. The transcatheter valve prosthesis of claim 1, wherein the first outflow marker is configured to be aligned with a native commissure of the native heart valve.

3. The transcatheter valve prosthesis of claim 1, wherein the first outflow marker and the second outflow marker are offset by sixty degrees circumferentially.

4. A method for rotationally orienting a transcatheter valve prosthesis in a native heart valve comprising:

delivering the transcatheter valve prosthesis in a crimped configuration to a target site at a native heart valve, the transcatheter valve prosthesis including a stent comprising an inflow portion, an outflow portion, a plurality of axial frame members coupling the inflow portion to the outflow portion, the axial frame members comprising a plurality of commissure posts and a plurality of axial struts, a first outflow marker positioned on a first commissure post of the plurality of commissure posts, and a second outflow marker disposed on a first axial strut of the plurality of axial struts, the first axial strut being adjacent to the first commissure post, wherein one of the first outflow marker and the second outflow marker is positioned closer to an outflow end of the stent relative to the other of the first outflow marker and the second outflow marker;

receiving a fluoroscopic image in a selected image plane, wherein the selected image plane is parallel to an annulus of the native heart valve and perpendicular to bisecting a right coronary cusp of the native heart valve;

determining, based on the image in the selected image plane and the first outflow marker, whether the transcatheter heart valve prosthesis is in a desired rotational orientation by determining whether the first outflow marker and the second outflow marker appear radially aligned in the right of the fluoroscopic image; and if the transcatheter heart valve prosthesis is not in the desired rotational orientation, rotating the transcatheter heart valve prosthesis such that the first outflow marker and the second outflow marker appear radially aligned in the right of the fluoroscopic image.

\* \* \* \* \*